(12) United States Patent
Lin et al.

(10) Patent No.: US 6,924,302 B2
(45) Date of Patent: Aug. 2, 2005

(54) SUBSTITUTED TRIAZOLE DIAMINE DERIVATIVES AS KINASE INHIBITORS

(75) Inventors: Ronghui Lin, East Brunswick, NJ (US); Peter J. Connolly, New Providence, NJ (US); Steven K. Wetter, Flemington, NJ (US); Shenlin Huang, Edison, NJ (US); Stuart L. Emanuel, Doylestown, PA (US); Robert H. Gruninger, Easton, PA (US); Steven A. Middleton, Flemington, NJ (US)

(73) Assignee: Ortho McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 10/029,750

(22) Filed: Dec. 21, 2001

(65) Prior Publication Data

US 2004/0077699 A1 Apr. 22, 2004

Related U.S. Application Data

(60) Provisional application No. 60/257,703, filed on Dec. 22, 2000.

(51) Int. Cl.$^7$ .................. A61K 31/496; C07D 249/08; A61P 35/00
(52) U.S. Cl. .................. 514/383; 514/384; 548/265.2; 548/266.2
(58) Field of Search .......................... 548/265.2, 266.2; 514/383, 384

(56) References Cited

U.S. PATENT DOCUMENTS

| | | | |
|---|---|---|---|
| 2,352,944 A | | 7/1944 | DGaetano |
| 5,674,886 A | * | 10/1997 | Okada et al. ............... 514/383 |
| 5,750,545 A | * | 5/1998 | Akahoshi et al. ........... 514/340 |

FOREIGN PATENT DOCUMENTS

| | | |
|---|---|---|
| GB | 1 065 964 | 4/1967 |
| WO | WO 9503286 A1 | 7/1994 |
| WO | WO 9921845 A2 | 5/1999 |
| WO | WO 0109106 A1 | 2/2001 |

OTHER PUBLICATIONS

Yakugaku et al., 1997, CAS:88:44882.*
PCT international Search Report, dated Jul. 3, 2002 for PCT Appl. No. PCT/US01/50559, which relates to U.S. Appl. No. 10/029,750.

Akahoshi, F., et al., "Synthesis and Pharmacological Activity of Triazolo [1,5–a] triazine Derivatives Inhibiting Eosinophilia," J. Med. Chem. 1998 41:2985–2993.

Davis, S. T., et al., "Prevention of Chemotherapy–Induced Alopecia in Rats by CDK Inhibitors," Science 2001 291:134–137.

Dunstan, A. R., et al., "Concise and regiospecific syntheses of tri–substituted 1,2,4–triazoles," Tetrahedron Letters 1998 39:7983–7986.

Gould, P. L., "Salt selection for basic drugs," International Journal of Pharma, 1986, 33:201–217.

Hancock, B. C., et al., "Characteristics and Significance of the Amorphous State in Pharmaceutical Systems," Journal of Pharma Sciences 1997 86(1):1–12.

Jenardanan, G. C., et al., "1–(N–Arylthiocarbamoyl) Amidino–3,5–Dimethyl Pyrazoles–Preparation and Use in Heterocycle Synthesis," Synthetic Communications 1997 27(19):3457–3462.

McKee, R. L., et al., "p–Substituted Phenyl Isothiocyanates and Some Related Thioureas," Journal of American Chem Soc 1946 68:2506–2507.

Naito, Y., et al., "Synthesis and Pharmacological Activity of Triazole Derivatives Inhibiting Eosinophilia," J. Med. Chem 1996 39:3019–3029.

Reiter, J., et al., "On Triazoles. VI[1] The acylation of 5–Amino–1,2,4–triazoles," J. Heterocyclic Chemistry 1987 24:127–142.

Ross, R., "The pathogenesis of atherosclerosis: a perspective for the 1990's," Nature 1993 362:801–808.

Webb, R. L., et al., "Diphenyl Cyancarbonimidate and Dichlorodiphenoxymethane as Synthons for the Construction of Heterocyclic Systems of Medicinal Interest," J Heterocyclic Chemistry1987 24:272–278.

Wei, G.L., et al., "Temporally and Spatially Coordinated Expression of Cell Cycle Regulatory Factors After Angioplasty," Circ. Res. 1997 80:418–426.

GenBank Accession U93306, Oct. 27, 2000.

Chem Abstract #214, Duvadie, R.K., et. al., "Novel ATP–Site Cyclin–Dependent Kinase".

Chem Abstract #215, Li, L., et. al., "Novel ATP–Site Cyclin–Dependent Kinase".

\* cited by examiner

*Primary Examiner*—Rita Desai
*Assistant Examiner*—Robert Shiao

(57) ABSTRACT

The present invention provides substituted triazole diamine derivatives as selective kinase or dual-kinase inhibitors and a method for treating or ameliorating a selective kinase or dual-kinase mediated disorder.

12 Claims, No Drawings

SUBSTITUTED TRIAZOLE DIAMINE DERIVATIVES AS KINASE INHIBITORS

This Application claims priority from U.S. provisional patent application No. 60/257,703 entitled "1,2,4-triazole-3,5-diamine derivatives" filed Dec. 22, 2000 the contents of which are hereby incorporated by reference.

FIELD OF THE INVENTION

The present invention provides substituted triazole diamine derivatives as selective kinase or dual-kinase inhibitors and a method of use thereof. More particularly, the present invention provides substituted 1,2,4-triazole-3,5-diamine derivatives as selective kinase or dual-kinase inhibitors and a method for treating or ameliorating a selective kinase or dual-kinase mediated disorder.

BACKGROUND OF THE INVENTION

Patent application WO 99/21845 describes 4-aminothiazole derivatives as inhibitors of cyclin dependent kinases of the formula:

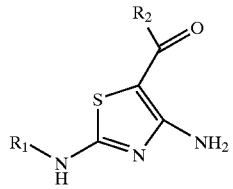

wherein
$R_1$ is a substituted or unsubstituted group selected from: $C_{1-6}$ alkyl (e.g., methyl, ethyl, propyl, isopropyl, butyl, isobutyl, sec-butyl, or tert-butyl); $C_{1-6}$-alkenyl; $C_{1-6}$-alkynyl; $C_{1-6}$-alkoxyl; $C_{1-6}$-alcohol; carbocyclic or heterocyclic cycloalkyl, which may be monocyclic or fused or non-fused polycyclic (e.g., cyclopropyl, cyclobutyl, cyclopentyl, cyclohexyl) or heterocycloalkyl, which may be monocyclic or fused or non-fused polycyclic (e.g., pyrrolidinyl, piperidinyl, morpholinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); carbonyl (e.g., carboxyl, ester, aldehyde, or ketone); ether; ($C_{1-6}$ alkyl)-carbonyl; ($C_{1-6}$ alkyl)-aryl; ($C_{1-6}$ alkyl)-cycloalkyl; ($C_{1-6}$ alkyl)-($C_{1-6}$-alkoxyl); aryl-($C_{1-6}$-alkoxyl); thioether (e.g., aryl-S-aryl, cycloalkyl-S-aryl, cycloalkyl-S-cycloalkyl, or dialkyl sulfide); thiol; and sulfonyl; and $R_2$ is a substituted or unsubstituted: carbocyclic or heterocyclic, monocyclic or fused or non-fused polycyclic, ring structure; where each optional substituent for $R_1$ and $R_2$ is independently a halogen (e.g., chloro, iodo, bromo, or fluoro); oxygen (=O); haloalkyl (e.g., trifluoromethyl); $C_{1-6}$ alkyl; $C_{1-6}$-alkenyl; $C_{1-6}$-alkynyl; hydroxyl; $C_{1-6}$-alkoxyl; carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); nitro; thiol; thioether; imine; cyano; amido; phosphonato; phosphine; carboxyl; thiocarbonyl; sulfonyl; sulfonamide; ketone; aldehyde; or ester; (ii) pharmaceutically acceptable salts of compounds of the Formula; and (iii) prodrugs and pharmaceutically active metabolites of compounds of the Formula or pharmaceutically acceptable salts thereof, and (b) a pharmaceutically acceptable carrier.

Patent application WO 01/09106 describes diamino-1,2,4-triazole-carboxylic and derivatives as GSK-3 (glycogen synthase kinase) inhibitors of formula (I):

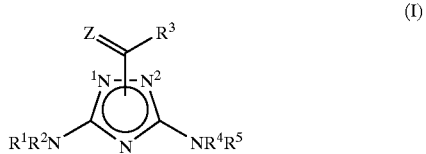

wherein
the $R^3CZ$-moiety may be attached to the nitrogen atom at position I or the nitrogen atom at position 2; $R^1$ is hydrogen, alkyl, aryl, aralkyl, aralkenyl or alicyclic; $R^2$ is hydrogen, alkyl, aryl, aralkyl, aralkenyl or alicyclic, or $R^1$ and $R^2$ together with the nitrogen atom to which they are attached may form a heterocyclic ring which ring may be unsubstituted or substituted; $R^3$ is alkyl, aryl, aralkyl, aryl(Q)alkyl, where Q is O or S, aralkenyl, alicyclic, heteroaryl, heteroaralkyl, arylcarbonylalkyl, alicyclylalkyl, diarylalkyl, or $NR^6R^7$; $R^4$ is hydrogen, alkyl, aryl, aralkyl, aralkenyl or alicyclic; $R^5$ is hydrogen, alkyl, aryl, aralkyl, aralkenyl or alicyclic, or $R^4$ and $R^5$ together with the nitrogen atom to which they are attached may form a heterocyclic ring which ring may be unsubstituted or substituted; $R^6$ is hydrogen, aryl or alicyclic; $R^7$ is hydrogen, aryl or alicyclic, and; Z is oxygen or sulphur. Suitably, $R^1$ is hydrogen or unsubstituted or substituted phenyl, wherein the substituents for the phenyl group are independently selected from up to three of $C_1$–$C_6$alkyl, $C_1$–$C_6$alkoxy, $C_1$–$C_6$alkoxy($C_1$–$C_6$)alkyl, aryl, aryloxy, halo, hydroxy, carboxy, cyano, and nitro. Favourably, $R^1$ is phenyl either unsubstituted or substituted with up to three of methyl, methoxy, or chloro. Suitably, $R^2$ is hydrogen or unsubstituted or substituted phenyl, wherein the substituents for the phenyl group are independently selected from up to three of $C_1$–$C_6$alkyl, $C_1$–$C_6$alkoxy, $C_1$–$C_6$alkoxy($C_1$–$C_6$)alkyl, aryl, aryloxy, halo, hydroxy, carboxy, cyano, and nitro. Favourably, $R^2$ is hydrogen. Suitably, $R^3$ is unsubstituted or substituted phenyl, unsubstituted or substituted naphthyl, unsubstituted or substituted benzyl, unsubstituted or substituted thienylmethyl, unsubstituted or substituted phenylthiomethyl, unsubstituted or substituted naphthylmethyl, unsubstituted or substituted furylethenyl, unsubstituted or substituted cyclohexyl, unsubstituted or substituted pyridyl, unsubstituted or substituted indolylmethyl, unsubstituted or substituted phenylcarbonylethyl, unsubstituted or substituted cyclopentenylmethyl, unsubstituted or substituted phenylpropyl, unsubstituted or substituted diphenylethyl, wherein the substituents for the $R^3$ aryl groups are selected from —$O(CH_2)_nO$—, where n is 1 to 3, or up to three of halo, aryl, perfluoro($C_1$–$C_6$)alkyl, nitro, arylcarbonyl, aryloxy, $C_1$–$C_6$acyl; or $R^3$ is $NR^6R^7$ where $R^6$ and $R^7$ are each independently hydrogen, unsubstituted or substituted aryl, or unsubstituted or substituted $C_1$–$C_6$alicyclic, wherein the substituents for the $R^6$ and $R^7$ groups are independently selected from up to three of halo, aryl, aryloxy, alkyl, nitro, and alkoxy. Favourably, $R^3$ is phenyl either unsubstituted or substituted with up to three of chloro, bromo, phenyl, trifluoromethyl, nitro, benzoyl, phenoxy, acetyl, or 3,4-OCH$_2$O—; naphthyl; benzyl either unsubstituted or substituted with up to three of phenyl or fluoro; 2-thienylmethyl; phenylthiomethyl 2-naphthylmethyl; cyclohexyl; 3-pyridyl; 3-indolylmethyl; phenylcarbonylethyl; cyclopent-2-enylmethyl; phenylpropyl; 2,2-diphenylethyl; or 2-furylethenyl; or NR$^6$R$^7$ where $R^6$ and $R^7$ are each independently hydrogen, phenyl either unsubstituted or substituted with up to three of chloro, phenyl, phenoxy, methyl, bromo, nitro, or methoxy; cyclohexyl; or 1-naphthyl. Suitably, $R^4$ is hydrogen. Suitably, $R^5$ is hydrogen. Suitably, $R^6$ is unsubstituted or substituted aryl or unsubstituted or substituted alicyclic. Favourably $R^6$ is cyclohexyl, naphthyl or phenyl which phenyl group may be either unsubstituted or substituted with up to three of chloro, bromo, phenyl, methyl, phenoxy, nitro or methoxy. Suitably, $R^7$ is hydrogen.

U.S. Pat. No. 5,750,545 describes triazole derivatives, as agents for the prophylaxis and treatment of immune-related diseases, of formula (I) and formula (III):

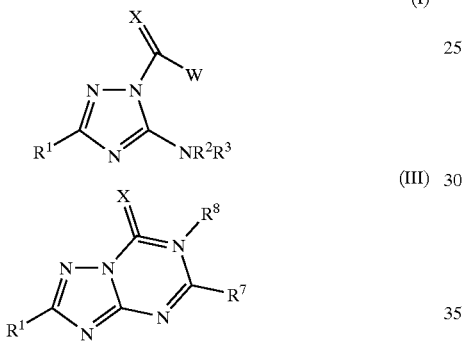

(I)

(III)

wherein

X is an oxygen atom or a sulfur atom; W is —NR$^4$R$^5$ or —SR$^6$; $R^1$ is a hydrogen atom, lower alkyl, —NR$^{10}$R$^{11}$, —N=R$^{13}$ or a group of the formula (II)

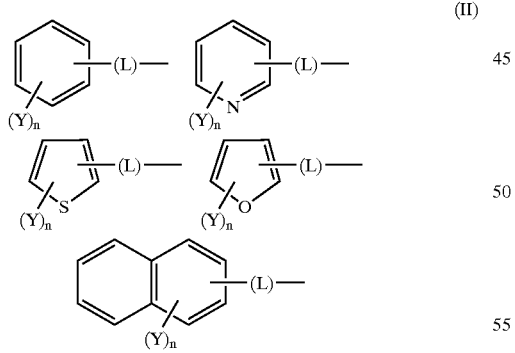

(II)

wherein

Y is a hydrogen atom, a lower alkyl, a lower alkoxy, a halogen, a cyano, a nitro, a lower alkyl substituted by halogen, —N$^{14}$R$^{15}$, a tetrazolyl, an optionally substituted phenyl, a hydroxy or a carboxyl, L is a direct bond, an oxygen atom, a sulfur atom, an alkylene, a vinylene or an ethynylene, and n is an integer of 1 to 3, provided that when n is 2 or 3, Y may be the same or different; and $R^2$ and $R^3$ are the same or different and each is a hydrogen atom or a lower alkyl; wherein $R^4$ and $R^5$ are the same or different and each is a hydrogen atom, an optionally substituted lower alkyl, cycloalkyl, a phenyl or —(CH$_2$)$_m$COOR$^{16}$, $R^{16}$ is a hydrogen atom or a lower alkyl, m is an integer of 1 to 6, $R^6$ is a lower alkyl, $R^{10}$ and $R^{11}$ are the same or different and each is a hydrogen atom, an optionally substituted benzoyl, an optionally substituted phenyl, a lower alkylcarbonyl or —COCOOR$^{17}$, $R^{17}$ is a lower alkyl, $R^{13}$ is an optionally substituted methylene, $R^{14}$ and $R^{15}$ are the same or different and each is a hydrogen atom, a lower alkyl, —COCOOR$^{17}$ or —CSNHR$^{18}$, and $R^{18}$ is a lower alkyl, or a pharmaceutically acceptable salt thereof.

Accordingly, it is an object of the present invention to provide substituted triazole diamine derivatives as selective kinase or dual-kinase inhibitors and a method of use thereof. It is an object of the present invention to provide substituted 1,2,4-triazole-3,5-diamine derivatives as selective kinase or dual-kinase inhibitors and a method of use for treating or ameliorating a selective kinase or dual-kinase mediated disorder.

SUMMARY OF THE INVENTION

The present invention provides a compound of Formula (I):

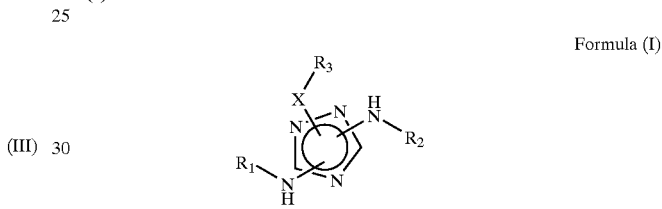

Formula (I)

wherein $R_1$ is selected from the group consisting of $C_{1-8}$alkyl, cycloalkyl, heterocyclyl, aryl and heteroaryl {wherein heterocyclyl is optionally substituted with 1 to 2 oxo substituents; and, wherein cycloalkyl, heterocyclyl, aryl and heteroaryl are substituted with a substituent selected from the group consisting of:

$C_{1-8}$alkyl (optionally substituted on a terminal carbon with a substituent selected from the group consisting of —C(O)H, —C(O)(C$_{1-8}$)alkyl, —CO$_2$H, —CO$_2$(C$_{1-8}$)alkyl, amino (substituted with two substituents independently selected from the group consisting of hydrogen and C$_{1-8}$alkyl), cyano, (halo)$_{1-3}$, hydroxy, nitro, cycloalkyl, heterocyclyl, aryl and heteroaryl), $C_{1-8}$alkoxy (optionally substituted on a terminal carbon with a substituent selected from the group consisting of (halo)$_{1-3}$ and hydroxy), —C(O)H, —C(O)(C$_{1-8}$)alkyl, —CO$_2$H, —CO$_2$(C$_{1-8}$)alkyl, amino (substituted with two substituents independently selected from the group consisting of hydrogen, C$_{1-8}$alkyl and —SO$_2$—(C$_{1-8}$)alkyl), —C(O)amino (wherein amino is substituted with two substituents independently selected from the group consisting of hydrogen and C$_{1-8}$alkyl), —SO$_2$— {substituted with one substituent selected from the group consisting of heterocyclyl and amino (wherein amino is substituted with two substituents independently selected from the group consisting of hydrogen, C$_{1-8}$alkyl, —C$_{1-8}$alkylamino (wherein amino is substituted with two substituents independently selected from the group consisting of hydrogen and C$_{1-8}$alkyl) and heteroaryl)}, cycloalkyl, heterocyclyl, aryl and heteroaryl {wherein cycloalkyl, heterocyclyl, aryl and heteroaryl are optionally substituted with 1 to 3 substituents independently selected from the group consisting of cyano, halo, hydroxy and nitro; wherein heterocyclyl is optionally substituted with 1 to 2 oxo substituents; and, wherein cycloalkyl, heterocyclyl, aryl and heteroaryl are optionally substituted with a substituent selected from the group consisting of $C_{1-8}$alkyl (wherein alkyl is optionally substituted on a terminal carbon with a substituent selected from the group consisting of amino (substituted with two substituents independently selected from the group consisting of hydrogen and $C_{1-8}$alkyl), cyano, (halo)$_{1-3}$, hydroxy and nitro), $C_{1-8}$alkoxy and amino (substituted with two substituents independently selected from the group consisting of hydrogen and $C_{1-8}$alkyl)}};

$R_2$ is selected from the group consisting of hydrogen, $C_{1-8}$alkyl, $C_{2-8}$alkenyl, $C_{2-8}$alkynyl and hydroxy($C_{1-8}$)alkyl;

X is selected from the group consisting of —C(O)—, —C(S)— and —SO$_2$—; and, $R_3$ is selected from the group consisting of:

$C_{1-8}$alkyl, $C_{2-8}$alkenyl, $C_{2-8}$alkynyl {wherein alkyl, alkenyl and alkynyl are optionally substituted on a terminal carbon with a substituent selected from the group consisting of —C(O)H, —C(O)($C_{1-8}$)alkyl, —CO$_2$H, —CO$_2$($C_{1-8}$)alkyl, amino (substituted with two substituents independently selected from the group consisting of hydrogen and $C_{1-8}$alkyl), cyano, (halo)$_{1-3}$, hydroxy, nitro, aryl and heteroaryl (wherein aryl and heteroaryl are optionally substituted with 1 to 5 substituents independently selected from the group consisting of $C_{1-8}$alkyl, cyano, halo, (halo)$_{1-3}$($C_{1-8}$)alkyl, (halo)$_{1-3}$($C_{1-8}$)alkoxy, hydroxy, hydroxy($C_{1-8}$)alkyl, hydroxy($C_{1-8}$)alkoxy and nitro)}, cycloalkyl, heterocyclyl, aryl, heteroaryl {wherein cycloalkyl, heterocyclyl, aryl and heteroaryl are optionally substituted with 1 to 3 substituents independently selected from the group consisting of cyano, halo, hydroxy and nitro; and, wherein cycloalkyl, heterocyclyl, aryl and heteroaryl are optionally substituted with 1 to 2 substituents independently selected from the group consisting of:

$C_{1-8}$alkyl, $C_{2-8}$alkenyl (wherein alkyl and alkenyl are optionally substituted on a terminal carbon with a substituent selected from the group consisting of —C(O)H, —C(O)($C_{1-8}$)alkyl, —CO$_2$H, —CO$_2$($C_{1-8}$) alkyl, amino (substituted with two substituents independently selected from the group consisting of hydrogen and $C_{1-8}$alkyl), cyano, (halo)$_{1-3}$, hydroxy, nitro, cycloalkyl, heterocyclyl, aryl and heteroaryl), —CH(OH)—($C_{1-8}$)alkyl, $C_{1-8}$alkoxy (optionally substituted on a terminal carbon with a substituent selected from the group consisting of (halo)$_{1-3}$ and hydroxy), —C(O)H, —C(O)($C_{1-8}$)alkyl, —CO$_2$H, —CO$_2$($C_{1-8}$) alkyl, amino (substituted with two substituents independently selected from the group consisting of hydrogen, $C_{1-8}$alkyl and —C(O)($C_{1-8}$)alkyl), —C(O)amino (wherein amino is substituted with two substituents independently selected from the group consisting of hydrogen and $C_{1-8}$alkyl), —SO$_2$— {substituted with one substituent selected from the group consisting of heterocyclyl and amino (wherein amino is substituted with two substituents independently selected from the group consisting of hydrogen, $C_{1-8}$alkyl and —$C_{1-8}$alkylamino (wherein amino is substituted with two substituents independently selected from the group consisting of hydrogen and $C_{1-8}$alkyl))}, —NH—SO$_2$—($C_{1-8}$)alkyl, cycloalkyl, heterocyclyl (optionally substituted with 1 to 2 oxo substituents), aryl and heteroaryl} and amino {substituted with two substituents independently selected from the group consisting of hydrogen, $C_{1-8}$alkyl, cycloalkyl, aryl and heteroaryl (wherein cycloalkyl, aryl and heteroaryl are optionally substituted with 1 to 5 substituents independently selected from the group consisting of $C_{1-8}$alkyl, cyano, halo, (halo)$_{1-3}$($C_{1-8}$)alkyl, (halo)$_{1-3}$($C_{1-8}$)alkoxy, hydroxy, hydroxy($C_{1-8}$)alkyl, hydroxy($C_{1-8}$)alkoxy and nitro)};

and pharmaceutically acceptable salts thereof.

An embodiment of the present invention is a method for treating or ameliorating a selective kinase or dual-kinase mediated disorder.

An embodiment of the present invention includes a method for producing the instant compounds and pharmaceutical compositions and medicaments thereof.

DETAILED DESCRIPTION OF THE INVENTION

Embodiments of the present invention include compounds of Formula (I) wherein, preferably, $R_1$ is selected from the group consisting of: $C_{1-4}$alkyl, cycloalkyl, heterocyclyl, aryl and heteroaryl (wherein cycloalkyl, heterocyclyl, aryl and heteroaryl are substituted with a substituent selected from the group consisting of:

$C_{1-4}$alkyl (optionally substituted on a terminal carbon with a substituent selected from the group consisting of —C(O)H, —C(O)($C_{1-4}$)alkyl, —CO$_2$H, —CO$_2$($C_{1-4}$) alkyl, amino (substituted with two substituents independently selected from the group consisting of hydrogen and $C_{1-4}$alkyl), cyano, (halo)$_{1-3}$, hydroxy, nitro, cycloalkyl, heterocyclyl, aryl and heteroaryl), $C_{1-4}$alkoxy (optionally substituted on a terminal carbon with a substituent selected from the group consisting of (halo)$_{1-3}$ and hydroxy), —C(O)H, —C(O)($C_{1-4}$)alkyl, —CO$_2$H, —CO$_2$($C_{1-4}$) alkyl, amino (substituted with two substituents independently selected from the group consisting of hydrogen, $C_{1-4}$alkyl and —SO$_2$—($C_{1-4}$)alkyl), —C(O)amino (wherein amino is substituted with two substituents independently selected from the group consisting of hydrogen and $C_{1-4}$alkyl), —SO$_2$— {substituted with one substituent selected from the group consisting of heterocyclyl and amino (wherein amino is substituted with two substituents independently selected from the group consisting of hydrogen, $C_{1-4}$alkyl, —$C_{1-4}$alkylamino (wherein amino is substituted with two substituents independently selected from the group consisting of hydrogen and $C_{1-4}$alkyl) and heteroaryl)}, cycloalkyl, heterocyclyl, aryl and heteroaryl {wherein cycloalkyl, heterocyclyl, aryl and heteroaryl are optionally substituted with 1 to 3 substituents independently selected from the group consisting of cyano, halo, hydroxy and nitro; wherein heterocyclyl is optionally substituted with 1 to 2 oxo substituents; and, wherein cycloalkyl, heterocyclyl, aryl and heteroaryl are optionally substituted with a substituent selected from the group consisting of $C_{1-4}$alkyl (wherein alkyl is optionally substituted on a terminal carbon with a substituent selected from the group consisting of amino (substituted with two substituents independently selected from the group consisting of hydrogen and $C_{1-4}$alkyl), cyano, (halo)$_{1-3}$, hydroxy and nitro), $C_{1-4}$alkoxy and amino (substituted with two substituents independently selected from the group consisting of hydrogen and $C_{1-4}$alkyl)}}.

More preferably, $R_1$ is selected from the group consisting of $C_{1-4}$alkyl and aryl {wherein aryl is substituted with a substituent selected from the group consisting of:

$C_{1-4}$alkyl (optionally substituted on a terminal carbon with a substituent selected from the group consisting of amino (substituted with two substituents independently selected from the group consisting of hydrogen and $C_{1-4}$alkyl), cyano, (halo)$_{1-3}$, hydroxy and nitro), $C_{1-4}$alkoxy, amino (substituted with two substituents independently selected from the group consisting of hydrogen, $C_{1-4}$alkyl and —SO$_2$—($C_{1-4}$)alkyl), —SO$_2$— {substituted with one substituent selected from the group consisting of heterocyclyl and amino (wherein amino is substituted with two substituents independently selected from the group consisting of hydrogen, $C_{1-4}$alkyl, —$C_{1-4}$alkylamino (wherein amino is substituted with two substituents independently selected from the group consisting of hydrogen and $C_{1-4}$alkyl) and heteroaryl)}, heterocyclyl (wherein heterocyclyl is optionally substituted with 1 to 2 substituents independently selected from the group consisting of $C_{1-4}$alkyl and oxo) and heteroaryl}.

Most preferably, $R_1$ is selected from the group consisting of $C_{1-4}$alkyl and phenyl {wherein phenyl is substituted with a substituent selected from the group consisting of: amino (substituted with two substituents independently selected from the group consisting of:

hydrogen, $C_{1-4}$alkyl and —SO$_2$—($C_{1-4}$)alkyl),

—SO$_2$— {substituted with one substituent selected from the group consisting of piperidinyl and amino (wherein amino is substituted with two substituents independently selected from the group consisting of hydrogen, $C_{1-4}$alkyl, —$C_{1-4}$alkylamino (wherein amino is substituted with two substituents independently selected from the group consisting of hydrogen and $C_{1-4}$alkyl) and pyridinyl)}, and piperazinyl (wherein piperazinyl is optionally substituted with 1 to 2 $C_{1-4}$alkyl substituents), imidazolidinyl, isothiazolidinyl (wherein imidazolidinyl and isothiazolidinyl are optionally substituted with 1 to 2 oxo substituents), imidazolyl and triazolyl}.

Embodiments of the present invention include compounds of Formula (I) wherein, preferably, $R_2$ is selected from the group consisting of hydrogen, $C_{1-4}$alkyl, $C_{2-4}$alkenyl, $C_{2-4}$alkynyl and hydroxy($C_{1-4}$)alkyl.

More preferably, $R_2$ is selected from the group consisting of hydrogen and $C_{1-4}$alkyl.

Most preferably, $R_2$ is hydrogen.

Embodiments of the present invention include compounds of Formula (I) wherein, preferably, X is selected from the group consisting of —C(O)—, —C(S)— and —SO$_2$—.

Embodiments of the present invention include compounds of Formula (I) wherein, preferably, $R_3$ is selected from the group consisting of:

$C_{1-4}$alkyl, $C_{2-4}$alkenyl, $C_{2-4}$alkynyl {wherein alkyl, alkenyl and alkynyl are optionally substituted on a terminal carbon with a substituent selected from the group consisting of —C(O)H, —C(O)($C_{1-4}$)alkyl, —CO$_2$H, —CO$_2$($C_{1-4}$)alkyl, amino (substituted with two substituents independently selected from the group consisting of hydrogen and $C_{1-4}$alkyl), cyano, (halo)$_{1-3}$, hydroxy, nitro, aryl and heteroaryl (wherein aryl and heteroaryl are optionally substituted with 1 to 5 substituents independently selected from the group consisting of $C_{1-4}$alkyl, cyano, halo, (halo)$_{1-3}$($C_{1-4}$)alkyl, (halo)$_{1-3}$($C_{1-4}$)alkoxy, hydroxy, hydroxy($C_{1-4}$)alkyl, hydroxy($C_{1-4}$)alkoxy and nitro)}, cycloalkyl, heterocyclyl, aryl, heteroaryl {wherein cycloalkyl, heterocyclyl, aryl and heteroaryl are optionally substituted with 1 to 3 substituents independently selected from the group consisting of cyano, halo, hydroxy and nitro; and, wherein cycloalkyl, heterocyclyl, aryl and heteroaryl are optionally substituted with 1 to 2 substituents independently selected from the group consisting of:

$C_{1-4}$alkyl, $C_{2-4}$alkenyl (wherein alkyl and alkenyl are optionally substituted on a terminal carbon with a substituent selected from the group consisting of —C(O)H, —C(O)($C_{1-4}$)alkyl, —CO$_2$H, —CO$_2$($C_{1-4}$)alkyl, amino (substituted with two substituents independently selected from the group consisting of hydrogen and $C_{1-4}$alkyl), cyano, (halo)$_{1-3}$, hydroxy, nitro, cycloalkyl, heterocyclyl, aryl and heteroaryl), —CH(OH)—($C_{1-4}$)alkyl, $C_{1-4}$alkoxy (optionally substituted on a terminal carbon with a substituent selected from the group consisting of (halo)$_{1-3}$ and hydroxy), —C(O)H, —C(O)($C_{1-4}$)alkyl, —CO$_2$H, —CO$_2$($C_{1-4}$)alkyl, amino (substituted with two substituents independently selected from the group consisting of hydrogen, $C_{1-4}$alkyl and —C(O)($C_{1-4}$)alkyl), —C(O)amino (wherein amino is substituted with two substituents independently selected from the group consisting of hydrogen and $C_{1-4}$alkyl), —SO$_2$— {substituted with one substituent selected from the group consisting of heterocyclyl and amino (wherein amino is substituted with two substituents independently selected from the group consisting of hydrogen, $C_{1-4}$alkyl and —$C_{1-4}$alkylamino (wherein amino is substituted with two substituents independently selected from the group consisting of hydrogen and $C_{1-4}$alkyl))}, —NH—SO$_2$—($C_{1-4}$)alkyl, cycloalkyl, heterocyclyl (optionally substituted with 1 to 2 oxo substituents), aryl and heteroaryl} and amino {substituted with two substituents independently selected from the group consisting of hydrogen, $C_{1-4}$alkyl, cycloalkyl, aryl and heteroaryl (wherein cycloalkyl, aryl and heteroaryl are optionally substituted with 1 to 5 substituents independently selected from the group consisting of $C_{1-4}$alkyl, cyano, halo, (halo)$_{1-3}$($C_{1-4}$)alkyl, (halo)$_{1-3}$($C_{1-4}$)alkoxy, hydroxy, hydroxy($C_{1-4}$)alkyl, hydroxy($C_{1-4}$)alkoxy and nitro)}.

More preferably, $R_3$ is selected from the group consisting of:

$C_{1-4}$alkyl, $C_{2-4}$alkenyl, $C_{2-4}$alkynyl {wherein alkyl, alkenyl and alkynyl are optionally substituted on a terminal carbon with a substituent selected from the group consisting of amino (substituted with two substituents independently selected from the group consisting of hydrogen and $C_{1-4}$alkyl), cyano, (halo)$_{1-3}$, hydroxy, nitro, aryl and heteroaryl (wherein aryl and heteroaryl are optionally substituted with 1 to 5 substituents independently selected from the group consisting of $C_{1-4}$alkyl, cyano, halo, (halo)$_{1-3}$($C_{1-4}$)alkyl, (halo)$_{1-3}$($C_{1-4}$)alkoxy, hydroxy, hydroxy($C_{1-4}$)alkyl, hydroxy($C_{1-4}$)alkoxy and nitro)}, cycloalkyl, heterocyclyl, aryl, heteroaryl {wherein cycloalkyl, aryl and heteroaryl are optionally substituted with 1 to 3 substituents independently selected from the group consisting of cyano, halo, hydroxy and nitro; and, wherein cycloalkyl, heterocyclyl, aryl and heteroaryl are optionally substituted with 1 to 2 substituents independently selected from the group consisting of:

$C_{1-4}$alkyl, $C_{2-4}$alkenyl (wherein alkyl and alkenyl are optionally substituted on a terminal carbon with a substituent selected from the group consisting of —$CO_2H$, —$CO_2(C_{1-4})$alkyl, amino (substituted with two substituents independently selected from the group consisting of hydrogen and $C_{1-4}$alkyl), cyano, (halo)$_{1-3}$, hydroxy, nitro, cycloalkyl, heterocyclyl, aryl and heteroaryl), —CH(OH)—($C_{1-4}$)alkyl, $C_{1-4}$alkoxy (optionally substituted on a terminal carbon with a substituent selected from the group consisting of (halo)$_{1-3}$ and hydroxy), —C(O)H, —C(O)($C_{1-4}$)alkyl, amino (substituted with two substituents independently selected from the group consisting of hydrogen, $C_{1-4}$alkyl and —C(O)($C_{1-4}$)alkyl), aryl and heteroaryl} and amino {substituted with two substituents independently selected from the group consisting of hydrogen, $C_{1-4}$alkyl and aryl (wherein aryl is optionally substituted with 1 to 5 substituents independently selected from the group consisting of $C_{1-4}$alkyl, cyano, halo, (halo)$_{1-3}$($C_{1-4}$)alkyl, (halo)$_{1-3}$($C_{1-4}$)alkoxy, hydroxy, hydroxy($C_{1-4}$)alkyl, hydroxy($C_{1-4}$)alkoxy and nitro)}.

Most preferably, $R_1$ is selected from the group consisting of:

$C_{1-4}$alkenyl, $C_{2-4}$alkenyl, $C_{2-4}$alkynyl {wherein alkyl, alkenyl and alkynyl are optionally substituted on a terminal carbon with a substituent selected from the group consisting of amino (substituted with two substituents independently selected from the group consisting of hydrogen and $C_{1-4}$alkyl), cyano, (halo)$_{1-3}$, hydroxy, nitro, phenyl and thienyl (wherein phenyl and thienyl are optionally substituted with 1 to 2 substituents independently selected from the group consisting of $C_{1-4}$alkyl, cyano, halo, hydroxy and nitro)}, cyclopentyl, cyclohexyl, cycloheptyl, benzo[b]thienyl, phenyl, furyl, thienyl, thiazolyl, isoxazolyl, thiadiazolyl, pyridinyl {wherein cyclohexyl and phenyl are optionally substituted with 1 to 3 substituents independently selected from the group consisting of cyano, halo, hydroxy and nitro; and, wherein cyclohexyl and phenyl are optionally substituted with 1 to 2 substituents independently selected from the group consisting of:

$C_{1-4}$alkyl (wherein alkyl is optionally substituted on a terminal carbon with a substituent selected from the group consisting of amino (substituted with two substituents independently selected from the group consisting of hydrogen and $C_{1-4}$alkyl), cyano, (halo)$_{1-3}$, hydroxy and nitro), —CH(OH)—($C_{1-4}$)alkyl, $C_{1-4}$alkoxy, amino (substituted with two substituents independently selected from the group consisting of hydrogen and $C_{1-4}$alkyl), and wherein thienyl and thiazolyl are optionally substituted with 1 to 3 substituents independently selected from the group consisting of cyano, halo, hydroxy and nitro; and, wherein thienyl and thiazolyl are optionally substituted with 1 to 2 substituents independently selected from the group consisting of:

$C_{1-4}$alkyl (wherein alkyl is optionally substituted on a terminal carbon with a substituent selected from the group consisting of —$CO_2H$, —$CO_2(C_{1-4})$alkyl, amino (substituted with two substituents independently selected from the group consisting of hydrogen and $C_{1-4}$alkyl), cyano, (halo)$_{1-3}$, hydroxy and nitro), $C_{1-4}$alkoxy, —C(O)($C_{1-4}$)alkyl, amino (substituted with two substituents independently selected from the group consisting of: hydrogen, $C_{1-4}$alkyl and —C(O)($C_{1-4}$)alkyl), pyrrolyl and pyridinyl;

and, wherein thiadiazolyl is optionally substituted with one substituent selected from the group consisting of $C_{1-4}$alkyl (wherein alkyl is optionally substituted on a terminal carbon with a substituent selected from the group consisting of:

amino (substituted with two substituents independently selected from the group consisting of hydrogen and $C_{1-4}$alkyl), cyano, (halo)$_{1-3}$, hydroxy and nitro), $C_{1-4}$alkoxy, amino (substituted with two substituents independently selected from the group consisting of hydrogen and $C_{1-4}$alkyl), cyano, halo, hydroxy and nitro} and amino {substituted with two substituents independently selected from the group consisting of hydrogen, $C_{1-4}$alkyl and phenyl (wherein phenyl is optionally substituted with 1 to 5 substituents independently selected from the group consisting of $C_{1-4}$alkyl, cyano, halo, hydroxy and nitro)}.

Embodiments of the present invention include compounds of Formula (I) selected from a compound of Formula (Ia):

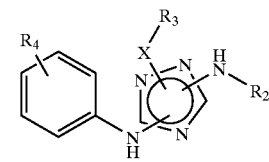

Formula (Ia)

wherein $R_4$ is selected from the group consisting of:

$C_{1-8}$alkyl {optionally substituted on a terminal carbon with a substituent selected from the group consisting of —C(O)H, —C(O)($C_{1-8}$)alkyl, —$CO_2H$, —$CO_2(C_{1-8})$alkyl, amino (substituted with two substituents independently selected from the group consisting of hydrogen and $C_{1-8}$alkyl), cyano, (halo)$_{1-3}$, hydroxy, nitro, cycloalkyl, heterocyclyl, aryl and heteroaryl}, $C_{1-8}$alkoxy (optionally substituted on a terminal carbon with a substituent selected from the group consisting of (halo)$_{1-3}$ and hydroxy), —C(O)H, —C(O)($C_{1-8}$)alkyl, —$CO_2H$, —$CO_2(C_{1-8})$alkyl, amino (substituted with two substituents independently selected from the group consisting of hydrogen, $C_{1-8}$alkyl and —$SO_2$—($C_{1-8})$alkyl), —C(O)amino (wherein amino is substituted with two substituents independently selected from the group consisting of hydrogen and $C_{1-8}$alkyl), —$SO_2$— {substituted with one substituent selected from the group consisting of heterocyclyl and amino (wherein amino is substituted with two substituents independently selected from the group consisting of hydrogen, $C_{1-8}$alkyl, —$C_{1-8}$alkylamino (wherein amino is substituted with two substituents independently selected from the group consisting of hydrogen and $C_{1-8}$alkyl) and heteroaryl)}, cycloalkyl, heterocyclyl, aryl and heteroaryl {wherein cycloalkyl, heterocyclyl, aryl and heteroaryl are optionally substituted with 1 to 5 substituents independently selected from the group consisting of $C_{1-8}$alkyl (wherein alkyl is optionally substituted on a terminal carbon with a substituent selected from the group consisting of amino (substituted with two substituents independently selected from the group consisting of hydrogen and $C_{1-8}$alkyl), cyano, (halo)$_{1-3}$, hydroxy and nitro), $C_{1-8}$alkoxy, amino (substituted with two substituents independently selected from the group consisting of hydrogen and $C_{1-8}$alkyl), cyano, halo, hydroxy and nitro; and, wherein heterocyclyl is optionally substituted with 1 to 2 oxo substituents};

$R_2$ is selected from the group consisting of hydrogen, $C_{1-8}$alkyl, $C_{2-8}$alkenyl, $C_{2-8}$alkynyl and hydroxy($C_{1-8}$)alkyl;

X is selected from the group consisting of —C(O)—, —C(S)— and —SO$_2$—; and, $R_3$ is selected from the group consisting of:

$C_{1-8}$alkyl, $C_{2-8}$alkenyl, $C_{2-8}$alkynyl {wherein alkyl, alkenyl and alkynyl are optionally substituted on a terminal carbon with a substituent selected from the group consisting of —C(O)H, —C(O)($C_{1-8}$)alkyl, —CO$_2$H, —CO$_2$($C_{1-8}$)alkyl, amino (substituted with two substituents independently selected from the group consisting of hydrogen and $C_{1-8}$alkyl), cyano, (halo)$_{1-3}$, hydroxy, nitro, aryl and heteroaryl (wherein aryl and heteroaryl are optionally substituted with 1 to 5 substituents independently selected from the group consisting of $C_{1-8}$alkyl, cyano, halo, (halo)$_{1-3}$($C_{1-8}$)alkyl, (halo)$_{1-3}$($C_{1-8}$)alkoxy, hydroxy, hydroxy($C_{1-8}$)alkyl, hydroxy($C_{1-8}$)alkoxy and nitro)}, cycloalkyl, heterocyclyl, aryl, heteroaryl {wherein cycloalkyl, heterocyclyl, aryl and heteroaryl are optionally substituted with 1 to 3 substituents independently selected from the group consisting of cyano, halo, hydroxy and nitro; and, wherein cycloalkyl, heterocyclyl, aryl and heteroaryl are optionally substituted with 1 to 2 substituents independently selected from the group consisting of:

$C_{1-8}$ alkyl, $C_{2-8}$alkenyl (wherein alkyl and alkenyl are optionally substituted on a terminal carbon with a substituent selected from the group consisting of —C(O)H, —C(O)($C_{1-8}$)alkyl, —CO$_2$H, —CO$_2$($C_{1-8}$)alkyl, amino (substituted with two substituents independently selected from the group consisting of hydrogen and $C_{1-8}$alkyl), cyano, (halo)$_{1-3}$, hydroxy, nitro, cycloalkyl, heterocyclyl, aryl and heteroaryl), —CH(OH)—($C_{1-8}$)alkyl, $C_{1-8}$alkoxy (optionally substituted on a terminal carbon with a substituent selected from the group consisting of (halo)$_{1-3}$ and hydroxy), —C(O)H, —C(O)($C_{1-8}$)alkyl, —CO$_2$H, —CO$_2$($C_{1-8}$)alkyl, amino (substituted with two substituents independently selected from the group consisting of hydrogen, $C_{1-8}$alkyl and —C(O)($C_{1-8}$)alkyl), —C(O)amino (wherein amino is substituted with two substituents independently selected from the group consisting of hydrogen and $C_{1-8}$alkyl), —SO$_2$— {substituted with one substituent selected from the group consisting of heterocyclyl and amino (wherein amino is substituted with two substituents independently selected from the group consisting of hydrogen, $C_{1-8}$alkyl, —$C_{1-8}$alkylamino (wherein amino is substituted with two substituents independently selected from the group consisting of hydrogen and $C_{1-8}$alkyl)) }, —NH—SO$_2$—($C_{1-8}$)alkyl, cycloalkyl, heterocyclyl (optionally substituted with 1 to 2 oxo substituents), aryl and heteroaryl} and amino {substituted with two substituents independently selected from the group consisting of hydrogen, $C_{1-8}$alkyl, cycloalkyl, aryl and heteroaryl (wherein cycloalkyl, aryl and heteroaryl are optionally substituted with 1 to 5 substituents independently selected from the group consisting of $C_{1-8}$alkyl, cyano, halo, (halo)$_{1-3}$($C_{1-8}$)alkyl, (halo)$_{1-3}$($C_{1-8}$)alkoxy, hydroxy, hydroxy($C_{1-8}$)alkyl, hydroxy($C_{1-8}$)alkoxy and nitro)};

and pharmaceutically acceptable salts thereof.

Embodiments of the present invention include compounds of Formula (I) selected from a compound of Formula (Ib):

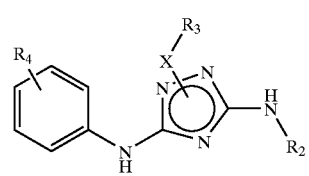

Formula (Ib)

wherein $R_4$ is selected from the group consisting of:

$C_{1-8}$alkyl {optionally substituted on a terminal carbon with a substituent selected from the group consisting of —C(O)H, —C(O)($C_{1-8}$)alkyl, —CO$_2$H, —CO$_2$($C_{1-8}$)alkyl, amino (substituted with two substituents independently selected from the group consisting of hydrogen and $C_{1-8}$alkyl), cyano, (halo)$_{1-3}$, hydroxy, nitro, cycloalkyl, heterocyclyl, aryl and heteroaryl}, $C_{1-8}$alkoxy (optionally substituted on a terminal carbon with a substituent selected from the group consisting of (halo)$_{1-3}$ and hydroxy), —C(O)H, —C(O)($C_{1-8}$)alkyl, —CO$_2$H, —CO$_2$($C_{1-8}$)alkyl, amino (substituted with two substituents independently selected from the group consisting of hydrogen, $C_{1-8}$alkyl and —SO$_2$—($C_{1-8}$)alkyl), —C(O)amino (wherein amino is substituted with two substituents independently selected from the group consisting of hydrogen and $C_{1-8}$alkyl), —SO$_2$— {substituted with one substituent selected from the group consisting of heterocyclyl and amino (wherein amino is substituted with two substituents independently selected from the group consisting of hydrogen, $C_{1-8}$alkyl, —$C_{1-8}$alkylamino (wherein amino is substituted with two substituents independently selected from the group consisting of hydrogen and $C_{1-8}$alkyl) and heteroaryl)}, cycloalkyl, heterocyclyl, aryl and heteroaryl {wherein cycloalkyl, heterocyclyl, aryl and heteroaryl are optionally substituted with 1 to 5 substituents independently selected from the group consisting of $C_{1-8}$alkyl (wherein alkyl is optionally substituted on a terminal carbon with a substituent selected from the group consisting of amino (substituted with two substituents independently selected from the group consisting of hydrogen and $C_{1-8}$alkyl), cyano, (halo)$_{1-3}$, hydroxy and nitro), $C_{1-8}$alkoxy, amino (substituted with two substituents independently selected from the group consisting of hydrogen and $C_{1-8}$alkyl), cyano, halo, hydroxy and nitro; and, wherein heterocyclyl is optionally substituted with 1 to 2 oxo substituents};

R$_2$ is selected from the group consisting of hydrogen, C$_{1-8}$alkyl, C$_{2-8}$alkenyl, C$_{2-8}$alkynyl and hydroxy(C$_{1-8}$)alkyl;

X is selected from the group consisting of —C(O)—, —C(S)— and —SO$_2$—; and,

R$_3$ is selected from the group consisting of:

C$_{1-8}$alkyl, C$_{2-8}$alkenyl, C$_{2-8}$alkynyl {wherein alkyl, alkenyl and alkynyl are optionally substituted on a terminal carbon with a substituent selected from the group consisting of —C(O)H, —C(O)(C$_{1-8}$)alkyl, —CO$_2$H, —CO$_2$(C$_{1-8}$)alkyl, amino (substituted with two substituents independently selected from the group consisting of hydrogen and C$_{1-8}$alkyl), cyano, (halo)$_{1-3}$, hydroxy, nitro, aryl and heteroaryl (wherein aryl and heteroaryl are optionally substituted with 1 to 5 substituents independently selected from the group consisting of C$_{1-8}$alkyl, cyano, halo, (halo)$_{1-3}$(C$_{1-8}$)alkyl, (halo)$_{1-3}$(C$_{1-8}$)alkoxy, hydroxy, hydroxy(C$_{1-8}$)alkyl, hydroxy(C$_{1-8}$)alkoxy and nitro)}, cycloalkyl, heterocyclyl, aryl, heteroaryl {wherein cycloalkyl, heterocyclyl, aryl and heteroaryl are optionally substituted with 1 to 3 substituents independently selected from the group consisting of cyano, halo, hydroxy and nitro; and, wherein cycloalkyl, heterocyclyl, aryl and heteroaryl are optionally substituted with 1 to 2 substituents independently selected from the group consisting of:

C$_{1-8}$alkyl, C$_{2-8}$alkenyl (wherein alkyl and alkenyl are optionally substituted on a terminal carbon with a substituent selected from the group consisting of —C(O)H, —C(O)(C$_{1-8}$)alkyl, —CO$_2$H, —CO$_2$(C$_{1-8}$)alkyl, amino (substituted with two substituents independently selected from the group consisting of hydrogen and C$_{1-8}$alkyl), cyano, (halo)$_{1-3}$, hydroxy, nitro, cycloalkyl, heterocyclyl, aryl and heteroaryl), —CH(OH)—(C$_{1-8}$)alkyl, C$_{1-8}$alkoxy (optionally substituted on a terminal carbon with a substituent selected from the group consisting of (halo)$_{1-3}$ and hydroxy), —C(O)H, —C(O)(C$_{1-8}$)alkyl, —CO$_2$H, —CO$_2$(C$_{1-8}$)alkyl, amino (substituted with two substituents independently selected from the group consisting of hydrogen, C$_{1-8}$alkyl and —C(O)(C$_{1-8}$)alkyl), —C(O)amino (wherein amino is substituted with two substituents independently selected from the group consisting of hydrogen and C$_{1-8}$alkyl), —SO$_2$— {substituted with one substituent selected from the group consisting of heterocyclyl and amino (wherein amino is substituted with two substituents independently selected from the group consisting of hydrogen, C$_{1-8}$alkyl and —C$_{1-8}$alkylamino (wherein amino is substituted with two substituents independently selected from the group consisting of hydrogen and C$_{1-8}$alkyl))}, —NH—SO$_2$—(C$_{1-8}$)alkyl, cycloalkyl, heterocyclyl (optionally substituted with 1 to 2 oxo substituents), aryl and heteroaryl} and amino {substituted with two substituents independently selected from the group consisting of hydrogen, C$_{1-8}$alkyl, cycloalkyl, aryl and heteroaryl (wherein cycloalkyl, aryl and heteroaryl are optionally substituted with 1 to 5 substituents independently selected from the group consisting of C$_{1-8}$alkyl, cyano, halo, (halo)$_{1-3}$(C$_{1-8}$)alkyl, (halo)$_{1-3}$(C$_{1-8}$)alkoxy, hydroxy, hydroxy(C$_{1-8}$)alkyl, hydroxy(C$_{1-8}$)alkoxy and nitro)};

and pharmaceutically acceptable salts thereof.

Embodiments of the present invention include compounds of Formula (I) selected from a compound of Formula (Ic):

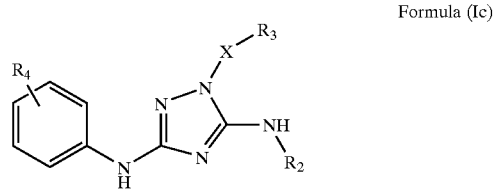

Formula (Ic)

wherein

R$_4$ is selected from the group consisting of:

C$_{1-8}$alkyl {optionally substituted on a terminal carbon with a substituent selected from the group consisting of —C(O)H, —C(O)(C$_{1-8}$)alkyl, —CO$_2$H, —CO$_2$(C$_{1-8}$)alkyl, amino (substituted with two substituents independently selected from the group consisting of hydrogen and C$_{1-8}$alkyl), cyano, (halo)$_{1-3}$, hydroxy, nitro, cycloalkyl, heterocyclyl, aryl and heteroaryl}, C$_{1-8}$alkoxy (optionally substituted on a terminal carbon with a substituent selected from the group consisting of (halo)$_{1-3}$ and hydroxy), —C(O)H, —C(O)(C$_{1-8}$)alkyl, —CO$_2$H, —CO$_2$(C$_{1-8}$)alkyl, amino (substituted with two substituents independently selected from the group consisting of hydrogen, C$_{1-8}$alkyl and —SO$_2$—(C$_{1-8}$)alkyl), —C(O)amino (wherein amino is substituted with two substituents independently selected from the group consisting of hydrogen and C$_{1-8}$alkyl), —SO$_2$— {substituted with one substituent selected from the group consisting of heterocyclyl and amino (wherein amino is substituted with two substituents independently selected from the group consisting of hydrogen, C$_{1-8}$alkyl, —C$_{1-8}$alkylamino (wherein amino is substituted with two substituents independently selected from the group consisting of hydrogen and C$_{1-8}$alkyl) and heteroaryl)}, cycloalkyl, heterocyclyl, aryl and heteroaryl {wherein cycloalkyl, heterocyclyl, aryl and heteroaryl are optionally substituted with 1 to 5 substituents independently selected from the group consisting of C$_{1-8}$alkyl (wherein alkyl is optionally substituted on a terminal carbon with a substituent selected from the group consisting of amino (substituted with two substituents independently selected from the group consisting of hydrogen and C$_{1-8}$alkyl), cyano, (halo)$_{1-3}$, hydroxy and nitro), C$_{1-8}$alkoxy, amino (substituted with two substituents independently selected from the group consisting of hydrogen and C$_{1-8}$alkyl), cyano, halo, hydroxy and nitro; and, wherein heterocyclyl is optionally substituted with 1 to 2 oxo substituents};

R$_2$ is selected from the group consisting of hydrogen, C$_{1-8}$alkyl, C$_{2-8}$alkenyl, C$_{2-8}$alkynyl and hydroxy(C$_{1-8}$)alkyl;

X is selected from the group consisting of —C(O)—, —C(S)— and —SO$_2$—; and,

R$_3$ is selected from the group consisting of:

C$_{1-8}$alkyl, C$_{2-8}$alkenyl, C$_{2-8}$alkynyl {wherein alkyl, alkenyl and alkynyl are optionally substituted on a terminal carbon with a substituent selected from the group consisting of —C(O)H, —C(O)(C$_{1-8}$)alkyl, —CO$_2$H, —CO$_2$(C$_{1-8}$)alkyl, amino (substituted with two substituents independently selected from the group consisting of hydrogen and C$_{1-8}$alkyl), cyano, (halo)$_{1-3}$, hydroxy, nitro, aryl and heteroaryl (wherein aryl and heteroaryl are optionally substituted with 1 to 5 substituents independently selected from the group consisting of $C_{1-8}$alkyl, cyano, halo, (halo)$_{1-3}$($C_{1-8}$)alkyl, (halo)$_{1-3}$($C_{1-8}$)alkoxy, hydroxy, hydroxy($C_{1-8}$)alkyl, hydroxy($C_{1-8}$)alkoxy and nitro)}, cycloalkyl, heterocyclyl, aryl, heteroaryl {wherein cycloalkyl, heterocyclyl, aryl and heteroaryl are optionally substituted with 1 to 3 substituents independently selected from the group consisting of cyano, halo, hydroxy and nitro; and, wherein cycloalkyl, heterocyclyl, aryl and heteroaryl are optionally substituted with 1 to 2 substituents independently selected from the group consisting of:

$C_{1-8}$alkyl, $C_{2-8}$alkenyl (wherein alkyl and alkenyl are optionally substituted on a terminal carbon with a substituent selected from the group consisting of —C(O)H, —C(O)($C_{1-8}$)alkyl, —CO$_2$H, —CO$_2$($C_{1-8}$)alkyl, amino (substituted with two substituents independently selected from the group consisting of hydrogen and $C_{1-8}$alkyl), cyano, (halo)$_{1-3}$, hydroxy, nitro, cycloalkyl, heterocyclyl, aryl and heteroaryl), —CH(OH)—($C_{1-8}$)alkyl, $C_{1-8}$alkoxy (optionally substituted on a terminal carbon with a substituent selected from the group consisting of (halo)$_{1-3}$ and hydroxy), —C(O)H, —C(O)($C_{1-8}$)alkyl, —CO$_2$H, —CO$_2$($C_{1-8}$)alkyl, amino (substituted with two substituents independently selected from the group consisting of hydrogen, $C_{1-8}$alkyl and —C(O)($C_{1-8}$)alkyl), —C(O)amino (wherein amino is substituted with two substituents independently selected from the group consisting of hydrogen and $C_{1-8}$alkyl), —SO$_2$— {substituted with one substituent selected from the group consisting of heterocyclyl and amino (wherein amino is substituted with two substituents independently selected from the group consisting of hydrogen, $C_{1-8}$alkyl and —$C_{1-8}$alkylamino (wherein amino is substituted with two substituents independently selected from the group consisting of hydrogen and $C_{1-8}$alkyl))}, —NH—SO$_2$—($C_{1-8}$)alkyl, cycloalkyl, heterocyclyl (optionally substituted with 1 to 2 oxo substituents), aryl and heteroaryl} and amino {substituted with two substituents independently selected from the group consisting of hydrogen, $C_{1-8}$alkyl, cycloalkyl, aryl and heteroaryl (wherein cycloalkyl, aryl and heteroaryl are optionally substituted with 1 to 5 substituents independently selected from the group consisting of $C_{1-8}$alkyl, cyano, halo, (halo)$_{1-3}$($C_{1-8}$)alkyl, (halo)$_{1-3}$($C_{1-8}$)alkoxy, hydroxy, hydroxy($C_{1-8}$)alkyl, hydroxy($C_{1-8}$)alkoxy and nitro)};

and pharmaceutically acceptable salts thereof.

Embodiments of the present invention include compounds of Formula (Ic) wherein, preferably, R$_4$ is selected from the group consisting of:

amino (substituted with two substituents independently selected from the group consisting of hydrogen, $C_{1-4}$alkyl and —SO$_2$—($C_{1-4}$)alkyl), —SO$_2$— {substituted with one substituent selected from the group consisting of heterocyclyl and amino (wherein amino is substituted with two substituents independently selected from the group consisting of hydrogen, $C_{1-4}$alkyl, —$C_{1-4}$alkylamino (wherein amino is substituted with two substituents independently selected from the group consisting of hydrogen and $C_{1-4}$alkyl) and heteroaryl)}, heterocyclyl (wherein heterocyclyl is optionally substituted with 1 to 2 substituents independently selected from the group consisting of $C_{1-4}$alkyl and oxo) and heteroaryl.

Embodiments of the present invention include compounds of Formula (I) selected from a compound of Formula (Id):

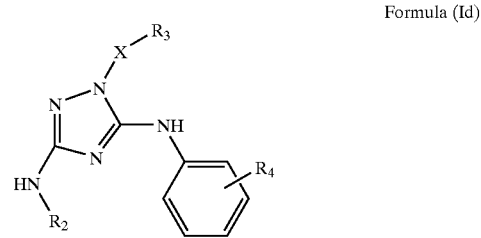

Formula (Id)

wherein

R$_4$ is selected from the group consisting of:

$C_{1-8}$alkyl {optionally substituted on a terminal carbon with a substituent selected from the group consisting of —C(O)H, —C(O)($C_{1-8}$)alkyl, —CO$_2$H, —CO$_2$($C_{1-8}$)alkyl, amino (substituted with two substituents independently selected from the group consisting of hydrogen and $C_{1-8}$alkyl), cyano, (halo)$_{1-3}$, hydroxy, nitro, cycloalkyl, heterocyclyl, aryl and heteroaryl}, $C_{1-8}$alkoxy (optionally substituted on a terminal carbon with a substituent selected from the group consisting of (halo)$_{1-3}$ and hydroxy), —C(O)H, —C(O)($C_{1-8}$)alkyl, —C$_2$H, —CO$_2$($C_{1-8}$)alkyl, amino (substituted with two substituents independently selected from the group consisting of hydrogen, $C_{1-8}$alkyl and —SO$_2$—($C_{1-8}$)alkyl), —C(O)amino (wherein amino is substituted with two substituents independently selected from the group consisting of hydrogen and $C_{1-8}$alkyl), —SO$_2$— {substituted with one substituent selected from the group consisting of heterocyclyl and amino (wherein amino is substituted with two substituents independently selected from the group consisting of hydrogen, $C_{1-8}$alkyl, —$C_{1-8}$alkylamino (wherein amino is substituted with two substituents independently selected from the group consisting of hydrogen and $C_{1-8}$alkyl) and heteroaryl)}, cycloalkyl, heterocyclyl, aryl and heteroaryl {wherein cycloalkyl, heterocyclyl, aryl and heteroaryl are optionally substituted with 1 to 5 substituents independently selected from the group consisting of $C_{1-8}$alkyl (wherein alkyl is optionally substituted on a terminal carbon with a substituent selected from the group consisting of amino (substituted with two substituents independently selected from the group consisting of hydrogen and $C_{1-8}$alkyl), cyano, (halo)$_{1-3}$, hydroxy and nitro), $C_{1-8}$alkoxy, amino (substituted with two substituents independently selected from the group consisting of hydrogen and $C_{1-8}$alkyl), cyano, halo, hydroxy and nitro; and, wherein heterocyclyl is optionally substituted with 1 to 2 oxo substituents};

R$_2$ is selected from the group consisting of hydrogen, $C_{1-8}$alkyl, $C_{2-8}$alkenyl, $C_{2-8}$alkynyl and hydroxy($C_{1-8}$)alkyl;

X is selected from the group consisting of —C(O)—, —C(S)— and —SO$_2$—; and,

R$_3$ is selected from the group consisting of:

$C_{1-8}$alkyl, $C_{2-8}$alkenyl, $C_{2-8}$alkynyl {wherein alkyl, alkenyl and alkynyl are optionally substituted on a terminal carbon with a substituent selected from the group consisting of —C(O)H, —C(O)(C$_{1-8}$)alkyl, —CO$_2$H, —CO$_2$(C$_{1-8}$)alkyl, amino (substituted with two substituents independently selected from the group consisting of hydrogen and C$_{1-8}$alkyl), cyano, (halo)$_{1-3}$, hydroxy, nitro, aryl and heteroaryl (wherein aryl and heteroaryl are optionally substituted with 1 to 5 substituents independently selected from the group consisting of C$_{1-8}$alkyl, cyano, halo, (halo)$_{1-3}$(C$_{1-8}$)alkyl, (halo)$_{1-3}$(C$_{1-8}$)alkoxy, hydroxy, hydroxy(C$_{1-8}$)alkyl, hydroxy(C$_{1-8}$)alkoxy and nitro)}, cycloalkyl, heterocyclyl, aryl, heteroaryl {wherein cycloalkyl, heterocyclyl, aryl and heteroaryl are optionally substituted with 1 to 3 substituents independently selected from the group consisting of cyano, halo, hydroxy and nitro; and, wherein cycloalkyl, heterocyclyl, aryl and heteroaryl are optionally substituted with 1 to 2 substituents independently selected from the group consisting of:

C$_{1-8}$alkyl, C$_{2-8}$alkenyl (wherein alkyl and alkenyl are optionally substituted on a terminal carbon with a substituent selected from the group consisting of —C(O)H, —C(O)(C$_{1-8}$)alkyl, —CO$_2$H, —CO$_2$(C$_{1-8}$) alkyl, amino (substituted with two substituents independently selected from the group consisting of hydrogen and C$_{1-8}$alkyl), cyano, (halo)$_{1-3}$, hydroxy, nitro, cycloalkyl, heterocyclyl, aryl and heteroaryl), —CH(OH)—(C$_{1-8}$)alkyl, C$_{1-8}$alkoxy (optionally substituted on a terminal carbon with a substituent selected from the group consisting of (halo)$_{1-3}$ and hydroxy), —C(O)H, —C(O)(C$_{1-8}$)alkyl, —CO$_2$H, —CO$_2$(C$_{1-8}$) alkyl, amino (substituted with two substituents independently selected from the group consisting of hydrogen, C$_{1-8}$alkyl and —C(O)(C$_{1-8}$)alkyl), —C(O)amino (wherein amino is substituted with two substituents independently selected from the group consisting of hydrogen and C$_{1-8}$alkyl), SO$_2$— {substituted with one substituent selected from the group consisting of heterocyclyl and amino (wherein amino is substituted with two substituents independently selected from the group consisting of hydrogen, C$_{1-8}$alkyl and —C$_{1-8}$alkylamino (wherein amino is substituted with two substituents independently selected from the group consisting of hydrogen and C$_{1-8}$alkyl))}, —NH—SO$_2$—(C$_{1-8}$)alkyl, cycloalkyl, heterocyclyl (optionally substituted with 1 to 2 oxo substituents), aryl and heteroaryl} and amino {substituted with two substituents independently selected from the group consisting of hydrogen, C$_{1-8}$alkyl, cycloalkyl, aryl and heteroaryl (wherein cycloalkyl, aryl and heteroaryl are optionally substituted with 1 to 5 substituents independently selected from the group consisting of C$_{1-8}$alkyl, cyano, halo, (halo)$_{1-3}$(C$_{1-8}$)alkyl, (halo)$_{1-3}$(C$_{1-8}$)alkoxy, hydroxy, hydroxy(C$_{1-8}$)alkyl, hydroxy(C$_{1-8}$)alkoxy and nitro)};

and pharmaceutically acceptable salts thereof.

Embodiments of the present invention include compounds of Formula (I) selected from a compound of Formula (Ie):

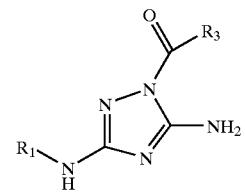

Formula (Ie)

wherein

R$_1$ is selected from the group consisting of C$_{1-8}$alkyl, cycloalkyl, heterocyclyl, aryl and heteroaryl {wherein heterocyclyl is optionally substituted with 1 to 2 oxo substituents; and, wherein cycloalkyl, heterocyclyl, aryl and heteroaryl are substituted with a substituent selected from the group consisting of:

C$_{1-8}$alkyl (optionally substituted on a terminal carbon with a substituent selected from the group consisting of —C(O)H, —C(O)(C$_{1-8}$)alkyl, —CO$_2$H, —CO$_2$(C$_{1-8}$) alkyl, amino (substituted with two substituents independently selected from the group consisting of hydrogen and C$_{1-8}$alkyl), cyano, (halo)$_{1-3}$, hydroxy, nitro, cycloalkyl, heterocyclyl, aryl and heteroaryl), C$_{1-8}$alkoxy (optionally substituted on a terminal carbon with a substituent selected from the group consisting of (halo)$_{1-3}$ and hydroxy), —C(O)H, —C(O)(C$_{1-8}$)alkyl, —CO$_2$H, —CO$_2$(C$_{1-8}$) alkyl, amino (substituted with two substituents independently selected from the group consisting of hydrogen, C$_{1-8}$alkyl and —SO$_2$—(C$_{1-8}$)alkyl), —C(O)amino (wherein amino is substituted with two substituents independently selected from the group consisting of hydrogen and C$_{1-8}$alkyl), —SO$_2$— {substituted with one substituent selected from the group consisting of heterocyclyl and amino (wherein amino is substituted with two substituents independently selected from the group consisting of hydrogen, C$_{1-8}$alkyl, —C$_{1-8}$alkylamino (wherein amino is substituted with two substituents independently selected from the group consisting of hydrogen and C$_{1-8}$alkyl) and heteroaryl)}, cycloalkyl, heterocyclyl, aryl and heteroaryl {wherein cycloalkyl, heterocyclyl, aryl and heteroaryl are optionally substituted with 1 to 3 substituents independently selected from the group consisting of cyano, halo, hydroxy and nitro; wherein heterocyclyl is optionally substituted with 1 to 2 oxo substituents; and, wherein cycloalkyl, heterocyclyl, aryl and heteroaryl are optionally substituted with a substituent selected from the group consisting of C$_{1-8}$alkyl (wherein alkyl is optionally substituted on a terminal carbon with a substituent selected from the group consisting of amino (substituted with two substituents independently selected from the group consisting of hydrogen and C$_{1-8}$alkyl), cyano, (halo)$_{1-3}$, hydroxy and nitro), C$_{1-8}$alkoxy and amino (substituted with two substituents independently selected from the group consisting of hydrogen and C$_{1-8}$alkyl)}}; and, R$_3$ is selected from the group consisting of:

C$_{1-8}$alkyl, C$_{2-8}$alkenyl, C$_{2-8}$alkynyl {wherein alkyl, alkenyl and alkynyl are optionally substituted on a terminal carbon with a substituent selected from the group consisting of —C(O)H, —C(O)(C$_{1-8}$)alkyl, —CO$_2$H, —CO$_2$ (C$_{1-8}$)alkyl, amino (substituted with two substituents independently selected from the group consisting of hydrogen and $C_{1-8}$alkyl), cyano, (halo)$_{1-3}$, hydroxy, nitro, aryl and heteroaryl (wherein aryl and heteroaryl are optionally substituted with 1 to 5 substituents independently selected from the group consisting of $C_{1-8}$alkyl, cyano, halo, (halo)$_{1-3}$($C_{1-8}$)alkyl, (halo)$_{1-3}$($C_{1-8}$)alkoxy, hydroxy, hydroxy($C_{1-8}$)alkyl, hydroxy($C_{1-8}$)alkoxy and nitro)}, cycloalkyl, heterocyclyl, aryl, heteroaryl {wherein cycloalkyl, heterocyclyl, aryl and heteroaryl are optionally substituted with 1 to 3 substituents independently selected from the group consisting of cyano, halo, hydroxy and nitro; and, wherein cycloalkyl, heterocyclyl, aryl and heteroaryl are optionally substituted with 1 to 2 substituents independently selected from the group consisting of:

$C_{1-8}$alkyl, $C_{2-8}$alkenyl (wherein alkyl and alkenyl are optionally substituted on a terminal carbon with a substituent selected from the group consisting of —C(O)H, —C(O)($C_{1-8}$)alkyl, —CO$_2$H, —CO$_2$($C_{1-8}$)alkyl, amino (substituted with two substituents independently selected from the group consisting of hydrogen and $C_{1-8}$alkyl), cyano, (halo)$_{1-3}$, hydroxy, nitro, cycloalkyl, heterocyclyl, aryl and heteroaryl), —CH(OH)—($C_{1-8}$)alkyl, $C_{1-8}$alkoxy (optionally substituted on a terminal carbon with a substituent selected from the group consisting of (halo)$_{1-3}$ and hydroxy), —C(O)H, —C(O)($C_{1-8}$)alkyl, —CO$_2$H, —CO$_2$($C_{1-8}$)alkyl, amino (substituted with two substituents independently selected from the group consisting of hydrogen, $C_{1-8}$alkyl and —C(O)($C_{1-8}$)alkyl), —C(O)amino (wherein amino is substituted with two substituents independently selected from the group consisting of hydrogen and $C_{1-8}$alkyl), —SO$_2$— {substituted with one substituent selected from the group consisting of heterocyclyl and amino (wherein amino is substituted with two substituents independently selected from the group consisting of hydrogen, $C_{1-8}$alkyl and —$C_{1-8}$alkylamino (wherein amino is substituted with two substituents independently selected from the group consisting of hydrogen and $C_{1-8}$alkyl))}, —NH—SO$_2$—($C_{1-8}$)alkenyl, cycloalkyl, heterocyclyl (optionally substituted with 1 to 2 oxo substituents), aryl and heteroaryl} and amino {substituted with two substituents independently selected from the group consisting of hydrogen, $C_{1-8}$alkyl, cycloalkyl, aryl and heteroaryl (wherein cycloalkyl, aryl and heteroaryl are optionally substituted with 1 to 5 substituents independently selected from the group consisting of $C_{1-8}$alkyl, cyano, halo, (halo)$_{1-3}$($C_{1-8}$)alkyl, (halo)$_{1-3}$($C_{1-8}$)alkoxy, hydroxy, hydroxy($C_{1-8}$)alkyl, hydroxy($C_{1-8}$)alkoxy and nitro)};

and pharmaceutically acceptable salts thereof.

Exemplified compounds of the present invention include a compound of Formula (I) selected from a compound of Formula (Ic):

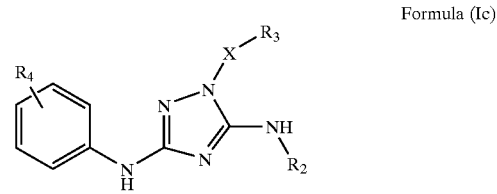

Formula (Ic)

wherein X, $R_2$, $R_3$ and $R_4$ are dependently selected from:

| Cpd | X | $R_2$ | $R_3$ | $R_4$ |
|---|---|---|---|---|
| 1 | C(O) | H | (2,6-F$_2$)Ph | 4-SO$_2$—NH$_2$ |
| 2 | C(O) | H | (2,6-F$_2$-3-CH$_3$)Ph | 4-SO$_2$—NH$_2$ |
| 3 | C(O) | H | (2,4,6-F$_3$)Ph | 4-SO$_2$—NH$_2$ |
| 4 | C(O) | H | (2-F)Ph | 4-SO$_2$—NH$_2$ |
| 5 | C(O) | H | (2,4-F$_2$)Ph | 4-SO$_2$—NH$_2$ |
| 6 | C(O) | H | (2-F-6-CF$_3$)Ph | 4-SO$_2$—NH$_2$ |
| 7 | C(O) | H | (2,6-Cl$_2$)Ph | 4-SO$_2$—NH$_2$ |
| 8 | C(O) | H | (2,4,6-Cl$_3$)Ph | 4-SO$_2$—NH$_2$ |
| 9 | C(O) | H | (2-NO$_2$)Ph | 4-SO$_2$—NH$_2$ |
| 10 | C(O) | H | [2,6-(OCH$_3$)$_2$]Ph | 4-SO$_2$—NH$_2$ |
| 11 | C(O) | H | [2,4,6-(CH$_3$)$_3$]Ph | 4-SO$_2$—NH$_2$ |
| 12 | C(O) | H | Ph | 4-SO$_2$—NH$_2$ |
| 13 | C(O) | H | (2,6-F$_2$)Ph | 4-SO$_2$-1-H-piperidin-1-yl |
| 14 | C(O) | H | 2-thienyl | 4-SO$_2$—NH$_2$ |
| 15 | C(O) | H | (3-CH$_3$)2-thienyl | 4-SO$_2$—NH$_2$ |
| 16 | C(O) | H | (3-F)2-thienyl | 4-SO$_2$—NH$_2$ |
| 17 | C(O) | H | (3-Cl)2-thienyl | 4-SO$_2$—NH$_2$ |
| 18 | C(O) | H | (3-OCH$_2$CH$_3$)2-thienyl | 4-SO$_2$—NH$_2$ |
| 19 | C(O) | H | (3-NHCOCH$_3$)2-thienyl | 4-SO$_2$—NH$_2$ |
| 20 | C(O) | H | (5-CH$_3$)2-thienyl | 4-SO$_2$—NH$_2$ |
| 21 | C(O) | H | (5-Br)2-thienyl | 4-SO$_2$—NH$_2$ |
| 22 | C(O) | H | (5-COCH$_3$)2-thienyl | 4-SO$_2$—NH$_2$ |
| 23 | C(O) | H | 2-thienyl | 4-SO$_2$-1-H-piperidin-1-yl |
| 24 | C(O) | H | (3-CH$_3$)2-thienyl | 4-SO$_2$-1-H-piperidin-1-yl |
| 25 | C(O) | H | 2-furyl | 4-SO$_2$—NH$_2$ |
| 26 | C(O) | H | 5-isoxazolyl | 4-SO$_2$—NH$_2$ |
| 27 | C(O) | H | 2-pyridinyl | 4-SO$_2$—NH$_2$ |
| 28 | C(O) | H | 3-pyridinyl | 4-SO$_2$—NH$_2$ |
| 29 | C(O) | H | 4-pyridinyl | 4-SO$_2$—NH$_2$ |

-continued

| Cpd | X | R₂ | R₃ | R₄ |
|---|---|---|---|---|
| 30 | C(O) | H | 3-thienyl | 4-SO₂—NH₂ |
| 31 | C(O) | H | 3a,7a-dihydrobenzo[b]thien-2-yl | 4-SO₂—NH₂ |
| 32 | C(O) | H | (5-CH₂CH₃)2-thienyl | 4-SO₂—NH₂ |
| 33 | C(O) | H | [3,5-(CH₃)₂]2-thienyl | 4-SO₂—NH₂ |
| 34 | C(O) | H | [2,4-(CH₃)₂]5-thiazolyl | 4-SO₂—NH₂ |
| 35 | C(O) | H | (3-Br)2-thienyl | 4-SO₂—NH₂ |
| 36 | C(O) | H | 4-(CH₃)-1,2,3-thiadiazol-5-yl | 4-SO₂—NH₂ |
| 37 | C(O) | H | 1,2,3-thiadiazol-4-yl | 4-SO₂—NH₂ |
| 38 | C(O) | H | cyclopentyl | 4-SO₂—NH₂ |
| 39 | C(O) | H | cyclohexyl | 4-SO₂—NH₂ |
| 40 | C(O) | H | 2-thienyl-CH₂ | 4-SO₂—NH₂ |
| 42 | C(O) | H | 2-thienyl-(CH)₂ | 4-SO₂—NH₂ |
| 43 | C(O) | H | (2,6-F₂)—Ph—CH₂ | 4-SO₂—NH₂ |
| 44 | C(O) | H | (2,6-F₂)Ph(CH)₂ | 4-SO₂—NH₂ |
| 45 | C(O) | H | cycloheptyl | 4-SO₂—NH₂ |
| 46 | C(O) | H | 4-CH₃-cyclohexyl | 4-SO₂—NH₂ |
| 47 | C(O) | H | 4-CH₃-cyclohexyl | 4-SO₂—NH₂ |
| 48 | C(O) | H | 4-(CH₂)₃CH₃-cyclohexyl | 4-SO₂—NH₂ |
| 49 | C(O) | H | 5-(2-pyridinyl)2-thienyl | 4-SO₂—NH₂ |
| 50 | C(O) | H | 3-(1H-pyrrol-1-yl)2-thienyl | 4-SO₂—NH₂ |
| 51 | C(O) | H | 5-[C(CH₃)₃]2-thienyl | 4-SO₂—NH₂ |
| 52 | C(O) | H | 5-[(CH)₂C(O)OC(CH₃)₃]2-thienyl | 4-SO₂—NH₂ |
| 53 | C(O) | H | Ph(C)₂ | 4-SO₂—NH₂ |
| 54 | C(O) | H | (2,6-F₂-3-NO₂)Ph | 4-SO₂—NH₂ |
| 55 | C(O) | H | (2,6-F₂-3-NH₂)Ph | 4-SO₂—NH₂ |
| 56 | C(O) | H | [2,6-(CH₃)₂]Ph | 4-SO₂—NH₂ |
| 57 | C(O) | H | (2-CH₃)Ph | 4-SO₂—NH₂ |
| 58 | C(O) | H | [2,6-F₂-3-CH(OH)CH₃]Ph | 4-SO₂—NH₂ |
| 59 | C(O) | H | (2,6-F₂)Ph | 4-SO₂—NH₂ |
| 60 | C(O) | H | (2,6-F₂-3-CH₃)Ph | 4-SO₂—NH₂ |
| 61 | C(O) | H | (2,6-F₂)Ph | H |
| 62 | C(O) | H | Ph | H |
| 63 | C(O) | H | (2,6-F₂)Ph | 3-Cl |
| 64 | C(O) | H | Ph | 3-Cl |
| 65 | C(O) | H | —NH(Ph) | H |
| 66 | C(S) | H | —NH[(2,6-F₂)Ph] | 4-SO₂—NH₂ |
| 67 | C(O) | H | —NH[(2,6-F₂)Ph] | 4-SO₂—NH₂ |
| 68 | SO₂ | H | (2,6-F₂)Ph | 4-SO₂—NH₂ |
| 69 | C(O) | H | (2-Cl-3-CH₃-6-F)Ph | 4-SO₂—NH₂ |
| 70 | C(O) | H | (2-Cl-6-F)Ph | 4-SO₂—NH₂ |
| 71 | C(O) | H | (2,6-F₂)Ph | 4-(4-CH₃-1,4-H-piperazin-1-yl) |
| 72 | C(O) | H | (2,6-F₂-3-CH₃)Ph | 4-(4-CH₃-1,4-H-piperazin-1-yl) |
| 73 | C(O) | H | (3-CH₃)2-thienyl | 4-(4-CH₃-1,4-H-piperazin-1-yl) |
| 74 | C(O) | H | [3,5-(CH₃)₂]2-thienyl | 4-(4-CH₃-1,4-H-piperazin-1-yl) |
| 75 | C(O) | H | (5-CH₂CH₃)2-thienyl | 4-(4-CH₃-1,4-H-piperazin-1-yl) |
| 76 | C(O) | H | (2,6-F₂)Ph | 4-SO₂—NH(CH₂CH₃) |
| 78 | C(O) | H | (2,6-F₂-5-Cl)Ph | 4-SO₂—NH₂ |
| 80 | C(O) | H | (2,6-F₂)Ph | 4-SO₂—NH(CH₃) |
| 81 | C(O) | H | (2,6-F₂-3-CH₃)Ph | 4-SO₂—NH(CH₃) |
| 82 | C(O) | H | (3-CH₃)2-thienyl | 4-SO₂—NH(CH₃) |
| 83 | C(O) | H | [3,5-(CH₃)₂]2-thienyl | 4-SO₂—NH(CH₃) |
| 84 | C(O) | H | (5-CH₂CH₃)2-thienyl | 4-SO₂—NH(CH₃) |
| 85 | C(O) | H | [3,5-(CH₃)₂]2-thienyl | 4-SO₂—N(CH₃)₂ |
| 86 | C(O) | H | (5-CH₂CH₃)2-thienyl | 4-SO₂—N(CH₃)₂ |
| 87 | C(O) | H | (3-CH₃)2-thienyl | 4-SO₂—N(CH₃)₂ |
| 88 | C(O) | H | (2,6-F₂-3-CH₃)Ph | 4-SO₂—N(CH₃)₂ |
| 89 | C(O) | H | (2,6-F₂)Ph | 4-SO₂—N(CH₃)₂ |
| 90 | C(O) | H | (5-CH₂CH₃)2-thienyl | 4-(1-H-imidazol-1-yl) |
| 91 | C(O) | H | (3-CH₃)2-thienyl | 4-(1-H-imidazol-1-yl) |
| 92 | C(O) | H | [3,5-(CH₃)₂]2-thienyl | 4-(1-H-imidazol-1-yl) |
| 93 | C(O) | H | (2,6-F₂)Ph | 4-(1-H-imidazol-1-yl) |
| 94 | C(O) | H | (2,6-F₂-3-CH₃)Ph | 4-(1-H-imidazol-1-yl) |
| 95 | C(O) | H | (2,6-F₂-3-CH₃)Ph | 4-(1-H-1,2,4-triazol-1-yl) |
| 96 | C(O) | H | (2,6-F₂)Ph | 4-(1-H-1,2,4-triazol-1-yl) |
| 97 | C(O) | H | (5-CH₂CH₃)2-thienyl | 4-(1-H-1,2,4-triazol-1-yl) |
| 98 | C(O) | H | [3,5-(CH₃)₂]2-thienyl | 4-(1-H-1,2,4-triazol-1-yl) |
| 99 | C(O) | H | (3-CH₃)2-thienyl | 4-(1-H-1,2,4-triazol-1-yl) |
| 100 | C(O) | H | (2,6-F₂)Ph | 4-(1-H-1,3,4-triazol-1-yl) |
| 101 | C(O) | H | (2,6-F₂-3-CH₃)Ph | 4-(1-H-1,3,4-triazol-1-yl) |
| 102 | C(O) | H | (3-CH₃)2-thienyl | 4-(1-H-1,3,4-triazol-1-yl) |

-continued

| Cpd | X | $R_2$ | $R_3$ | $R_4$ |
|---|---|---|---|---|
| 103 | C(O) | H | (5-$CH_2CH_3$)2-thienyl | 4-$SO_2$—NH[$(CH_2)_2N(CH_3)_2$] |
| 104 | C(O) | H | (3-$CH_3$)2-thienyl | 4-$SO_2$—NH[$(CH_2)_2N(CH_3)_2$] |
| 105 | C(O) | H | (2,6-$F_2$-3-$CH_3$)Ph | 4-$SO_2$—NH[$(CH_2)_2N(CH_3)_2$] |
| 106 | C(O) | H | (2,6-$F_2$)Ph | 4-$SO_2$—NH[$(CH_2)_2N(CH_3)_2$] |
| 107 | C(O) | H | [3,5-$(CH_3)_2$]2-thienyl | 4-$SO_2$—NH[$(CH_2)_2N(CH_3)_2$] |
| 108 | C(O) | H | [3,5-$(CH_3)_2$]2-thienyl | 4-NH—$SO_2$—$CH_3$ |
| 109 | C(O) | H | (3-$CH_3$)2-thienyl | 4-NH—$SO_2$—$CH_3$ |
| 110 | C(O) | H | (5-$CH_2CH_3$)2-thienyl | 4-NH—$SO_2$—$CH_3$ |
| 111 | C(O) | H | (2,6-$F_2$)Ph | 4-NH—$SO_2$—$CH_3$ |
| 112 | C(O) | H | (2,6-$F_2$-3-$CH_3$)Ph | 4-NH—$SO_2$—$CH_3$ |
| 113 | C(O) | H | (3-$CH_3$)2-thienyl | 4-(2-imidazolidinone) |
| 114 | C(O) | H | (2,6-$F_2$-3-$CH_3$)Ph | 4-(2-imidazolidinone) |
| 115 | C(O) | H | (2,6-$F_2$)Ph | 4-(2-imidazolidinone) |
| 116 | C(O) | H | (3-$CH_3$)2-thienyl | 4-(1,1-dioxido-2-isothiazolidinyl) |
| 117 | C(O) | H | (2,6-$F_2$)Ph | 4-(1,1-dioxido-2-isothiazolidinyl) |
| 118 | C(O) | H | (2,6-$F_2$)Ph | 4-$SO_2$—NH-2-pyridinyl |
| 119 | C(O) | H | (5-$CH_2CH_3$)2-thienyl | 4-$SO_2$—NH-2-pyridinyl |
| 120 | C(O) and, | H | [3,5-$(CH_3)_2$]2-thienyl | 4-$SO_2$—NH-2-pyridinyl |
| 121 | C(O) | H | (3-$CH_3$)2-thienyl | 4-$SO_2$—NH-2-pyridinyl | and pharmaceutically acceptable salts thereof.

Exemplified compounds of the present invention include a compound of Formula (I) selected from a compound of Formula (Id):

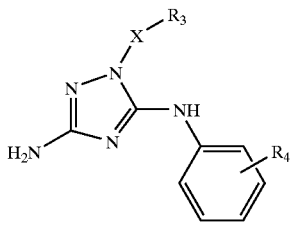

Formula (Id)

wherein X, $R_3$ and $R_4$ are dependently selected from:

| Cpd | X | $R_3$ | $R_4$ |
|---|---|---|---|
| 122 | C(O) | (2,6-$F_2$)Ph | 4-$SO_2$—$NH_2$ |
| 123 | C(O) | (2,6-$F_2$-3-$CH_3$)Ph | 4-$SO_2$—$NH_2$ |
| 124 | C(O) | (2,6-$F_2$)Ph | H |
| 125 | C(O) | Ph | H |
| 126 | C(O) | (2,6-$F_2$)Ph | 3-Cl |
| 127 | C(O) and, | Ph | 3-Cl |
| 128 | C(S) | —NH[(2,6-$F_2$)Ph] | 4-$SO_2$—$NH_2$ | and pharmaceutically acceptable salts thereof.

Exemplified compounds of the present invention include a compound of Formula (I) selected from a compound of Formula (Ie):

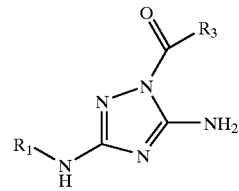

Formula (Ie)

wherein $R_1$ and $R_3$ are dependently selected from:

| Cpd | $R_1$ | $R_3$ |
|---|---|---|
| 79 | $CH_3$ | (3-$CH_3$)2-thienyl | and pharmaceutically acceptable salts thereof.

The compounds of the present invention may also be present in the form of pharmaceutically acceptable salts. For use in medicine, the salts of the compounds of this invention refer to non-toxic "pharmaceutically acceptable salts" (Ref. International J. Pharm., 1986, 33, 201–217; J. Pharm.Sci., 1997 (January), 66, 1, 1). Other salts may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds, which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. Where the processes for the preparation of the compounds according to the invention give rise to mixture of stereoisomers, these isomers may be separated by conventional techniques such as preparative chromatography. The compounds may be prepared in racemic form or individual enantiomers may be prepared by standard techniques known to those skilled in the art, for example, by enantiospecific synthesis or resolution, formation of diastereomeric pairs by salt formation with an optically active acid, followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column. It is to be understood that all such isomers and mixtures thereof are encompassed within the scope of the present invention and moreover that the term "a compound of Formula x" will encompass a compound's enantiomers, diastereomers, and the like.

Unless specified otherwise, the term "alkyl" refers to a saturated straight or branched chain consisting solely of 1–8 hydrogen substituted carbon atoms; preferably, 1–6 hydrogen substituted carbon atoms; and, most preferably, 1–4 hydrogen substituted carbon atoms. The term "alkenyl" refers to a partially unsaturated straight or branched alkyl chain that contains at least one double bond. The term "alkynyl" refers to a partially unsaturated straight or branched alkyl chain that contains at least one triple bond. The term "alkoxy" refers to —O-alkyl, where alkyl is as defined supra.

The term "cycloalkyl" refers to a saturated or partially unsaturated cyclic alkyl ring consisting of 3–8 hydrogen substituted carbon atoms. Examples include, and are not limited to, cyclopropyl, cyclopentyl, cyclohexyl or cycloheptyl.

The term "heterocyclyl" refers to a saturated or partially unsaturated ring having five members of which at least one member is a N, O or S atom and which optionally contains one additional O atom or one, two or three additional N atoms; a saturated or partially unsaturated ring having six members of which one, two or three members are a N atom; a saturated or partially unsaturated bicyclic ring having nine members of which at least one member is a N, O or S atom and which optionally contains one, two or three additional N atoms; and, a saturated or partially unsaturated bicyclic ring having ten members of which one, two or three members are a N atom. Examples include, and are not limited to, pyrrolinyl, pyrrolidinyl, dioxolanyl, imidazolinyl, imidazolidinyl, pyrazolinyl, pyrazolidinyl, piperidinyl, morpholinyl or piperazinyl.

The term "aryl" refers to an aromatic monocyclic ring system containing 6 hydrogen substituted carbon atoms, an aromatic bicyclic ring system containing 10 hydrogen substituted carbon atoms or an aromatic tricyclic ring system containing 14 hydrogen substituted carbon atoms. Examples include, and are not limited to, phenyl, naphthalenyl or anthracenyl.

The term "heteroaryl" refers to an aromatic monocyclic ring system containing five members of which at least one member is a N, O or S atom and which optionally contains one, two or three additional N atoms, an aromatic monocyclic ring having six members of which one, two or three members are a N atom, an aromatic bicyclic ring having nine members of which at least one member is a N, O or S atom and which optionally contains one, two or three additional N atoms and an aromatic bicyclic ring having ten members of which one, two or three members are a N atom. Examples include, and are not limited to, furyl, thienyl, pyrrolyl, oxazolyl, thiazolyl, imidazolyl, pyrazolyl, isoxazolyl, isothiazolyl, pyridinyl, pyridazinyl, pyrimidinyl, pyrazinyl, indolyl, indazolyl, quinolinyl or isoquinolinyl.

The term "halo" or "halogen" refers to a fluoro, chloro, bromo or iodo atom.

"Independently" means that when a group is substituted with more than one substituent that the substituents may be the same or different. "Dependently" means that the substituents are specified in an indicated combination of structure variables.

An embodiment of the invention is a pharmaceutical composition or medicament comprising a pharmaceutically acceptable carrier and any of the compounds described above. Illustrative of the invention is a pharmaceutical composition or medicament made by mixing any of the compounds described above and a pharmaceutically acceptable carrier. Another illustration of the invention is a process for making a pharmaceutical composition or medicament comprising mixing any of the compounds described above and a pharmaceutically acceptable carrier. Further illustrative of the present invention are pharmaceutical compositions or medicaments comprising one or more compounds of this invention in association with a pharmaceutically acceptable carrier.

As used herein, the term "composition" is intended to encompass a product comprising the specified ingredients in the specified amounts, as well as any product which results, directly or indirectly, from combinations of the specified ingredients in the specified amounts.

The compounds of the present invention are selective kinase or dual-kinase inhibitors useful in a method for treating or ameliorating a kinase or dual-kinase mediated disorder. In particular, the kinase is selected from a cyclin dependent kinase and a tyrosine kinase. More particularly, the kinase is selected from cyclin dependent kinase-1, cyclin dependent kinase-2, cyclin dependent kinase-4, vascular endothelial growth factor receptor-2, endothelial growth factor receptor or human epidermal growth factor receptor-2.

Cyclin-dependent kinase inhibitors play a critical role in regulating progression of the eukaryotic cell through the cell cycle by associating with protein complexes composed of cyclins and cyclin-dependent kinases and thus down-regulating the activity of the cyclin-dependent kinases. Pathways involving cyclin-dependent kinase inhibitors are frequently disrupted in tumor cells leading to abnormal regulation of the cell cycle. Overexpression of cyclin-dependent kinase inhibitors leads to arrest of cells at one of the check points in the cell cycle. Therefore, using cyclin-dependent kinase inhibitors for tumor therapy is intuitively attractive because it has the potential for tumour growth.

Inhibition or for the inhibition or control of uncontrolled cell proliferation such as occurs in some angiopathies, benign tumor growth, leukemias, and the like. A particularly good CDK inhibitor target for the design of anti-tumor agents is the CDK-1 receptor. This protein controls the last checkpoint in the cell cycle between the G2 and M phase.

A second protein target that can facilitate elimination of a tumor is the tyrosine kinase vascular endothelial growth factor (VEGF) receptor. This protein is associated with both normal and pathological angiogenesis. The VEGF receptors are tripartite, consisting of an extracellular ligand-binding domain, a transmembrane domain and an intracellular tyrosine kinase domain. Presently there are two known VEGF receptors: (1) VEGF-R2 (KDR/Flk1/VEGF-R2), a receptor that mediates the biological activities of mitogenesis and proliferation of endothelial cells; and (2) VEGF-R1 (Flt1/VEGF-R1), a receptor that mediates functions such as endothelial cell adhesion. Inhibition of VEGF-R2 signalling has been shown to inhibit the process of angiogenesis. Inhibitors of this receptor are likely useful in controlling or limiting angiogenesis.

Many conventional cytotoxic cancer therapies destroy the rapidly dividing epithelium of the hair follicle and induce alopecia (hair loss). Inhibition of cyclin dependent kinases may represent a therapeutic strategy for prevention of chemotherapy-induced alopecia by arresting the cell cycle and reducing the sensitivity of epithelial cells to antitumor agents (Davis S. T., etal., Prevention of chemotherapy-induced alopecia in rats by CDK inhibitors, *Science*, 2001, (January 5), 291, 5501, 25–6). Topical application of non-apoptotic CDK inhibitors represents a potentially useful approach for the prevention of chemotherapy-induced alopecia in cancer patients.

Although coronary angioplasty is a highly effective procedure used to reduce the severity of coronary occlusion, its long-term success is limited by a high rate of restenosis. Vascular smooth muscle cell activation, migration, and proliferation is largely responsible for restenosis following angioplasty (Ross, R., *Nature*, 1993, 362, 801–809). Recent studies have shown that CDK2 is activated very early after endothelial denudation in a rat carotid artery model of restenosis (Wei, G. L., et al., *Circ. Res.*, 1997, 80, 418–426). Therefore, antiproliferative therapies targeted to cyclin dependent kinases or other components of the cell cycle machinery may be a suitable approach to treat these disorders.

Embodiments of the method of the present invention include a method for treating or ameliorating a selective kinase or dual-kinase mediated disorder in a subject in need thereof comprising administering to the subject a therapeutically effective amount of an instant compound or pharmaceutical composition thereof. The therapeutically effective amount of the compounds of Formula (I) exemplified in such a method is from about 0.001 mg/kg/day to about 300 mg/kg/day.

Embodiments of the present invention include the use of a compound of Formula (I) for the preparation of a medicament for treating or ameliorating a kinase or dual-kinase mediated disorder in a subject in need thereof.

In accordance with the methods of the present invention, an individual compound of the present invention or a pharmaceutical composition thereof can be administered separately at different times during the course of therapy or concurrently in divided or single combination forms. The instant invention is therefore to be understood as embracing all such regimes of simultaneous or alternating treatment and the term "administering" is to be interpreted accordingly.

Embodiments of the present method include a compound or pharmaceutical composition thereof advantageously co-administered in combination with other agents for treating or ameliorating a kinase or dual-kinase mediated disorder. The combination product comprises co-administration of a compound of Formula (I) or pharmaceutical composition thereof and an additional agent for treating or ameliorating a kinase or dual-kinase mediated disorder, the sequential administration of a compound of Formula (I) or pharmaceutical composition thereof and an additional agent for treating or ameliorating a kinase or dual-kinase mediated disorder, administration of a pharmaceutical composition containing a compound of Formula (I) or pharmaceutical composition thereof and an additional agent for treating or ameliorating a kinase or dual-kinase mediated disorder or the essentially simultaneous administration of a separate pharmaceutical composition containing a compound of Formula (I) or pharmaceutical composition thereof and a separate pharmaceutical composition containing an additional agent for treating or ameliorating a kinase or dual-kinase mediated disorder.

The term "other agents" includes, and is not limited to, anti-angiogenic agents, anti-tumor agents, cytotoxic agents, inhibitors of cell proliferation, and the like. The term "treating or ameliorating" includes, and is not limited to, facilitating the eradication of, inhibiting the progression of or promoting stasis of a malignancy. For example, a dual CDK1-VEGF-R inhibitor compound of the present invention, acting as an anti-angiogenic agent can be administered in a dosing regimen with at least one other cytotoxic compound, such as a DNA alkylating agent. Preferred anti-tumor agents are selected from the group consisting of cladribine (2-chloro-2'-deoxy-(beta)-D-adenosine), Chlorambucil (4-[bis(2-chlorethyl)amino]benzenebutanoic acid), DTIC-Dome (5-(3,3-dimethyl-1-triazeno)-imidazole-4-carboxamide), platinum chemotherapeutics and nonplatinum chemotherapeutics. Platinum containing anti-tumor agents include, but are not limited to, cisplatin (cis-dichlorodiamineplatinum). Non-platinum containing anti-tumor agents include, but are not limited to, cyclophosphamide, fluorouracil, epirubicin, methotrexate, vincristine, doxorubicin, bleomycin, and etoposide. Each anti-tumor agent is administered in a therapeutically effective amount, which varies based on the agent used, the type of malignancy to be treated or ameliorated and other conditions, according to methods well known in the art.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human, that is being sought by a researcher, veterinarian, medical doctor, or other clinician, which includes alleviation of the symptoms of the disease or disorder being treated.

The ubiquitous nature of the kinase isoforms and their important roles in physiology provide incentive to produce highly selective kinase inhibitors. Given the evidence demonstrating linkage of certain isoforms to disease states, it is reasonable to assume that inhibitory compounds that are selective to one or two isoforms (those compounds selective to at least two cyclin dependent kinase or tyrosine kinase isoforms are referred to as dual kinase inhibitors) or to a single isoform relative to other isoforms and other kinases are superior therapeutic agents. Such compounds should demonstrate greater efficacy and lower toxicity by virtue of their specificity. Accordingly, it will be appreciated by one skilled in the art that a compound of Formula (I) is therapeutically effective for certain kinase or dual-kinase mediated disorders based on the modulation of the disorder by selective kinase or dual-kinase inhibition. The activity of the instant compounds as selective kinase or dual-kinase inhibitors is derived from the novel combination of the structural elements X, $R_3$ and $R_4$ optimally substituted on the triazole scaffold. The usefulness of a compound of Formula (I) as a selective kinase or dual-kinase inhibitor can be determined according to the methods disclosed herein and the scope of such usefulness includes use in one or more kinase or dual-kinase mediated disorders.

Therefore, the term "kinase or dual-kinase mediated disorders" as used herein, includes, and is not limited to compounds capable of inhibiting one or more kinases where knase inhibition is also associated with cancers, abnormal cell proliferation, tumor growth, tumor vascularization, as well as angiopathy, angiogenesis, chemotherapy-induced alopecia and restenosis.

The compounds of this invention are useful as an adjunct to a variety of chemotherapeutic agents that are recommended for specific cancer therapy regimes. For example, the compounds of this invention have been demonstrated to be useful in combination therapies with at least one other chemotherapeutic agent for the treatment of a number of different cancers and advantageously appears to facilitate the use of a reduced dose of the chemotherapeutic agent that is recommended for a particular cancer or cell proliferation disorder. Therefore, it is contemplated that the compounds of this invention can be used in a treatment regime before the administration of a particular chemotherapeutic agent recommended for the treatment of a particular cancer, during admninstration of the chemotherapeutic agent or after treatment with a particular chemotherapeutic agent.

Pharmaceutical compositions contemplated within this invention can be prepared according to conventional pharmaceutical techniques. A pharmaceutically acceptable carrier may be used in the composition of the invention. The composition may take a wide variety of forms depending on the form of preparation desired for administration including, but not limited to, intravenous (both bolus and infusion), oral, nasal, transdermal, topical with or without occlusion, intraperitoneal, subcutaneous, intramuscular or parenteral, all using forms well known to those of ordinary skill in the pharmaceutical arts. In preparing the compositions in oral dosage form, one or more of the usual pharmaceutical carriers may be employed, such as water, glycols, oils, alcohols, flavoring agents, preservatives, coloring agents, syrup and the like in the case of oral liquid preparations (for example, suspensions, elixirs and solutions), or carriers such as starches, sugars, diluents, granulating agents, lubricants, binders, disintegrating agents and the like in the case of oral solid preparations (for example, powders, capsules and tablets).

As is also known in the art, the compounds may alternatively be administered parenterally via injection of a formulation consisting of the active ingredient dissolved in an inert liquid carrier. The injectable formulation can include the active ingredient mixed with an appropriate inert liquid carrier. Acceptable liquid carriers include vegetable oils such as peanut oil, cotton seed oil, sesame oil, and the like, as well as organic solvents such as solketal, glycerol, formal, and the like. As an alternative, aqueous parenteral formulations may also be used. For example, acceptable aqueous solvents include water, Ringer's solution and an isotonic aqueous saline solution. Further, a sterile non-volatile oil can usually be employed as solvent or suspending agent in the aqueous formulation. The formulations are prepared by dissolving or suspending the active ingredient in the liquid carrier such that the final formulation contains from 0.005 to 10% by weight of the active ingredient. Other additives including a preservative, an isotonizer, a solubilizer, a stabilizer and a pain-soothing agent may adequately be employed.

Furthermore, compounds of the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

Because of their ease of administration, tablets and capsules represent an advantageous oral dosage unit form, wherein solid pharmaceutical carriers are employed. If desired, tablets may be sugarcoated or enteric-coated by standard techniques.

For liquid forms the active drug component can be combined in suitably flavored suspending or dispersing agents such as the synthetic and natural gums, including for example, tragacanth, acacia, methyl-cellulose and the like. Other dispersing agents that may be employed include glycerin and the like.

The compounds of the present invention can also be administered in the form of liposome delivery systems, such as small unilamellar vesicles, large unilamellar vesicles and multilamellar vesicles. Liposomes containing delivery systems as well known in the art are formed from a variety of phospholipids, such as cholesterol, stearylamine or phosphatidylcholines.

The instant pharmaceutical composition will generally contain a per dosage unit (e.g., tablet, capsule, powder, injection, teaspoonful and the like) from about 0.001 to about 100 mg/kg. In one embodiment, the instant pharmaceutical composition contains a per dosage unit of from about 0.01 to about 50 mg/kg of compound, and preferably from about 0.05 to about 20 mg/kg. Methods are known in the art for determining therapeutically effective doses for the instant pharmaceutical composition. The therapeutically effective amount for administering the pharmaceutical composition to a human, for example, can be determined mathematically from the results of animal studies.

| Abbreviations | |
|---|---|
| "Cpd" | Compound |
| "CSCl$_2$" | thiophosgene |
| "DIC" | diisopropyl carbodiimide |
| "DMF" | N,N-dimethylformamide |
| "EDCI" | ethyl dimethylaminopropyl carbodiimide |
| "HOBT" | hydroxybenzyl triazole |
| "NH$_2$NH$_2$" | hydrazine |
| "Pd" | palladium(II) |
| "Ph" | phenyl |
| "rt" | room temperature |
| "TBAF" | tetrabutylammonium fluoride |
| "TFA" | trifluoroacetic acid |
| "THF" | tetrahydrofuran |

Nomenclature

Compounds are named according to nomenclature well known in the art, as exemplified using ring numbering as follows:

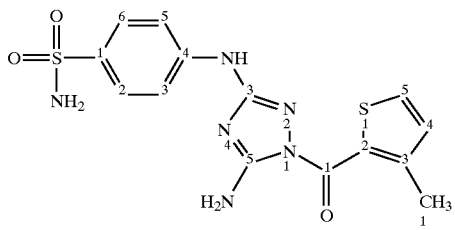

4-[[5-amino-1-[(3-methyl-2-thienyl)carbonyl]-1H-1,2,4-triazol-3-yl]amino]-benzenesulfonamide Names can be generated using a nomenclature system based on this example, or may be generated using commercial chemical naming software such as ACD/Index Name (Advanced Chemistry Development, Inc., Toronto, Ontario).

General Synthetic Methods

Representative compounds of the present invention can be synthesized in accordance with the general synthetic methods described below and are illustrated more particularly in the schemes that follow. Since the schemes are illustrations, the invention should not be construed as being limited by the chemical reactions and conditions expressed. The preparation of the various starting materials used in the schemes is well within the skill of persons versed in the art.

Scheme A

To prepare a Compound A3 (as described in Jenardanan, G. C., Francis, M., Deepa, S., and Rajaskekharan, N. R., *Synthetic Communications*, 1997, 27, 19, 3457–3462), the isocyanate Compound A1 (prepared according to R. L. McKee and R. W. Bost, *J. Am. Chem. Soc.*, 1946, 68, 2506–2507) (wherein $R_1$ is as previously defined) was dissolved in a suitable solvent and combined with a suspension of Compound A2 and potassium hydroxide in solvent. The mixture was warmed and stirred and the product Compound A3 was isolated by precipitation in cold water.

To prepare a Compound A5 (Reiter, J., Pongo, L. and Dvortsak, P,. *J. Heterocyclic Chemistry*, 1987, 24, 127–142), Compound A3 was dissolved in a suitable solvent and reacted with hydrazine. The solvent was then evaporated and the residue of Compound A3 was refluxed in an alcohol solvent to produce a solid Compound A4. Compound A4 was dissolved in a suitable solvent and reacted with $R_3CO_2H$ or $R_3COCl$ (wherein $R_3$ is as previously defined) and a coupling reagent such as DIC (diisopropyl carbodiimide) or EDCI (ethyl dimethylaminopropyl carbodiimide) to yield the target Compound A5.

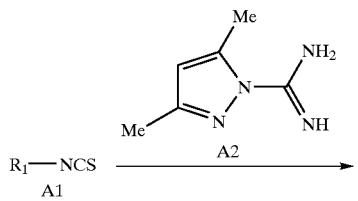

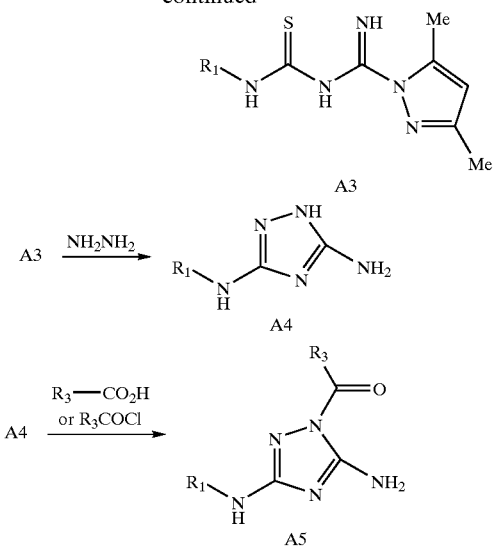

Scheme B

Alternatively, Compound B3 was prepared according to published procedure (as described in Webb, R. L., Eggleston, D. S. and Labaw, C. S., *J. Heterocyclic Chemistry*, 1987, 24, 275–278). Following the procedure of Scheme A, Compound B3 was reacted with hydrazine to produce the target intermediate Compound A4.

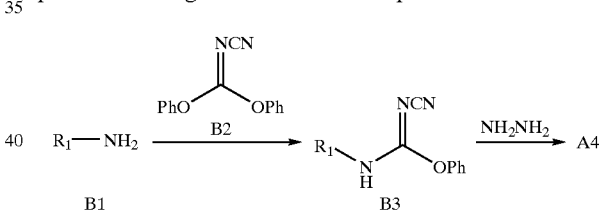

Scheme C

Compound C1 (CAS # 1455-77-2) was dissolved in a suitable solvent and reacted with $R_3CO_2H$ or $R_3COCl$ (wherein $R_3$ is as previously defined) and a coupling reagent such as DIC or EDCI to yield the Compound C2. Compound C2 was purified, dissolved in a suitable solvent and reacted in an inert atmosphere with $R_1$-halo (wherein $R_1$ and halo are as previously defined; in addition to halo, $R_1$ may be coupled with another suitable leaving group) in the presence of a base, such as potassium carbonate, and a catalyst, such as a palladium complex. The product Compound A5 was isolated using conventional means.

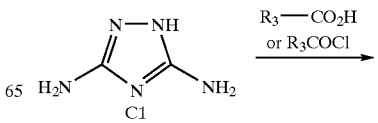

-continued

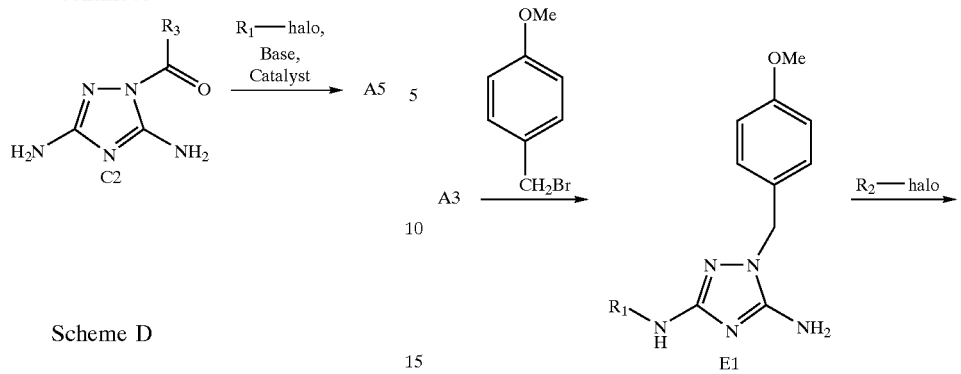

Scheme D

Alternatively, Compound D1 (CAS# 24807-56-5) was dissolved in a suitable solvent and reacted with $R_1NH_2$ in the presence of a base such as potassium carbonate, and a catalyst such as a palladium complex to yield the Compound D2. Compound D2 was purified, dissolved in a suitable solvent and subjected to catalytic hydrogenation to give Compound A4. Compound A4 may then be used to produce other target compounds of the invention as described in Scheme A.

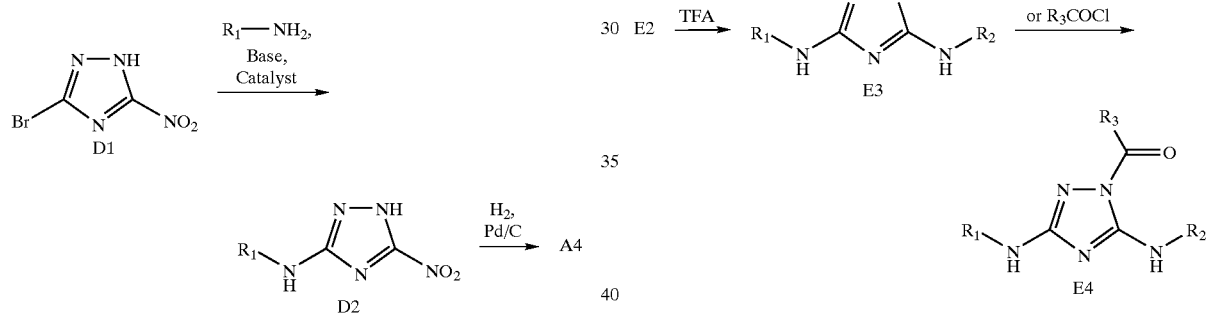

Scheme E

Compound A3 was dissolved in a solvent and reacted with a protecting group such as a substituted benzyl halide (for example, 4-methoxybenzyl bromide) in the presence of a base (such as potassium carbonate) to yield a Compound E1. Compound E1 was purified, dissolved in a suitable solvent and then reacted with $R_2$-halo (wherein $R_2$ and halo are as previously defined; in addition to halo, $R_2$ may be coupled with another suitable leaving group) in the presence of a base (such as potassium carbonate) to give a Compound E2. Compound E2 was treated with a suitable reagent, such as trifluoroacetic acid, which upon heating produced Compound E3. Compound E3 was dissolved in a suitable solvent and reacted with $R_3CO_2H$ or $R_3COCl$ (wherein $R_3$ is as previously defined) and a coupling reagent such as DIC or EDCI to yield a target Compound E4. The product Compound E4 was purified using conventional means.

Alternatively, to prepare a Compound E4, Compound A5 was dissolved in a suitable solvent and reacted with $R_2$-halo (wherein $R_2$ and halo are as previously defined; in addition to halo, $R_2$ may be coupled with another suitable leaving group) in the presence of a base (such as potassium carbonate).

Specific Synthetic Examples

Specific compounds which are representative of this invention were prepared as per the following examples and reaction sequences; the examples and the diagrams depicting the reaction sequences are offered by way of illustration, to aid in the understanding of the invention and should not be construed to limit in any way the invention set forth in the claims which follow thereafter. The depicted intermediates may also be used in subsequent examples to produce additional compounds of the present invention. No attempt has been made to optimize the yields obtained in any of the reactions. One skilled in the art would know how to increase such yields through routine variations in reaction times, temperatures, solvents and/or reagents.

$^1$H and $^{13}$C NMR spectra were measured on a Bruker AC-300 (300 MHz) spectrometer using tetramethylsilane and DMSO respectively as internal standards. Elemental analyses were obtained by Quantitative Technologies Inc. (Whitehouse, N.J.), and the results were within 0.4% of the calculated values unless otherwise mentioned. Melting points were determined in open capillary tubes with a Mel-Temp II apparatus (Laboratory Devices Inc.) and were uncorrected. Electrospray mass spectra (MS-ES) were recorded on a Hewlett Packard 59987A spectrometer.

EXAMPLE 1

4-[[5-amino-1-(2,6-difluorobenzoyl)-1H-1,2,4-triazol-3-yl]amino]-benzenesulfonamide (Cpd 1)

A suspension of 1-amidino-3,5-dimethylpyrazole nitrate Compound 1C (2.012 g, 10 mmol) and potassium hydroxide powder (0.561 g, 10 mmol) in DMF (8 mL) at 0° C. was added to a DMF solution (3 mL) of isocyanate Compound 1B (prepared from sulfanilamide Compound 1A and thiophosgene according to R. L. McKee and R. W. Bost, *J. Am. Chem. Soc.*, 1946, 68, 2506–2507). The reaction mixture was warmed up to 50–60° C., stirred for 1 h, and then poured into 250 ml of icy water. The resultant yellow solid was filtered, rinsed with water and dried in vacuo to give an intermediate Compound 1D as yellow powder (2.5513 g); m.p. 69–80° C. (decomposed); $^1$H NMR (300 MHz, CD$_3$OD) δ 7.90 (m, 4H), 6.05 (s, 1H), 2.22 (s, 3H), 2.20 (s, 3H); (CDCl$_3$) δ 10.75 (s, br, 1H), 8.35 (s, br, 1H), 7.90 (q, 4H), 7.65 (s, br, 2H), 5.95 (s, 1H), 5.00 (s, br, 2H); MS (ESI) m/z: 353 (M+H$^+$).

Hydrazine (1.845 g, 57.58 mmol) was added to a solution of the intermediate Compound 1D (1.88 g, 5.33 mmol) in THF (60 mL). The reaction mixture was stirred vigorously at 50–60° C. for 2–3 hours, and then evaporated in vacuo. The residue was then refluxed in methanol (60 mL) and cooled down to rt. The resultant solid was collected by filtration and rinsed with methanol to produce intermediate Compound 1E as a gray solid (0.8722 g, 64%). m.p. 291–296° C. (decomposed); $^1$H NMR (300 MHz, (CD$_3$)$_2$SO) δ 9.20 (s, 1H), 7.60 (m, 4H), 7.00 (s, 2H), 5.90 (s, 2H); MS (ESI) m/z: 255 (M+H$^+$), 277 (M+Na$^+$).

2,6-difluorobenzoyl chloride Compound 1F (41.4 uL, 0.33 mmol) was added to a solution of the intermediate Compound 1E (63.6 mg, 0.25 mmol) dissolved in anhydrous pyridine (2.5 mL) in an ice-water bath. The resulting reaction mixture was stirred at rt for 6 hours, and then evaporated in vacuo to dryness. Chromatography purification of the residue with 10% methanol/methylene chloride and recrystallization from THF/methylene chloride gave Compound 1 (50.2 mg, 51%) as a white powder. m.p. 149–155° C. (decomposed); $^1$H NMR (300 MHz, CD$_3$OD) δ 7.65 (m, 3H), 7.55 (d, 2H), 7.18 (t, 2H); ((CD$_3$)$_2$SO) δ 9.86 (s, 1H), 8.03 (s, 2H), 7.72 (m, 1H), 7.58 (d, J=8.9 Hz, 2H), 7.46 (d, J=8.9 Hz, 2H), 7.35 (t, J=8.3 Hz, 2H), 7.11 (s, 2H); $^{13}$C NMR (300 MHz, (CD$_3$)$_2$SO) δ 160.4, 159.7, 158.9, 157.9, 157.1, 157.0, 156.6, 144.0, 135.6, 133.9, 127.0, 116.3, 112.9, 112.5, 112.3; MS (ESI) m/z: 395 (M+H$^+$), 417 (M+Na$^+$). Anal. Calcd. For C$_{15}$H$_{12}$F$_2$N$_6$O$_3$S: C, 45.69; H, 3.07; N, 21.31. Found: C, 45.29; H, 3.04; N, 20.89.

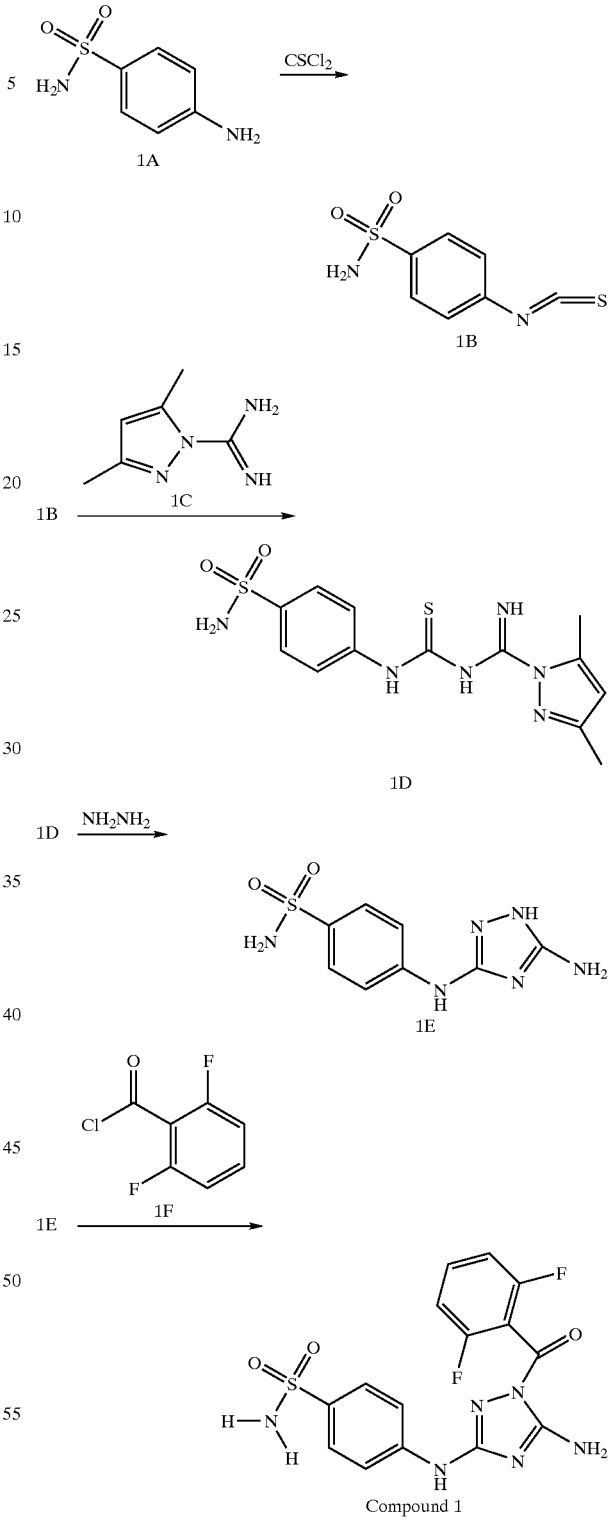

Using the procedure for Example 1, the following compounds were prepared by acylation of the intermediate Compound 1E using the indicated starting material in place of Compound 1F and reagent(s):

| Cpd | Name/Data | Starting Mat'l |
|---|---|---|
| 2 | 4-[[5-amino-1-(2,6-difluoro-3-methylbenzoyl)-1H-1,2,4-triazol-3-yl]amino]-benzenesulfonamide<br>$^1$H NMR (300 MHz, (CD$_3$)$_2$CO) δ 8.80 (s, 1H), 7.78–7.55 (m, 5H), 7.52 (s, 2H), 7.12 (t, 2H), 6.38 (s, 2H), 2.22 (s, 3H); MS (ESI) m/z: 409 (M + H$^+$), 431 (M + Na$^+$) | 2,6-difluoro-3-methylbenzoyl chloride in anhydrous pyridine |
| 3 | 4-[[5-amino-1-(2,3,6-trifluorobenzoyl)-1H-1,2,4-triazol-3-yl]amino]-benzenesulfonamide<br>$^1$H NMR (300 MHz, (CD$_3$)$_2$CO) δ 8.85 (s, 1H), 7.78–7.50 (m, 7H), 7.32 (m, 1H), 6.38 (s, 2H); MS (ESI) m/z: 413 (M + H$^+$), 435 (M + Na$^+$) | 2,3,6-trifluorobenzoyl chloride in anhydrous pyridine |
| 4 | 4-[[5-amino-1-(2-fluorobenzoyl)-1H-1,2,4-triazol-3-yl]amino]-benzenesulfonamide<br>$^1$H NMR (300 MHz, (CD$_3$)$_2$CO) δ 8.90 (s, br, 1H), 8.00 (s, br, 2H), 7.82 (t, 1H), 7.78–7.20 (m, 7H), 6.35 (s, br, 2H); MS (ESI) m/z: 377 (M + H$^+$), 399 (M + Na$^+$) | 2-fluorobenzoyl chloride in anhydrous pyridine |
| 5 | 4-[[5-amino-1-(2,4-difluorobenzoyl)-1H-1,2,4-triazol-3-yl]amino]-benzenesulfonamide<br>$^1$H NMR (300 MHz, (CD$_3$)$_2$CO) δ 8.88 (s, 1H), 7.95 (s, 2H), 7.78–7.58 (m, 4H), 7.48 (s, 2H), 7.35–7.77 (m, 2H), 6.38 (s, 2H); MS (ESI) m/z: 395 (M + H$^+$), 417 (M + Na$^+$) | 2,4-difluoromethylbenzoyl chloride in anhydrous pyridine |
| 6 | 4-[[5-amino-1-[2-fluoro-6-(trifluoromethyl)benzoyl]-1H-1,2,4-triazol-3-yl]amino]-benzenesulfonamide<br>$^1$H NMR (300 MHz, (CD$_3$)$_2$SO) δ 9.86 (s, 1H), 8.06 (s, 2H), 7.85 (m, 3H), 7.54 (d, J = 8.9 Hz, 2H), 7.40 (d, J = 8.9 Hz, 2H), 7.09 (s, 2H); MS (ESI) m/z: 445 (M + H$^+$), 467 (M + Na$^+$) | 2-fluoro-6-(trifluoromethyl)-benzoyl chloride in THF |
| 7 | 4-[[5-amino-1-(2,6-dichlorobenzoyl)-1H-1,2,4-triazol-3-yl]amino]-benzenesulfonamide<br>$^1$H NMR (300 MHz, (CD$_3$)$_2$CO) δ 8.82 (s, 1H), 7.68–7.45 (m, 9H), 6.35 (s, 2H); (CD$_3$OD) δ 7.60 (d, 2H), 7.55 (m, 3H), 7.38 (d, 2H); MS (ESI) m/z: 428 (M + H$^+$), 450 (M + Na$^+$) | 2,6-dichlorobenzoyl chloride in anhydrous pyridine |
| 8 | 4-[[5-amino-1-(2,4,6-trichlorobenzoyl)-1H-1,2,4-triazol-3-yl]amino]-benzenesulfonamide<br>$^1$H NMR (300 MHz, (CD$_3$)$_2$CO) δ 8.88 (s, 1H), 7.78 (s, 2H), 7.75–7.48 (m, 6H), 6.38 (s, 2H); MS (ESI) m/z: 462 (M + H$^+$), 484 (M + Na$^+$) | 2,4,6-trichlorobenzoyl chloride in anhydrous pyridine |
| 9 | 4-[[5-amino-1-(2-nitrobenzoyl)-1H-1,2,4-triazol-3-yl]amino]-benzenesulfonamide<br>$^1$H NMR (300 MHz, CD$_3$OD) δ 8.28 (d, 2H), 8.95–7.85 (m, 3H), 7.62 (d, 2H), 7.35 (d, 2H); MS (ESI) m/z: 404 (M + H$^+$), 426 (M + Na$^+$) | 2-nitrobenzoyl chloride in anhydrous pyridine |
| 10 | 4-[[5-amino-1-(2,6-dimethoxybenzoyl)-1H-1,2,4-triazol-3-yl]amino]-benzenesulfonamide<br>$^1$H NMR (300 MHz, (CD$_3$)$_2$CO) δ 8.65 (s, br, 1H), 7.68 (m, 4H), 7.50 (d, 1H), 7.30 (s, br, 2H), 6.72 (d, 1H), 6.68 (dd, 1H), 6.35 (s, br, 2H), 3.92 (s, 3H), 3.85 (s, 3H); MS (ESI) m/z: 419 (M + H$^+$), 441 (M + Na$^+$) | 2,6-dimemoxybenzoyl chloride in anhydrous pyridine |
| 11 | 4-[[5-amino-1-(2,4,6-trimethylbenzoyl)-1H-1,2,4-triazol-3-yl]amino]-benzenesulfonamide<br>$^1$H NMR (300 MHz, (CD$_3$)$_2$CO) δ 8.78 (s, 1H), 7.78 (s, 2H), 7.72–7.43 (m, 5H), 7.75–6.78 (m, 3H), 6.35 (s, 2H), 2.38–2.16 (m, 9H); MS (ESI) m/z: 401 (M + H$^+$), 423 (M + Na$^+$) | 2,4,6-trimethylbenzoyl chloride in anhydrous pyridine |
| 12 | 4-[(5-amino-1-benzoyl-1H-1,2,4-triazol-3-yl)amino]-benzenesulfonamide<br>$^1$H NMR (300 MHz, (CD$_3$)$_2$CO) δ 8.80 (s, 1H), 8.28 (d, 2H), 7.80–7.58 (m, 7H), 7.52 (s, 2H), 6.38 (s, 2H); MS (ESI) m/z: 359 (M + H$^+$), 381 (M + Na$^+$) | Benzoyl chloride in anhydrous pyridine |
| 14 | 4-[[5-amino-1-(2-thienylcarbonyl)-1H-1,2,4-triazol-3-yl]amino]-benzenesulfonamide<br>$^1$H NMR (300 MHz, (CD$_3$)$_2$CO) δ 8.92 (s, 1H), 8.40 (dd, 1H), 8.12 (dd, 1H), 7.88 (q, 4H), 7.50 (s, 2H), 7.32 (t, 1H), 6.45 (s, 2H); MS (ESI) m/z: 365 (M + H$^+$), 387 (M + Na$^+$) | Thiophene-2-carboxylic acid mediated by DIC/HOBt (1-hydroxybenzo triazole) in anhydrous DMF |
| 15 | 4-[[5-amino-1-[(3-methyl-2-thienyl)carbonyl]-1H-1,2,4-triazol-3-yl]amino]-benzenesulfonamide<br>m.p. 280–284° C.; $^1$H NMR (300 MHz, (CD$_3$)$_2$SO) δ 9.88 (s, 1H), 8.05 (d, 1H), 7.88 (s, 2H), 7.78 (q, 4H), 7.15 (m, 3H), 2.62 (s, 3H);<br>(CD$_3$)$_2$CO δ 8.92 (s, 1H), 7.98 (d, 1H), 7.90 (q, 4H), 7.45 (s, 2H), 7.15 (d, 1H), 6.42 (s, 2H), 2.68 (s, 3H);<br>$^{13}$C NMR (300 MHz, (CD$_3$)$_2$SO) δ 160.6, 157.9, 157.4, 157.2, 150.9, 143.9, 136.0, 135.5, 131.8, 127.3, 124.3, 116.3, 18.1; MS (ESI) m/z: 379 (M + H$^+$), 401 (M + Na$^+$) | 3-methyl-thiophene-2-carboxylic acid mediated by DIC/HOBt in anhydrous DMF |

-continued

| Cpd | Name/Data | Starting Mat'l |
|---|---|---|
| 16 | 4-[[5-amino-1-[(3-fluoro-2-thienyl)carbonyl]-1H-1,2,4-triazol-3-yl]amino]-benzenesulfonamide<br>$^1$H NMR (300 MHz, (CD$_3$)$_2$SO) δ 9.92 (s, br, 1H), 8.18 (t, 1H), 7.92 (s, br, 2H), 7.78 (q, 4H), 7.25 (d, 1H), 7.18 (s, br, 2H); MS (ESI) m/z: 383 (M + H$^+$), 405 (M + Na$^+$) | 3-fluorothiophene-2-carboxylic acid (prepared according to E. C. Taylor and P. Zhou, Org. Prep. Proced. Int., 1997, 29, 221) mediated by DIC/HOBt in anhydrous DMF |
| 17 | 4-[[5-amino-1-[(3-chloro-2-thienyl)carbonyl]-1H-1,2,4-triazol-3-yl]amino]-benzenesulfonamide<br>$^1$H NMR (300 MHz, (CD$_3$)$_2$SO) δ 9.92 (s, br, 1H), 8.25 (d, 1H), 7.95 (s, br, 2H), 7.78 (q, 4H), 7.32 (d, 1H), 7.18 (s, br, 2H); MS (ESI) m/z: 399 (M + H$^+$), 421 (M + Na$^+$) | 3-chlorothiophene-2-carboxylic acid mediated by EDCI/HOBt in anhydrous DMF |
| 18 | 4-[[5-amino-1-[(3-ethoxy-2-thienyl)carbonyl]-1H-1,2,4-triazol-3-yl]amino]-benzenesulfonamide<br>$^1$H NMR (300 MHz, (CD$_3$)$_2$SO) δ 9.85 (s, br, 1H), 8.08 (d, 1H), 7.85–7.75 (m, 6H), 7.28 (d, 1H), 7.15 (s, br, 2H); MS (ESI) m/z: 409 (M + H$^+$), 431 (M + Na$^+$) | 3-ethoxythiophene-2-carboxylic acid mediated by DIC/HOBt in anhydrous DMF |
| 19 | N-[2-[[5-amino-3-[[4-(aminosulfonyl)phenyl]amino]-1H-1,2,4-triazol-1-yl]carbonyl]-3-thienyl]-acetamide<br>$^1$H NMR (300 MHz, (CD$_3$)$_2$SO) δ 11.0 (s, br, 1H), 9.92 (s, br, 1H), 8.18 (q, 2H), 7.85 (s, br, 2H), 7.78 (q, 4H), 7.15 (s, br, 2H), 2.20 (s, 3H); MS (ESI) m/z: 421 (M + H$^+$), 444 (M + Na$^+$) | 3-(acetylamino)-thiophene-2-carboxylic acid mediated by DIC/HOBt in anhydrous DMF |
| 20 | 4-[[5-amino-1-[(5-methyl-2-thienyl)carbonyl]-1H-1,2,4-triazol-3-yl]amino]-benzenesulfonamide<br>$^1$H NMR (300 MHz, (CD$_3$)$_2$SO) δ 9.92 (s, br, 1H), 8.15 (d, 1H), 7.85 (s, br, 2H), 7.78 (q, 4H), 7.20 (s, br, 2H), 7.08 (d, 1H), 2.62 (s, 3H); MS (ESI) m/z: 379 (M + H$^+$) | 5-methyl-thiophene-2-carboxylic acid mediated by DIC/HOBt in anhydrous DMF |
| 21 | 4-[[5-amino-1-[(5-bromo-2-thienyl)carbonyl]-1H-1,2,4-triazol-3-yl]amino]-benzenesulfonamide<br>$^1$H NMR (300 MHz, (CD$_3$)$_2$SO) δ 9.98 (s, br, 1H), 8.05 (d, 1H), 7.95 (s, br, 2H), 7.78 (q, 4H), 7.48 (d, 1H), 7.20 (s, br, 2H); MS (ESI) m/z: 444 (M + H$^+$) | 5-bromothiophene-2-carboxylic acid mediated by DIC/HOBt in anhydrous DMF |
| 22 | 4-[[1-[(5-acetyl-2-thienyl)carbonyl]-5-amino-1H-1,2,4-triazol-3-yl]amino]-benzenesulfonamide<br>$^1$H NMR (300 MHz, (CD$_3$)$_2$SO) δ 10.02 (s, br, 1H), 8.28 (d, 1H), 8.02 (d, 1H), 7.95 (s, br, 2H), 7.75 (q, 4H), 7.20 (s, br, 2H), 2.65 (s, 3H); MS (ESI) m/z: 407 (M + H$^+$), 429 (M + Na$^+$) | 5-acetylthiophene-2-carboxylic acid mediated by DIC/HOBt in anhydrous DMF |
| 25 | 4-[[5-amino-1-(2-furanylcarbonyl)-1H-1,2,4-triazol-3-yl]amino]-benzenesulfonamide<br>$^1$H NMR (300 MHz, (CD$_3$)$_2$CO) δ 8.87 (s, 1H), 8.20 (d, 1H), 8.02 (dd, 1H), 7.85 (q, 4H), 7.48 (s, 2H), 6.88 (dd, 1H), 6.42 (s, 2H); MS (ESI) m/z: 349 (M + H$^+$), 371 (M + Na$^+$) | 2-furoyl chloride in anhydrous pyridine |
| 26 | 4-[[5-amino-1-(5-isoxazolylcarbonyl)-1H-1,2,4-triazol-3-yl]amino]-benzenesulfonamide<br>$^1$H NMR (300 MHz, (CD$_3$)$_2$SO) δ 9.95 (s, br, 1H), 8.92 (d, 1H), 8.00 (s, br, 2H), 7.78 (d, 2H), 7.68 (m, 3H), 7.15 (s, br, 2H); MS (ESI) m/z: 350 (M + H$^+$), 372 (M + Na$^+$) | isoxazole-5-carboxylic acid mediated by DIC/HOBt in anhydrous DMF |
| 27 | 4-[[5-amino-1-(2-pyridinylcarbonyl)-1H-1,2,4-triazol-3-yl]amino]-benzenesulfonamide<br>$^1$H NMR (300 MHz, (CD$_3$)$_2$SO) δ 9.75 (s, 1H), 8.72 (d, 1H), 8.00 (m, 2H), 7.90 (s, br, 2H), 7.68–7.48 (m, 5H), 7.10 (s, br, 2H); MS (ESI) m/z: 360 (M + H$^+$), 382, (M + Na$^+$) | picolic acid mediated by DIC/HOBt in anhydrous DMF |
| 28 | 4-[[5-amino-1-(3-pyridinylcarbonyl)-1H-1,2,4-triazol-3-yl]amino]-benzenesulfonamide<br>$^1$H NMR (300 MHz, (CD$_3$)$_2$SO) δ 9.82 (s, 1H), 9.22 (d, 1H), 8.78 (dd, 1H), 8.45 (dd, 1H), 7.92 (s, br, 2H), 77.62 (q, 4H), 7.15 (s, br, 2H); MS (ESI) m/z: 360 (M + H$^+$), 382, (M + Na$^+$) | nicotinic acid mediated by DIC/HOBt in anhydrous DMF |
| 29 | 4-[[5-amino-1-(4-pyridinylcarbonyl)-1H-1,2,4-triazol-3-yl]amino]-benzenesulfonamide<br>$^1$H NMR (300 MHz, (CD$_3$)$_2$SO) δ 9.80 (s, 1H), 8.82 (d, 2H), 8.00–7.90 (m, 4H), 7.60 (q, 4H), 7.12 (s, br, 2H); MS (ESI) m/z: 360 (M + H$^+$), 382, (M + Na$^+$) | isonicotinic acid mediated by DIC/HOBt in anhydrous DMF |
| 30 | 4-[[5-amino-1-(3-thienylcarbonyl)-1H-1,2,4-triazol-3-yl]amino]-benzenesulfonamide<br>$^1$H NMR (300 MHz, (CD$_3$)$_2$CO) δ 9.08 (d, 1H), 8.85 (s, br, 1H), 7.98 (dd, 1H), 7.82 (q, 4H), 7.62 (dd, 1H), 7.48 (s, br, 1H), 6.45 (s, br, 2H); MS (ESI) m/z: 365 (M + H$^+$), 387 (M + Na$^+$) | thiophene-3-carboxylic acid mediated by DIC/HOBt in anhydrous DMF |

-continued

| Cpd | Name/Data | Starting Mat'l |
|---|---|---|
| 31 | 4-[[5-amino-1-(benzo[b]thien-2-ylcarbonyl)-1H-1,2,4-triazol-3-yl]amino]-benzenesulfonamide<br>$^1$H NMR (300 MHz, (CD$_3$)$_2$SO) δ 9.95 (s, br, 1H), 8.85 (s, 1H), 8.15 (dd, 2H), 8.02 (s, br, 2H), 7.85 (q, 4H), 7.55 (m, 2H), 7.18 (s, br, 2H); MS (ESI) m/z: 415 (M + H$^+$) | benzo[b]thiophene-2-carboxylic acid mediated by DIC/HOBt in anhydrous DMF |
| 34 | 4-[[5-amino-1-[(2,4-dimethyl-5-thiazolyl)carbonyl]-1H-1,2,4-triazol-3-yl]amino]-benzenesulfonamide<br>$^1$H NMR (300 MHz, (CD$_3$)$_2$SO) δ 9.88 (s, br, 1H), 7.90 (s, br, 2H), 7.78 (q, 4H), 7.15 (s, br, 2H), 2.78 (s, 6H); MS (ESI) m/z: 394 (M + H$^+$), 416 (M + Na$^+$) | 2,4-dimethylthiazole-5-carboxylic acid mediated by DIC/HOBt in anhydrous DMF |
| 35 | 4-[[5-amino-1-[(3-bromo-2-thienyl)carbonyl]-1H-1,2,4-triazol-3-yl]amino]-benzenesulfonamide<br>$^1$H NMR (300 MHz, (CD$_3$)$_2$SO) δ 9.95 (s, 1H), 8.23 (d, J = 5.3, 1H), 7.95 (s, 2H), 7.77 (s, 4H), 7.39 (d, J = 5.3, 1H), 7.16 (s, 2H); MS (ESI) m/z: 444.9 (M + H), 466.9 (M + Na$^+$) | 3-bromomiophene-2-carboxylic acid mediated by DIC/HOBt in anhydrous DMF |
| 36 | 4-[[5-amino-1-[(4-methyl-1,2,3-thiadiazol-5-yl)carbonyl]-1H-1,2,4-triazol-3-yl] amino]-benzenesulfonamide<br>$^1$H NMR (300 MHz, (CD$_3$)$_2$SO) δ 10.07 (s, 1H), 8.09 (s, 2H), 7.86 (d, J = 8.8, 2H), 7.72 (d, J = 8.9, 2H), 7.21(s, 2H), 3.02 (s, 3H); MS (ESI) m/z: 381.0 (M + H), 403.0 (M + Na$^+$) | 4-methyl-1,2,3-thiadiazol-5-carboxylic acid mediated by DIC/HOBt in anhydrous DMF |
| 37 | 4-[[5-amino-1-(1,2,3-thiadiazol-4-ylcarbonyl)-1H-1,2,4-triazol-3-yl]amino]-benzenesulfonamide<br>$^1$H NMR (300 MHz, (CD$_3$)$_2$SO) δ 10.18 (s, 1H), 9.93 (s, 1H), 8.05 (s, 2H), 7.76 (d, J = 8.8, 2H), 7.63(d, J = 8.8, 2H), 7.16 (s, 2H); MS(ESI) m/z: 367.0 (M + H), 389.0 (M + Na$^+$) | 1,2,3-thiadiazole-4-carboxylic acid mediated by DIC/HOBt in anhydrous DMF |
| 38 | 4-[[5-amino-1-(cyclopentylcarbonyl)-1H-1,2,4-triazol-3-yl]amino]-benzenesulfonamide<br>$^1$H NMR (300 MHz, (CD$_3$)$_2$SO) δ 9.73 (s, 1H), 7.69 (s, 4H), 7.65 (s, 2H), 7.13 (s, 2H), 1.78 (m, 3H), 1.65 (m, 6H); MS (ESI) m/z: 351.0 (M + H), 373.0 (M + Na$^+$) | cyclopetanecarboxylic acid mediated by DIC/HOBt in anhydrous DMF |
| 39 | 4-[[5-amino-1-(cyclohexylcarbonyl)-1H-1,2,4-triazol-3-yl]amino]-benzenesulfonamide<br>$^1$H NMR (300 MHz, (CD$_3$)$_2$SO) δ 9.76 (s, 1H), 7.69 (s, 4H), 7.66 (s, 2H), 7.13 (s, 2H), 1.98 (s, 2H), 1.80 (s, 2H), 1.69 (d, 1H), 1.36 (m, 6H); MS (ESI) m/z: 365.0 (M + H), 387.1 (M + Na$^+$) | cyclohexanecarboxylic acid mediated by DIC/HOBt in anhydrous DMF |
| 40 | 4-[[5-amino-1-(2-thienylacetyl)-1H-1,2,4-triazol-3-yl]amino]-benzenesulfonamide<br>$^1$H NMR (300 MHz, (CD$_3$)$_2$SO) δ 9.80 (s, 1H), 7.73 (d, J = 1.2, 4H), 7.69 (s, 2H), 7.45 (dd, J = 1.5, 1H), 7.16 (s, 2H), 7.08 (d, J = 2.7, 1H), 7.01 (t, J = 5.1, 1H), 4.52 (s, 2H); MS (ESI) m/z: 379.0 (M + H), 400.9 (M + Na$^+$) | 2-thiopheneacetic acid mediated by DIC/HOBt in anhydrous DMF |
| 42 | 4-[[5-amino-1-[(2E)-1-oxo-3-(2-thienyl)-2-propenyl]-1H-1,2,4-triazol-3-yl]amino]-benzenesulfonamide<br>$^1$H NMR (300 MHz, (CD$_3$)$_2$SO) δ 9.82 (s, 1H), 7.92 (d, J = 8.3, 1H), 7.72 (s, 4H), 7.35 (d, J = 15.8, 2H), 7.26 (d, J = 19.5, 3H), 7.15 (s, 2H), 6.26 (s, 1H); MS (ESI) m/z: 391.0 (M + H), 412.9 (M + Na$^+$) | 3-(2-thienyl)acrylic acid mediated by DIC/HOBt in anhydrous DMF |
| 43 | 4-[[5-amino-1-[(2,6-difluorophenyl)acetyl]-1H-1,2,4-triazol-3-yl]amino]-benzenesulfonamide<br>$^1$H NMR (300 MHz, (CD$_3$)$_2$SO) δ 9.81 (s, 1H), 7.69 (s, 6H), 7.44 (t, J = 16.6, 1H), 7.16 (s, 3H), 4.37 (s, 2H); MS (ESI) m/z: 409.0 (M + H), 431.0 (M + Na$^+$) | 2,6-difluorophenyl acetic acid mediated by DIC/HOBt in anhydrous DMF |
| 44 | 4-[[5-amino-1-[(2E)-3-(2,6-difluorophenyl)-1-oxo-2-propenyl]-1H-1,2,4-triazol-3-yl]amino]-benzenesulfonamide<br>$^1$H NMR (300 MHz, (CD$_3$)$_2$SO) δ 9.86 (s, 1H), 7.85 (d, J = 4.7, 2H), 7.71 (s, 4H), 7.31 (m, 4H), 7.16 (s, 2H), 6.31 (s, 1H); MS (ESI) m/z: 421.0 (M + H), 442.9 (M + Na$^+$) | 2,6-difluoro cinnamic acid mediated by DIC/HOBt in anhydrous DMF |
| 45 | 4-[[5-amino-1-(cycloheptylcarbonyl)-1H-1,2,4-triazol-3-yl]amino]-benzenesulfonamide<br>$^1$H NMR (300 MHz, (CD$_3$)$_2$SO) δ 9.75 (s, 1H), 7.69 (s, 4H), 7.66 (s, 2H), 7.12 (s, 2H), 2.00 (d, J = 11.7, 2H), 1.77 (d, J = 10.5, 2H), 1.40 (m, 3H), 1.07 (m, 2H), 0.91 (d, J = 6.4, 4H); MS (ESI) m/z: 254, 379.0 (M + H), 401.0 (M + Na$^+$) | cycloheptanecarboxylic acid mediated by DIC/HOBt in anhydrous DMF |
| 46 | 4-[[5-amino-1-[(4-methylcyclohexyl)carbonyl]-1H-1,2,4-triazol-3-yl]amino]-benzenesulfonamide<br>$^1$H NMR (300 MHz, (CD$_3$)$_2$SO) δ 9.75 (s, 1H), 7.69 (s, 4H), 7.66 (s, 2H), 7.12 (s, 2H), 2.00 (d, J = 11.7, 2H), 1.77 | trans-4-methyl-1-cyclohexanecarboxylic acid mediated by DIC/HOBt in |

-continued

| Cpd | Name/Data | Starting Mat'l |
|---|---|---|
| | (d, J = 10.5, 2H), 1.40 (m, 3H), 1.07 (m, 2H), 0.91 (d, J = 6.4, 4H); MS (ESI) m/z: 254, 379.0 (M + H), 401.0 (M + Na$^+$) | anhydrous DMF |
| 47 | 4-[[5-amino-1-[(2-methylcyclohexyl)carbonyl]-1H-1,2,4-triazol-3-yl]amino]-benzenesulfonamide<br>$^1$H NMR (300 MHz, (CD$_3$)$_2$SO) δ 9.75 (s, 1H), 7.68 (s, 4H), 7.66 (s, 2H), 7.13 (s, 2H), 1.55 (m, 9H), 0.85 (d, J = 6.0, 4H); MS (ESI) m/z: 254, 379.0 (M + H), 401.0 (M + Na$^+$) | 2-methyl-1-cyclohexanecarboxylic acid mediated by DIC/HOBt in anhydrous DMF |
| 48 | 4-[[5-amino-1-[(4-butylcyclohexyl)carbonyl]-1H-1,2,4-triazol-3-yl]amino]-benzenesulfonamide<br>$^1$H NMR (300 MHZ, (CD$_3$)$_2$SO) δ 9.75 (S, 1H), 7.68 (S, 4H), 7.66 (S, 2H), 7.12 (S, 2H), 2.02 (D, J = 11.3, 2H), 1.82 (D, J = 9.9, 2H), 1.40 (D, J = 11.3, 2H), 1.25 (S, 7H), 1.02 (M, 4H), 0.87 (S, 4H). MS (ESI) M/Z: 254, 435.1 (M + H), 457.1 (M + NA$^+$) | trans-4-butyl-1-cyclohexanecarboxylic acid mediated by DIC/HOBt in anhydrous DMF |
| 49 | 4-[[5-amino-1-[[5-(2-pyridinyl)-2-thienyl]carbonyl]-1H-1,2,4-triazol-3-yl]amino]-benzenesulfonamide<br>$^1$H NMR (300 MHz, (CD$_3$)$_2$SO) δ 9.98 (s, 1H), 8.65 (d, 1H), 8.25 (d, 1H), 8.08 (d, 1H), 8.02–7.75 (m, 8H), 7.42 (dd, 1H), 7.20 (s, 2H). MS (ESI) m/z: 442 (M + H$^+$), 464 (M + Na$^+$) | 5-(2-pyridyl)-thiophene-2-carboxylic acid mediated by DIC/HOBt in anhydrous DMF |
| 50 | 4-[[5-amino-1-[[3-(1H-pyrrol-1-yl)-2-thienyl]carbonyl]-1H-1,2,4-triazol-3-yl]amino]-benzenesulfonamide<br>$^1$H NMR (300 MHz, (CD$_3$)$_2$SO) δ 9.85 (s, 1H), 8.18 (d, 1H), 7.85–7.70 (m, 6H), 7.32 (d, 1H), 7.18 (s, 2H), 7.12 (t, 2H), 6.20 (t, 2H). MS (ESI) m/z: 430 (M + H$^+$) | 3-(1H-pyrrol-1-yl)-thiophene-2-carboxylic acid mediated by DIC/HOBt in anhydrous DMF |
| 51 | 4-[[5-amino-1-[[5-(1,1-dimethylethyl)-2-thienyl]carbonyl]-1H-1,2,4-triazol-3-yl]amino]-benzenesulfonamide<br>$^1$H NMR (300 MHz, (CD$_3$)$_2$CO) δ 8.95 (s, 1H), 8.25 (d, 1H), 7.95 (d, 2H), 7.85 (d, 2H), 7.50 (s, 2H), 7.18 (d, 1H), 6.48 (s, 2H), 1.55 (s, 9H). MS (ESI) m/z: 421 (M + H$^+$), 443 (M + Na$^+$) | 5-tert-butylthiophene-2-carboxylic acid mediated by DIC/HOBt in anhydrous DMF |
| 52 | 3-[5-[[5-amino-3-[[4-(aminosulfonyl)phenyl]amino]-1H-1,2,4-triazol-1-yl]carbonyl]-2-thienyl]-(2E)-2-propenoic acid-1,1-dimethylethyl ester<br>$^1$H NMR (300 MHz, (CD$_3$)$_2$SO) δ 9.95 (s, 1H), 8.22 (d, 1H), 7.95 (s, 2H), 7.82–7.68 (m, 6H), 7.15 (s, 2H), 6.52 (d, 1H), 1.52 (s, 9H). MS (ESI) m/z: 491 (M + H$^+$), 513 (M + Na$^+$)<br>5-(2-tert-butoxycarbonyl-vinyl)-thiophene-2-carboxylic acid (intermediate)$^1$H NMR (300 MHz, (CD$_3$)$_2$CO) δ 7.80–70 (m, 2H), 7.48 (d, 1H), 7.32 (d, 1H), 1.50 (s, 9H); MS (ESI) m/z: 253 (M-H$^+$), 209 (M-H$^+$—CO$_2$) | 5-(2-tert-butoxycarbonyl-vinyl)-thiophene-2-carboxylic acid (prepared by Heck reaction of 5-bromothiophene-2-carboxylic acid and t-butyl acrylate) mediated by DIC/HOBt in anhydrous DMF |
| 53 | 4-[[5-amino-1-[[5-(phenylethynyl)-2-thienyl]carbonyl]-1H-1,2,4-triazol-3-yl]amino]-benzenesulfonamide<br>$^1$H NMR (300 MHz, (CD$_3$)$_2$SO) δ 9.98 (s, 1H), 8.20 (d, 1H), 7.95 (s, 2H), 7.78 (m, 4H), 7.62 (m, 2H), 7.60 (d, 1H), 7.45 (m, 3H), 7.18 (s, 2H). MS (ESI) m/z: 465 (M + H$^+$), 487 (M + Na$^+$)<br>5-phenylethynyl-thiophene-2-carboxylic acid (intermediate) $^1$H NMR (300 MHz, (CD$_3$)$_2$CO) δ 7.98 (d, 1H), 7.58 (m, 2H), 7.45 (m, 3H), 7.35 (d, 1H); MS (ESI) m/z: 229 (M + H$^+$) | 5-phenylethynyl-thiophene-2-carboxylic acid (intermediate prepared by oxidation of 5-phenylethynyl-thiophene-2-carboxaldehyde), mediated by DIC/HOBt in anhydrous DMF |
| 54 | 4-[[5-amino-1-(2,6-difluoro-3-nitrobenzoyl)-1H-1,2,4-triazol-3-yl]amino]-benzenesulfonamide<br>$^1$H NMR (300 MHz, (CD$_3$)$_2$CO) δ 8.90 (s, 1H), 8.55 (m, 1H), 7.75–7.50 (m, 7H), 6.25 (s, 2H); MS (ESI) m/z: 440 (M + H$^+$), 462 (M + Na$^+$) | 2,6-difluoro-3-nitro-benzoic acid mediated by DIC/HOBt in anhydrous DMF |
| 55 | 4-[[5-amino-1-(3-amino-2,6-difluorobenzoyl)-1H-1,2,4-triazol-3-yl]amino]-benzenesulfonamide<br>$^1$H NMR (300 MHz, CD$_3$OD) δ 7.68 (d, 2H), 7.45 (d, 2H), 6.95 (m, 1H), 6.85 (m, 1H); MS (ESI) m/z: 410 (M + H$^+$), 432 (M + Na$^+$) | catalytic hydrogenation of compound 54 in methanol by catalysis of 10% palladium on charcoal |
| 56 | 4-[[5-amino-1-(2,6-dimethylbenzoyl)-1H-1,2,4-triazol-3-yl]amino]-benzenesulfonamide<br>$^1$H NMR (300 MHz, (CD$_3$)$_2$CO) δ 8.75 (s, 1H), 7.65–7.28 | 2,6-dimethylbenzoic acid mediated by |

-continued

| Cpd | Name/Data | Starting Mat'l |
|---|---|---|
|  | (m, 7H), 7.15 (d, 2H), 6.32 (s, 2H), 2.25 (s, 6H); MS (ESI) m/z: 387 (M + H⁺), 409 (M + Na⁺) | DIC/HOBt in anhydrous DMF |
| 57 | 4-[[5-amino-1-(2-methylbenzoyl)-1H-1,2,4-triazol-3-yl]amino]-benzenesulfonamide<br>$^1$H NMR (300 MHz, (CD$_3$)$_2$CO) δ 8.75 (s, 1H), 7.72–7.25 (m, 10H), 6.35 (s, 2H), 2.45 (s, 3H); MS (ESI) m/z: 373 (M + H⁺), 395 (M + Na⁺) | 2-methylbenzoyl chloride in anhydrous pyridine |
| 66 | 5-amino-3-[[4-(aminosulfonyl)phenyl]amino]-N-(2,6-difluorophenyl)-1H-1,2,4-triazole-1-carbothioamide<br>$^1$H NMR (300 MHz, (CD$_3$)$_2$CO) δ 10.40 (s, 1H), 8.90 (s, 1H), 8.15 (s, 2H), 7.85 (d, 2H), 7.75 (d, 2H), 7.40 (m, 1H), 7.15 (m, 2H), 6.35 (s, 2H), 5.75 (s, 2H); MS (ESI) m/z: 426 (M + H⁺), 448 (M + Na⁺) | 2,6-difluorophenyl isothiocyanate in anhydrous pyridine |
| 67 | 5-amino-3-[[4-(aminosulfonyl)phenyl]amino]-N-(2,6-difluorophenyl)-1H-1,2,4-triazole-1-carboxamide<br>$^1$H NMR (300 MHz, (CD$_3$)$_2$CO) δ 9.15 (s, 1H), 8.80 (s, 1H), 7.80 (d, 2H), 7.70 (d, 2H), 7.42 (m, 1H), 7.15 (m, 2H), 7.00 (s, 2H), 6.35 (s, 2H); MS (ESI) m/z: 410 (M + H⁺), 432 (M + Na⁺) | 2,6-difluorophenyl isocyanate in anhydrous DMF |
| 68 | 4-[[5-amino-1-[(2,6-difluorophenyl)sulfonyl]-1H-1,2,4-triazol-3-yl]amino]-benzenesulfonamide<br>$^1$H NMR (300 MHz, (CD$_3$)$_2$CO) δ 8.80 (s, 1H), 7.85 (m, 1H), 7.75 (d, 2H), 7.65 (d, 2H), 7.30 (t, 2H), 6.95 (s, 2H), 6.35 (s, 2H); MS (ESI) m/z: 431 (M + H⁺), 453 (M + Na⁺) | 2,6-difluorobenzenesulfonyl chloride in anhydrous pyridine |
| 69 | 4-[[5-amino-1-(2-chloro-6-fluoro-3-methylbenzoyl)-1H-1,2,4-triazol-3-yl]amino]-benzenesulfonamide<br>$^1$H NMR (300 MHz, (CD$_3$)$_2$SO) δ 9.85 (s, 1H), 8.05 (s, 2H), 7.64–7.55 (m, 3H), 7.45–7.35 (m, 3H), 7.10 (s, 2H), 2.38 (s, 3H); MS (ESI) m/z: 425 (M + H⁺), 447 (M + Na⁺) | 2-chloro-6-fluoro-3-methylbenzoyl chloride in anhydrous pyridine |
| 70 | 4-[[5-amino-1-(2-chloro-6-fluorobenzoyl)-1H-1,2,4-triazol-3-yl]amino]-benzenesulfonamide<br>$^1$H NMR (300 MHz, (CD$_3$)$_2$SO) δ 9.87 (s, 1H), 8.05 (s, 2H), 7.68–7.63 (m, 1H), 7.57–7.50 (m, 3H), 7.48–7.42 (m, 3H), 7.09 (s, 2H); MS (ESI) m/z: 411 (M + H⁺), 433 (M + Na⁺) | 2-chloro-6-fluorobenzoyl chloride in anhydrous pyridine |
| 78 | 4-[[5-amino-1-(3-chloro-2,6-difluorobenzoyl)-1H-1,2,4-triazol-3-yl]amino]-benzenesulfonamide<br>$^1$H NMR (300 MHz, (CD$_3$)$_2$SO) δ 9.89 (s, 1H), 8.07 (s, 2H), 8.00–7.92 (m, 1H), 7.59 (d, 2H), 7.49–7.44 (m, 3H), 7.12 (s, 2H); MS (ESI) m/z: 429 (M + H⁺) | 3-chloro-2,6-difluorobenzoic acid, mediated by DIC/HOBt in anhydrous DMF |
| 122 | 4-[[3-amino-1-(2,6-difluorobenzoyl)-1H-1,2,4-triazol-5-yl]amino]-benzenesulfonamide<br>(minor regioisomer of Cpd 1) $^1$H NMR (300 MHz, CD$_3$CN) δ 9.90 (s, 1H), 7.90 (q, 4H), 7.60 (m, 1H), 7.15 (t, 2H), 5.62 (s, 2H), 4.85 (s, 2H); MS (ESI) m/z: 395 (M + H⁺), 417 (M + Na⁺) | 2,6-difluorobenzoyl chloride in anhydrous pyridine |
| 123 | 4-[[3-amino-1-(2,6-difluoro-3-methylbenzoyl)-1H-1,2,4-triazol-5-yl]amino]-benzenesulfonamide<br>(minor regioisomer of Cpd 2) $^1$H NMR (300 MHz, ((CD$_3$)$_2$SO) δ 10.0 (s, 1H), 8.00 (d, 2H), 7.78 (d, 2H), 7.50 (m, 1H), 7.20 (m, 2H), 7.15 (t, 2H), 6.25 (s, 2H), 2.28 (s, 3H); MS (ESI) m/z: 409 (M + H⁺), 431 (M + Na⁺) | 2,6-difluorobenzoyl chloride in anhydrous pyridine |
| 128 | 3-amino-5-[[4-(aminosulfonyl)phenyl]amino]-N-(2,6-difluorophenyl)-1H-1,2,4-triazole-1-carbothioamide<br>(minor regioisomer of Cpd 66) $^1$H NMR (300 MHz, (CD$_3$)$_2$CO) δ 12.10 (s, 1H), 10.28 (s, 1H), 7.85 (m, 4H), 7.45 (m, 1H), 7.20 (m, 2H), 6.45 (s, 2H), 5.75 (s, 2H); MS (ESI) m/z: 426 (M + H⁺), 448 (M + Na⁺) | — |

EXAMPLE 2

1-(2,6-difluorobenzoyl)-N$^3$-[4-(1-piperidinylsulfonyl)phenyl]-1H-1,2,4-triazole-3,5-diamine (Cpd 13)

Using the procedure for Example 1, 1-amidino-3,5-dimethylpyrazole nitrate Compound 1C was reacted with 1-(4-isothiocyanatophenylsulfonyl)piperidine Compound 2B to produce Compound 2C. $^1$H NMR (300 MHz, CD$_3$CN) δ 10.75 (s, br, 1H), 8.40 (s, br, 1H), 7.95 (s, br, 1H), 7.55 (q, 4H), 5.95 (s, 1H), 3.00 (m, 4H), 2.25 (s, 6H), 1.68 (m, 4H), 1.45 (m, 2H); MS (ESI) m/z: 421 (M+H⁺). Compound 2C was then reacted with hydrazine to produce Compound 2D. $^1$H NMR (300 MHz, CD$_3$CN) δ 10.75 (s, br, 1H), 7.65 (s, br, 1H), 7.55 (q, 4H), 5.85 (s, br, 2H), 2.82 (m, 4H), 1.55 (m, 4H), 1.32 (m, 2H); MS (ESI) m/z: 323 (M+H⁺). Compound 2D was acylated with 2,6-difluoro-3-methylbenzoyl chloride Compound 1F in anhydrous pyridine to produce Compound 13 (85% yield). $^1$H NMR (300 MHz, CDCl$_3$) δ 7.60–7.50 (m, 3H), 7.42 (d, 2H), 7.18 (t, 2H), 6.98 (s, br, 1H), 6.55 (s, br, 2H), 2.98 (m, 4H), 1.65 (m, 4H), 1.42 (m, 2H); MS (ESI) m/z: 363 (M+H⁺), 485 (M+Na⁺).

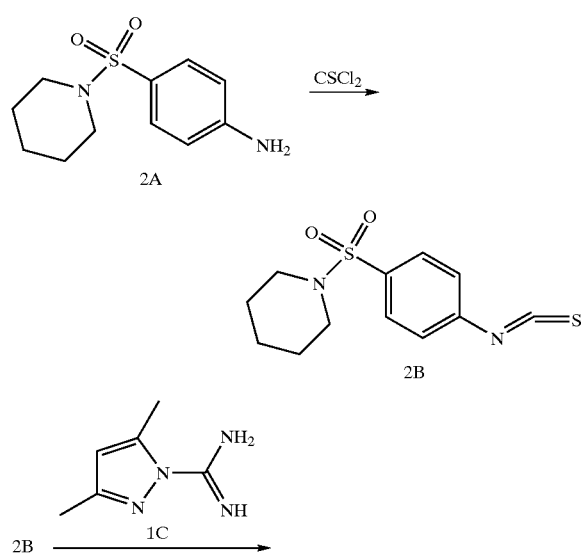

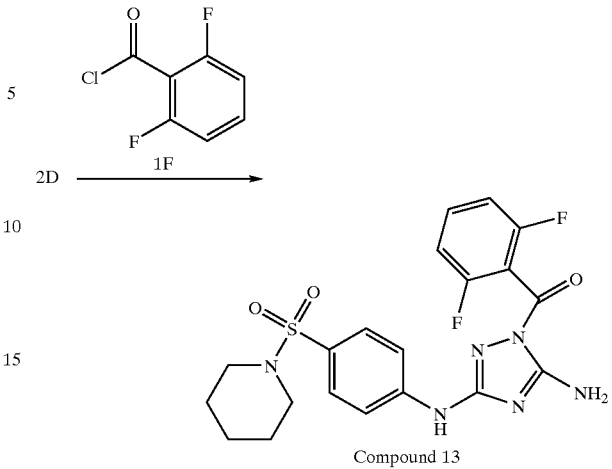

Using the procedure for Example 3, the following compounds were prepared by acylation of the intermediate Compound 2D using the indicated starting material in place of Compound 1F and reagent(s):

| Cpd | Name/Data | Starting Mat'l |
|---|---|---|
| 23 | $N^3$-[4-(1-piperidinylsulfonyl)phenyl]-1-(2-thienylcarbonyl)-1H-1,2,4-triazole-3,5-diamine<br>$^1$H NMR (300 MHz, (CD$_3$)$_2$SO) δ 10.02 (s, br, 1H), 8.40 (dd, 1H), 8.18 (dd, 1H), 7.92 (s, br, 2H), 7.88 (d, 2H), 7.58 (d, 2H), 7.32 (t, 1H), 2.88 (m, 4H), 1.55 (m, 4H), 1.35 (m, 2H); MS (ESI) m/z: 433 (M + H$^+$), 455 (M + Na$^+$) | thiophene-2-carboxylic acid mediated by DIC/HOBt in DMF |
| 24 | 1-[(3-methyl-2-thienyl)carbonyl]-$N^3$-[4-(1-piperidinylsulfonyl)phenyl]-1H-1,2,4-triazole-3,5-diamine<br>$^1$H NMR (300 MHz, (CD$_3$)$_2$SO) δ 10.02 (s, br, 1H), 8.02 (d, 1H), 7.95–7.80 (m, 4H), 7.68 (d, 2H), 7.18 (d, 1H), 2.88 (m, 4H), 2.68 (s, 3H), 1.55 (m, 4H), 1.35 (m, 2H); MS (ESI) m/z: 447 (M + H$^+$), 469 (M + Na$^+$) | 3-methylthiophene-2-carboxylic acid mediated by DIC/HOBt in DMF |

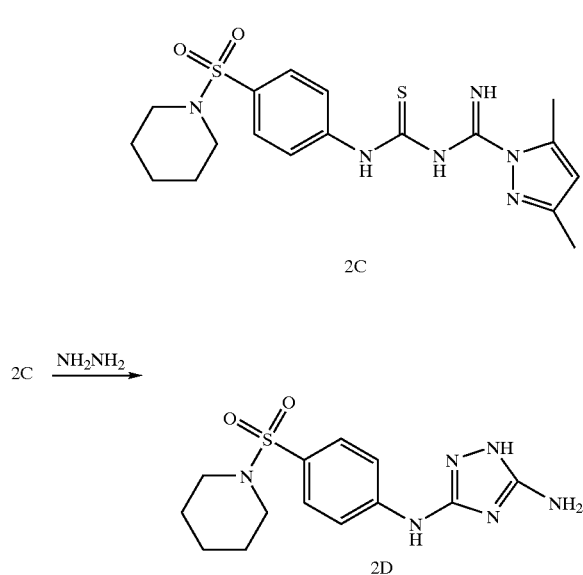

EXAMPLE 3

4-[[5-amino-1-[(5-ethyl-2-thienyl)carbonyl]-1H-1,2,4-triazol-3-yl]amino]-benzenesulfonamide (Cpd 32)

Hydrazine monohydrate (0.97 mL, 1.019 mol) and potassium hydroxide (1.12 g, 20 mmol) were added to a solution of 5-acetyl-thiophene-2-carboxylic acid (1.70 g, 10 mmol) in diethylene glycol (20 mL) and water (1 mL). The reaction mixture was stirred in an oil bath at 110° C. for 16 hrs, cooled to rt, acidified with 2N HCl and then extracted with methylene chloride (4×50 mL). Organic layers were combined, dried, concentrated and subjected to chromatography separation on silica gel (eluted with 10% methanol/methylene chloride) to produce 3-ethylthiophene-2-carboxylic acid Compound 3A as a pale yellow solid (1.161 g, 74%). $^1$H NMR (300 MHz, CD$_3$OD) δ 7.59 (d, J 3.7, 1H), 6.87 (d, J 3.7, 1H), 2.88 (q, J 7.5, 1H), 1.32 (t, J 7.5, 3H); MS (ESI) m/z: 155 (M−H$^+$). Using the procedure of Example 1, Compound 1E was acylated with Compound 3A mediated by DIC/HOBt in anhydrous DMF to produce Compound 32 (59% yield). 1H NMR (300 MHz, (CD$_3$)$_2$CO) δ 8.90 (s, br, 1H), 8.25 (d, 1H), 7.88 (q, 4H), 7.45 (s, br, 2H), 7.10 (d, 1H) 6.45 (s, br, 2H), 3.05 (q, 2H), 1.42 (t, 3H); MS (ESI) m/z: 393 (M+H$^+$), 415 (M+Na$^+$).

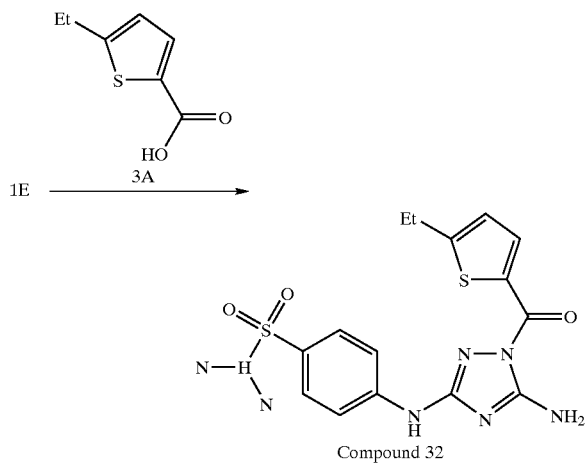

Compound 32

EXAMPLE 4

4-[[5-amino-1-[(3,5-dimethyl-2-thienyl)carbonyl]-1H-1,2,4-triazol-3-yl]amino]-benzenesulfonamide (Cpd 33)

2.2 equivalents of 2.0 M LDA solution in heptane/THF/ethylbenzene (0.97 mL, 1.019 mol) was added to a solution of 3-methylthiophene-2-carboxylic acid (1.42 g, 10 mmol) in anhydrous THF (20 mL) at 0° C. The reaction mixture was stirred at 0° C. for 1.5 hr; and then methyl iodide (1.4 mL, 22 mmol) was added. The resulting mixture was stirred at 0° C. for an additional 2 hr, acidified with 2N HCl and extracted with methylene chloride (4×50 mL). The organic layers were then combined, concentrated and separated via HPLC to give 3,5-dimethylthiophene-2-carboxylic acid Compound 4A as a white powder. $^1$H NMR (300 MHz, CD$_3$OD) δ 6.72 (s, 1H), 2.43 (s, 3H), 2.46 (s, 3H); MS (ESI) m/z: 155 (M−H$^+$). Using the procedure of Example 1, Compound 1E was acylated with Compound 4A mediated by DIC/HOBt in anhydrous DMF to produce Compound 33 (73% yield). $^1$H NMR (300 MHz, (CD$_3$)$_2$SO) δ 9.88 (s, br, 1H), 7.85 (s, br, 2H), 7.78 (q, 4H), 7.18 (s, br, 2H), 6.92 (s, 1H), 2.58 (s, 3H), 2.55 (s, 3H); MS (ESI) m/z: 393 (M+H$^+$), 415 (M+Na$^+$).

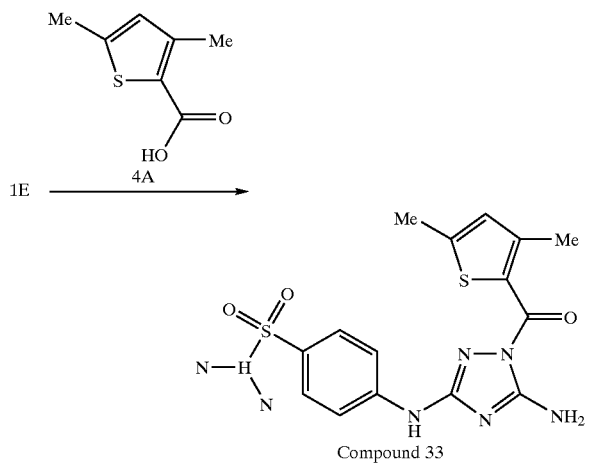

Compound 33

EXAMPLE 5

4-[[5-amino-1-[2,6-difluoro-3-(1-hydroxyethyl)benzoyl]-1H-1,2,4-triazol-3-yl]amino]-benzenesulfonamide (Cpd 58)

2',4'-difluoroacetophenone (5 g, 32 mmol) was reacted with sodium borohydride (1.21 g) in THF (20 mL) and methanol (10 mL) for 1 hr. The resultant mixture was evaporated to dryness and partitioned between methylene chloride and water. The organic layer was separated, dried, and evaporated to give 1-(2',4'-difluorophenyl)-ethanol as a colorless oil (4.86 g, 96%). $^1$H NMR (300 MHz, CDCl$_3$) δ 7.48 (m, 1H), 6.85 (m, 1H), 6.75 (m, 1H), 5.15 (q, 1H), 2.0 (s, 1H), 1.5 (d, 3H). 1-(2',4'-difluorophenyl)-ethanol (5.384 g, 34 mmol), t-butyltrimethylsilyl chloride (6.148 g, 40.8 mmol) and imidazole (5.567 g, 81.8 mmol) in DMF (60 mL) were combined and stirred at rt overnight. The resultant mixture was evaporated to dryness in vacuo, and then the residue was partitioned between methylene chloride and water. The organic layer was separated, dried and evaporated to give 1-(2',4'-difluorophenyl)-ethyl t-butyltrimethylsilyl ether as a white solid (6.88 g, 74%). $^1$H NMR (300 MHz, CDCl$_3$) δ 7.45 (q, 1H), 6.75 (m, 1H), 6.62 (m, 1H), 5.05 (q, 1H), 1.32 (d, 3H), 0.88 (s, 9H), 0.05 and 0.01 (each s, each 3H). A 1.6 M solution of n-butyl lithium in hexane (3.75 mL, 6 mmol) was added dropwise to a solution of 1-(2',4'-difluorophenyl)-ethyl t-butyltrimethylsilyl ether (1.362 g, 5 mmol) in THF (60 mL) at −50° C. and was stirred at the same temperature for 3 h. The reaction mixture was poured to dry ice; and then was evaporated to dryness. The residue was partitioned between methylene chloride and water, acidified with acetic acid. The organic layer was separated, dried, and evaporated to give 2,6-difluoro-3-(1-t-butyltrimethylsilyloxyethyl)-benzoic acid Compound 5A as white solid (1.57 g, 99%). $^1$H NMR (300 MHz, CDCl$_3$) δ 7.70 (q, 1H), 7.00 (t, 1H), 6.00 (br, 1H), 5.15 (q, 1H), 1.40 (d, 3H), 0.90 (s, 9H), 0.12 and 0.05 (each s, each 3H).

Using the procedure of Example 1, Compound 1E was acylated with Compound 5A mediated by DIC/HOBt in anhydrous DMF to provide 4-[[5-amino-1-(2,6-difluoro-3-(1-t-butyltrimethylsilyloxyethyl)-benzoyl)-1H-1,2,4-triazol-3-yl]amino]-benzenesulfonamide Compound 5B (46% yield). $^1$H NMR (300 MHz, CDCl$_3$) δ 7.72 (m, 3H), 7.38 (d, 2H), 7.02 (t, 1H), 6.80 (s, 1H), 6.45 (s, 2H), 5.15 (q, 1H), 4.68 (s,2H), 1.15 (d, 3H), 0.92 (s, 9H), 0.10 (s, 3H), 0.02 (s, 3H); MS (ESI) m/z: 553 (M+H$^+$), 575 (M+Na$^+$). 4-[[5-amino-2-(2,6-difluoro-3-(1-t-butyltrimethylsilyloxyethyl)-benzoyl)-2H-1,2,4-triazol-3-yl]amino]-benzenesulfonamide (a minor regioisomer) was also isolated from the reaction mixture (192 mg, 34%). $^1$H NMR (300 MHz, CDCl$_3$) δ 10.00 (s, 1H), 7.92 (d, 2H), 7.82 (d, 2H), 7.70 (q, 1H), 7.02 (t, 1H), 5.18 (q, 1H), 4.82 (s, 2H), 4.32 (s, 2H), 1.42 (d, 3H), 0.92 (s, 9H), 0.10 (s, 3H), 0.02 (s, 3H); MS (ESI) m/z: 553 (M+H$^+$), 575 (M+Na$^+$).

0.7 mL of 1.0 M TBAF solution in THF was added to a solution of 4-[[5-amino-1-(2,6-difluoro-3-(1-t-butyltrimethylsilyloxyethyl)-benzoyl)-1H-1,2,4-triazol-3-yl]amino]-benzenesulfonamide Compound 5B (193 mg, 0.35 mol) in THF (10 mL). The reaction solution was stirred at rt for 1 hr and evaporated to dryness. The resultant residue was then subjected to column chromatography on silica gel with 20% methanol/methylene chloride to give the product Compound 58 as a white foam (90 mg, 59%). $^1$H NMR (300 MHz, (CD$_3$)$_2$SO) δ 9.85 (s, 1H), 8.00 (s, 2H), 7.75 (m, 1H), 7.55 (m, 2H), 7.45 (m, 2H), 7.30 (t, 1H), 7.10 (m, 2H), 6.80 (s, 1H), 5.55 (d, 1H), 5.00 (m, 1H), 1.38 (d, 3H); MS (ESI) m/z: 421 (M+H$^+$—H$_2$O), 439 (M+H$^+$), 461 (M+Na$^+$).

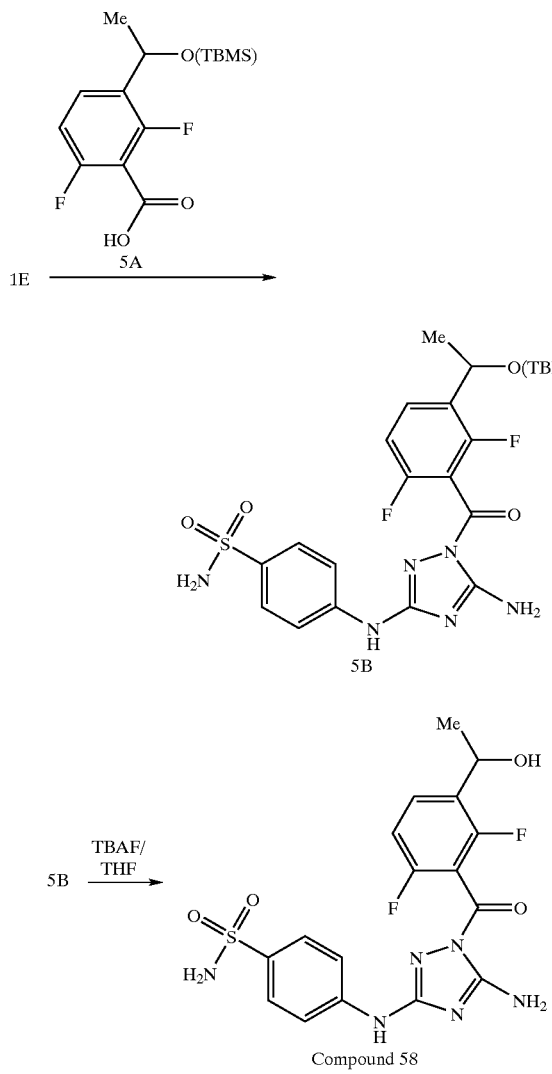
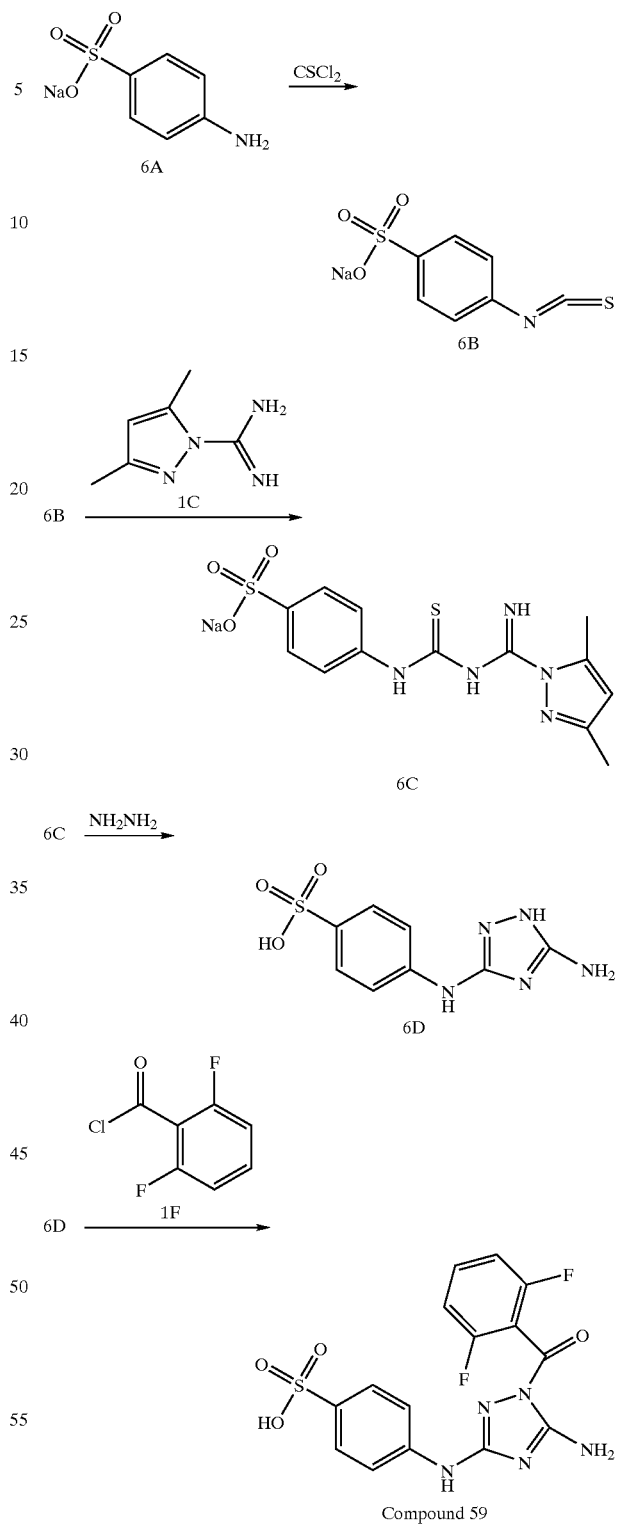

EXAMPLE 6

4-[[5-amino-1-(2,6-difluorobenzoyl)-1H-1,2,4-triazol-3-yl]amino]-benzenesulfonic Acid (Cpd 59)

The sodium salt of 4-sulfophenyl isothiocyanate Compound 6B, (prepared using the procedure of Example 1) was reacted with 1-amidino-3,5-dimethylpyrazole nitrate Compound 1C to produce Compound 6C which was reacted with hydrazine to produce Compound 6D. $^1$H NMR (300 MHz, (CD$_3$)$_2$SO) δ 11.1 (s, 1H), 8.75 (s, 1H), 7.3 (m, 4H), 5.85 (s, 2H); MS (ESI) m/z: 256 (M+H$^+$). Using the procedure of Example 1, Compound 6D was acylated with 2,6-difluorobenzoyl chloride Compound 1F in anhydrous pyridine to produce compound 59 (4% yield). $^1$H NMR (300 MHz, (CD$_3$)$_2$SO) δ 9.35 (s, 1H), 7.95 (s, 2H), 7.82 (m, 2H), 7.45–7.25 (m, 5H); MS (ESI) m/z: 396 (M+H$^+$).

Using the procedure for Example 6, the following compounds were prepared by acylation of the intermediate Compound 6D using the indicated starting material in place of Compound 1F and reagent(s):

| Cpd | Name/Data | Starting Mat'l |
|---|---|---|
| 60 | 4-[[5-amino-1-(2,6-difluoro-3-methylbenzoyl)-1H-1,2,4-triazol-3-yl]amino]-benzenesulfonic acid<br>$^1$H NMR (300 MHz, CD$_3$OD) δ 7.62 (d, 2H), 7.50 (m, 1H), 7.38 (d, 2H), 7.05 (m, 1H), 2.30 (s, 3H); MS (ESI) m/z: 410 (M + H$^+$) | 2,6-difluoro-3-methylbenzoyl chloride in anhydrous pyridine |

EXAMPLE 7

1-(2,6-Difluorobenzoyl)-N$^3$-phenyl-1H-1,2,4-triazole-3,5-diamine (Cpd 61)

3-Anilino-5-amino-1,2,4-triazole Compound 7A (prepared using the procedure of Example 1) was acylated with 2,6-difluorolbenzoyl chloride Compound 1F in anhydrous pyridine to produce Compound 61 as a white solid (61% yield). $^1$H NMR (300 MHz, CDCl$_3$) δ 7.80 (s, 1H), 7.45 (m, 1H), 7.30–7.15 (m, 4H), 7.05–6.85 (m, 5H), 6.70 (s, 2H); MS (ESI) m/z: 316 (M+H$^+$), 338 (M+Na$^+$).

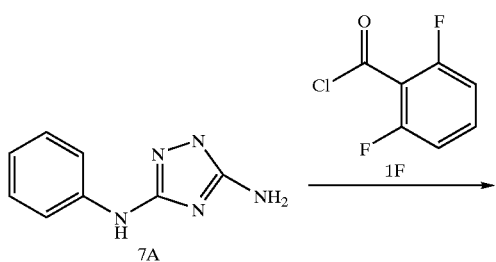

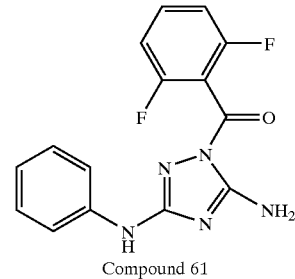

Compound 61

Using the procedure for Example 7, the following compounds were prepared by acylation of Compound 7A using the indicated starting material in place of Compound 1F and reagent(s):

| Cpd | Name/Data | Starting Mat'l |
|---|---|---|
| 62 | 1-benzoyl-N$^3$-phenyl-1H-1,2,4-triazole-3,5-diamine<br>$^1$H NMR (300 MHz, CDCl$_3$) δ 8.30 (s, 2H), 7.65–7.40 (m, 5H), 7.28 (d, 2H), 7.00 (t, 1H), 6.80 (s, 1H), 6.70 (s, 2H); MS (ESI) m/z: 280 (M + H$^+$), 302 (M + Na$^+$) | benzoyl chloride in anhydrous pyridine |
| 65 | 5-amino-N-phenyl-3-(phenylamino)-1H-1,2,4-triazole-1-carboxamide<br>$^1$H NMR (300 MHz, (CD$_3$)$_2$CO) δ 9.20 (s, 1H), 8.20 (s, 1H), 7.70 (m, 4H), 7.35 (t, 2H), 7.25 (t, 2H), 7.15 (t, 1H), 7.98 (s, 2H), 6.88 (t, 1H); MS (ESI) m/z: 295 (M + H$^+$), 317 (M + Na$^+$) | phenyl isocyanate in anhydrous DMF |
| 124 | 1-(2,6-difluorobenzoyl)-N$^5$-phenyl-1H-1,2,4-triazole-3,5-diamine<br>(minor regioisomer of Cpd 61) $^1$H NMR (300 MHz, CDCl$_3$) δ 9.80 (s, 1H), 7.65 (d, 2H), 7.60–7.32 (m, 3H), 7.25–7.00 (m, 3H), 4.40 (s, 2H); MS (ESI) m/z: 316 (M + H$^+$), 338 (M + Na$^+$) | — |
| 125 | 1-benzoyl-N$^5$-phenyl-1H-1,2,4-triazole-3,5-diamine<br>(minor regioisomer of Cpd 62) $^1$H NMR (300 MHz, CDCl$_3$) δ 10.20 (s, 1H), 8.18 (d, 2H), 7.72–7.30 (m, 7H), 7.15 (t, 1H), 4.30 (s, 2H); MS (ESI) m/z: 280 (M + H$^+$), 302 (M + Na$^+$) | — |

EXAMPLE 8

N³-(3-chlorophenyl)-1-(2,6-difluorobenzoyl)-1H-1,2,4-triazole-3,5-diamine (Cpd 63)

3-(3-Chloroanilino)-5-amino-1,2,4-triazole Compound 8A (prepared using the procedure of Example 1) was acylated with 2,6-difluorobenzoyl chloride Compound 1F in anhydrous pyridine to produce Compound 63 as a pale yellow solid (66% yield). 1H NMR (300 MHz, CDCl₃) δ 7.6–7.50 (m, 2H), 7.15–6.80 (m, 6H), 6.60 (s, 2H); MS (ESI) m/z: 350 (M+H⁺), 372 (M+Na⁺).

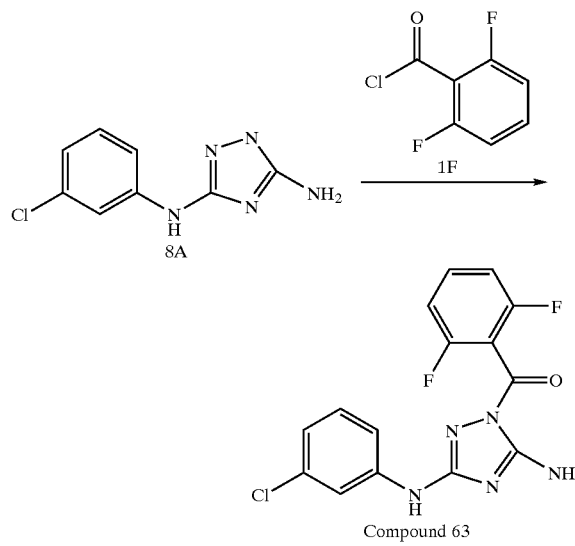

Compound 63

Using the procedure for Example 8, the following compounds were prepared by acylation of the intermediate Compound 8A using the indicated starting material in place of Compound 1F and reagent(s):

EXAMPLE 9

1-(2,6-difluorobenzoyl)-N³-[4-(4-methyl-1-piperazinyl)phenyl]-1H-1,2,4-triazole-3,5-diamine (Cpd 71)

4-(4-Methylpiperazino)-phenyl isothiocyanate was reacted with 1 equivalent of 3,5-dimethylpyrazole-1-carboxamidine nitrate and 1.1 equivalents of potassium t-butoxide in DMSO at 55° C. for 4 hours. 10 equivalents of hydrazine were added and stirred at 55° C. for 4 hrs. Subsequent concentration, dissolution in methanol, filtering of impurities and concentration gave 3-(4-methylpiperazino)-anilino-5-amino-1,2,4-triazole Compound 9A (87% yield). ¹H NMR (400 MHz, (CD₃)₂SO) δ 9.05 (s,1H), 8.60 (s, 1H), 7.35 (d, 2H), 6.77 (d, 2H), 5.70 (s, 2H), 2.97 (m, 4H), 2.48 (m, 4H), 2.23 (s, 3H); MS (ESI) m/z: 274 (M+H⁺). 3-(4-methylpiperazino)-anilino-5-amino-1,2,4-triazole Compound 9A was acylated with 2,6-difluoro benzoyl chloride Compound 1F in anhydrous pyridine to produce compound 71 (30% yield). ¹H NMR (300 MHz, (CD₃)₂SO) δ 9.07 (s, 1H), 7.88 (s, 1H), 7.72–7.66 (m, 1H), 7.32 (t, 1H), 7.25–7.17 (m, 2H), 6.97–6.92 (m, 1H), 6.71 (d, 1H), 3.39–3.35 (m, 2H), 3.17 (s, 3H), 3.00–2.97 (m, 4H), 2.51–2.46 (m, 4H); MS (ESI) m/z: 414 (M+H⁺).

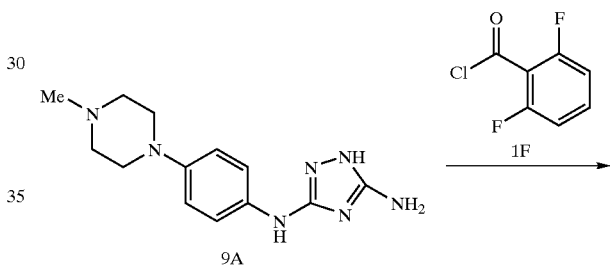

9A

| Cpd | Name/Data | Starting Mat'l |
|-----|-----------|----------------|
| 64 | 1-benzoyl-N³-(3-chlorophenyl)-1H-1,2,4-triazole-3,5-diamine<br>¹H NMR (300 MHz, (CD₃)₂CO) δ 8.58 (s, 1H), 8.30 (m, 2H), 8.00 (m, 1H), 7.75–7.25 (m, 6H), 6.90 (d, 1H); MS (ESI) m/z: 314 (M + H⁺), 336 (M + Na⁺) | benzoyl chloride in anhydrous pyridine |
| 126 | N⁵-(3-chlorophenyl)-1-(2,6-difluorobenzoyl)-1H-1,2,4-triazole-3,5-diamine<br>(minor regioisomer of Cpd 63) ¹H NMR (300 MHz, CDCl₃) δ 9.90 (s, 1H), 7.90 (s, 1H), 7.58–6.95 (m, 7H), 4.35 (s, 2H); MS (ESI) m/z: 350 (M + H⁺), 472 (M + Na⁺) | |
| 127 | 1-benzoyl-N⁵-(3-chlorophenyl)-1H-1,2,4-triazole-3,5-diamine<br>(minor regioisomer of Cpd 64) ¹H NMR (300 MHz, (CD₃)₂CO) δ 10.30 (s, 1H), 8.20 (d, 2H), 8.15 (m, 1H), 7.70–7.60 (m, 2H), 7.55 (t, 2H), 7.35 (t, 1H), 7.10 (d, 1H), 5.60 (s, 2H); MS (ESI) m/z: 314 (M + H⁺), 336 (M + Na⁺) | |

-continued

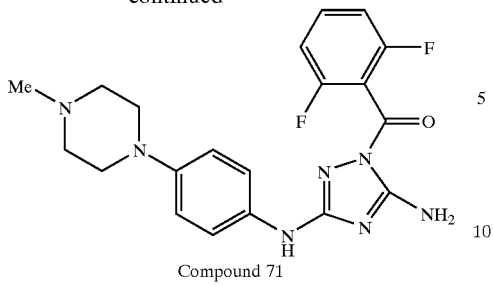

Compound 71

Using the procedure for Example 9, the following compounds were prepared by acylation of the intermediate Compound 9A using the indicated starting material in place of Compound 1F and reagent(s):

| Cpd | Name/Data | Starting Mat'l |
|---|---|---|
| 72 | 1-(2,6-difluoro-3-methylbenzoyl)-$N^3$-[4-(4-methyl-1-piperazinyl)phenyl]-1H-1,2,4-triazole-3,5-diamine<br>$^1$H NMR (300 MHz, $(CD_3)_2SO$) δ 9.05(s, 1H), 7.87 (s, 1H), 7.59–7.51 (m, 1H), 7.24–7.18 (m, 2H), 6.72 (d, 2H), 3.35 (s, 2H), 2.99–2.96 (m, 4H), 2.45–2.42 (m, 4H), 2.28 (s, 3H); MS (ESI) m/z: 428 (M + H$^+$) | 2,6-difluoro-3-methyl benzoyl chloride in anhydrous pyridine |
| 73 | $N^3$-[4-(4-methyl-1-piperazinyl)phenyl]-1-[(3-methyl-2-thienyl)carbonyl]-1H-1,2,4-triazole-3,5-diamine<br>$^1$H NMR (300 MHz, $(CD_3)_2SO$) δ 9.13 (s, 1H), 7.77 (s, 1H), 7.58–7.55 (m, 2H), 7.38–7.26 (m, 1H), 6.92 (d, 2H), 3.17 (s, 3H), 3.09–3.07 (m, 4H), 2.62 (s, 4H), 2.35 (s, 3H); MS (ESI) m/z: 398 (M + H$^+$) | 3-methyl-2-thiophene carboxylic acid, mediated by DIC/HOBt in anhydrous DMF |
| 74 | 1-[(3,5-dimethyl-2-thienyl)carbonyl]-$N^3$-[4-(4-methyl-1-piperazinyl)phenyl]-1H-1,2,4-triazole-3,5-diamine<br>$^1$H NMR (300 MHz, $(CD_3)_2SO$) δ 9.11 (s, 1H), 7.73 (s, 2H), 7.59–7.54 (m, 2H), 7.38–7.26 (m, 1H), 6.94 (d, 2H), 3.16–3.13 (m, 4H), 2.80–2.78 (m, 4H), 2.56 (s, 3H), 2.53 (s, 3H), 2.46 (s, 3H); MS (ESI) m/z: 412 (M + H$^+$) | 3,5-dimethyl-2-thiophene carboxylic acid, mediated by DIC/HOBt in anhydrous DMF |
| 75 | 1-[(5-ethyl-2-thienyl)carbonyl]-$N^3$-[4-(4-methyl-1-piperazinyl)phenyl]-1H-1,2,4-triazole-3,5-diamine<br>$^1$H NMR (300 MHz, $(CD_3)_2SO$) δ 9.17 (s, 1H), 7.78 (s, 1H), 7.51 (d, 2H), 7.35–7.24 (m, 3H), 7.08 (d, 2H), 3.14–3.12 (m, 4H), 2.96 (q, 2H), 2.76–2.73 (m, 4H), 2.43 (s, 3H), 1.34 (t, 3H); MS (ESI) m/z: 412 (M + H$^+$) | 5-ethyl-2-thiophene carboxylic acid, mediated by DIC/HOBt in anhydrous DMF |

EXAMPLE 10

4-[[5-amino-1-(2,6-difluorobenzoyl)-1H-1,2,4-triazol-3-yl]amino]-N-ethyl-benzenesulfonamide (Cpd 76)

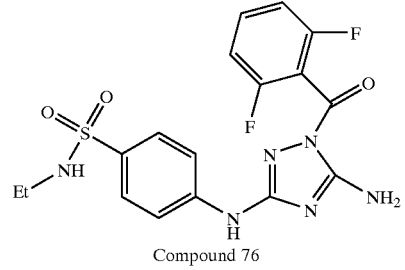

Compound 1 (100 mg, 0.254 mmol) was reacted with 1.2 equivalents of ethyl trifluoromethanesulfonate (Et-TFMS) (40 μL, 0.305 mmol), and 1.5 equivalents of potassium t-butoxide (K-t-BO) (0.38 mmol, 381 μL of a 1.0 M THF solution) in THF (5 mL) at 50° C., stirring for 16 hours. Purification of the reaction mixture by column chromatography in 10% methanol/methylene chloride gave the product Compound 76 (27.1 mg, 25% yield). $^1$H NMR (400 MHz, $(CD_3)_2SO$) δ 9.87 (s,1H), 8.00 (s, 2H), 7.76–7.68 (m, 1H), 7.55–7.48 (m, 4H), 7.34 (t, 2l1), 7.22 (t, 1H), 2.73–2.67 (m, 2H) 0.94 (t, 3H); MS (ESI) m/z: 423 (M+H$^+$).

EXAMPLE 12

$N^3$-methyl-1-[(3-methyl-2-thienyl)carbonyl]-1H-1,2,4-triazole-3,5-diamine (Cpd 79)

Using the procedure of Example 1,3,5-diamino-1,2,4-triazole Compound 12A was acylated with 3-methylthiophene-2-carboxylic acid Compound 12B mediated by DIC/HOBt in anhydrous DMF to produce Compound 41 (72% yield). $^1$H NMR (300 MHz, $(CD_3)_2SO$) δ 7.88 (d, J=4.5, 1H), 7.59 (s, 2H), 7.05 (d, J=4.8, 1H), 5.78 (s, 2H), 2.55 (s, 3H); MS (ESI) m/z: 224.1 (M+H$^+$), 245.9 (M+Na$^+$). Compound 41 (0.45 mmol, 100 mg) was reacted with 3 equivalents of iodomethane (1.34 mmol, 84 uL) and 1.1 equivalents of potassium t-butoxide (0.49 mmol, 493 uL of 1.0 M THF solution) in THF (5 mL), stirring 16 hours at 25° C. Purification by column chromatography (eluting with 10% methanol/dichloromethane) gave the product Compound 79 (7.7 mg, 7% yield). $^1$H NMR (400 MHz, $(CD_3)_2SO$) δ 9.80 (s, 1H), 7.60 (d,1H), 6.96 (d, 1H), 6.17 (s, 2H), 3.47 (s, 3H), 2.40 (s, 3H); MS (ESI) m/z: 238 (M+H$^+$), 260 (M+Na$^+$).

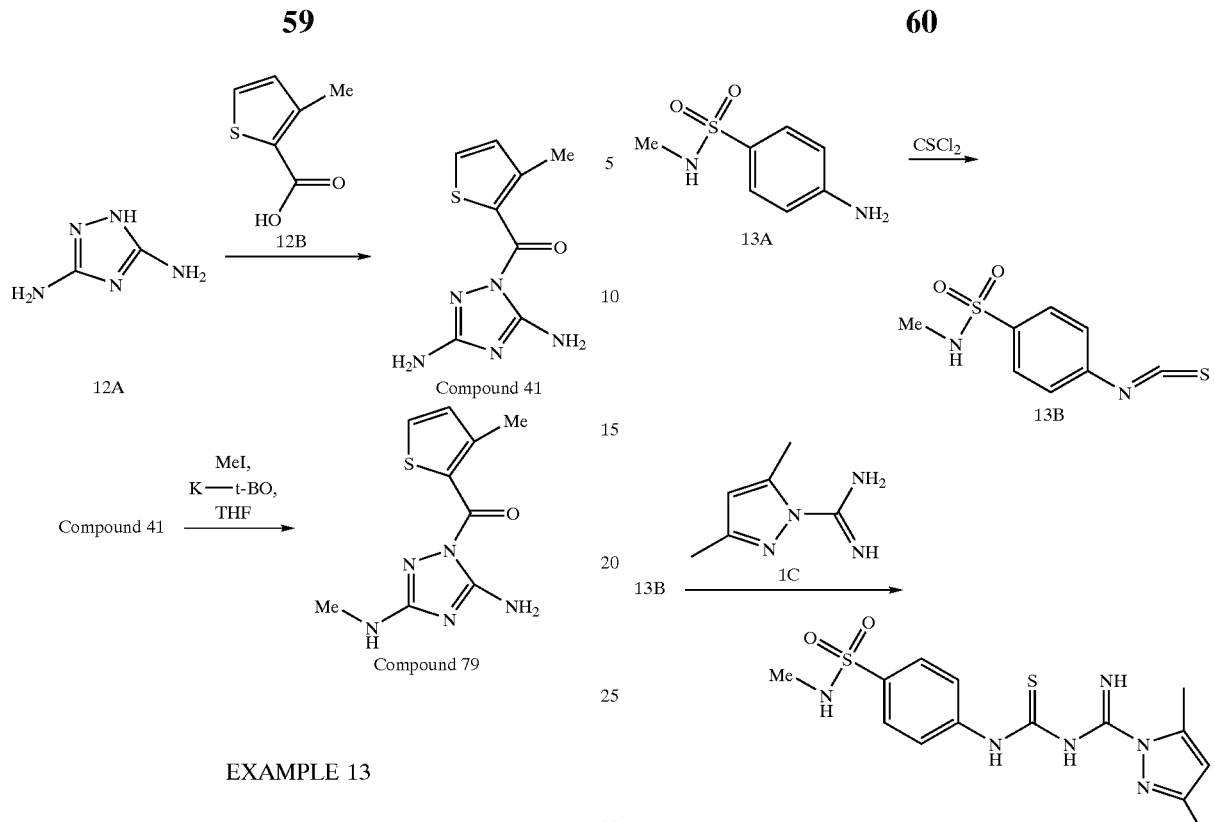

EXAMPLE 13

4-[[5-amino-1-(2,6-difluorobenzoyl)-1H-1,2,4-triazol-3-yl]amino]-N-methyl-benzenesulfonamide (Cpd 80)

t-BuOK (23.1 mL, 1.0 M solution in t-BuOH, 23.1 mmol) was added dropwise to a solution of 4-isothiocyanato-N-methylbenzenesulfonamide Compound 13B (prepared using the procedure of Example 1) (4.8 g, 21.0 mmol) and 2,5-dimethylpyrazole-1-carboximidine nitrate Compound 1C (4.2 g, 21.0 mmol) in DMF (20 mL). The mixture was heated to 60° C. for 2 h, then poured into ice. The precipitate was collected by filtration and washed with water, then air dried to afford 4-[3-(3,5-dimethylpyrazol-1-yliminomethyl)thioureido]-N-methylbenzenesulfonamide Compound 13C as a yellow solid (7.3 g, 95% yield). $^1$H NMR (300 MHz, (CD$_3$)$_2$SO) δ 8.01 (s, 1H), 7.71 (m, 4H), 6.15 (s, 1H), 2.40 (s, 3H), 2.22 (s, 6H); MS (ESI) m/z: 367 (M+H$^+$). Hydrazine (3.3 g, 110.0 mmol) at 0° C. was added to a suspension of 4-[3-(3,5-dimethylpyrazol-1-yliminomethyl)thioureido]-N-methylbenzenesulfonamide Compound 13C (2.0 g, 5.5 mmol) in THF (20 mL). The mixture was heated to 60° C. for 2 hrs, then poured into ice. The precipitate was collected by filtration, washed with water and CH$_2$Cl$_2$, then air dried to produce Compound 13D as a white solid (1.3 g, 87% yield). $^1$H NMR (300 MHz, (CD$_3$)$_2$SO) δ 11.36 (s, 1H), 9.31 (s, 1H), 7.63 (q, 4H), 7.09 (q, 1H), 6.05 (s, 2H), 2.39 (d,3H); MS (ESI) m/z: 269 (M+H$^+$). Using the procedure of Example 1, Compound 13D was acylated with 2,6-difluorobenzoyl chloride Compound 1F in anhydrous pyridine to produce Compound 80 (80% yield). $^1$H NMR (300 MHz, CD$_3$OD) δ 7.64 (m, 1H), 7.63 (d, 2H), 7.53 (d, 2H), 7.15 (t, 2H), 2.43 (s, 3H); MS (ESI) m/z: 409 (M+H$^+$).

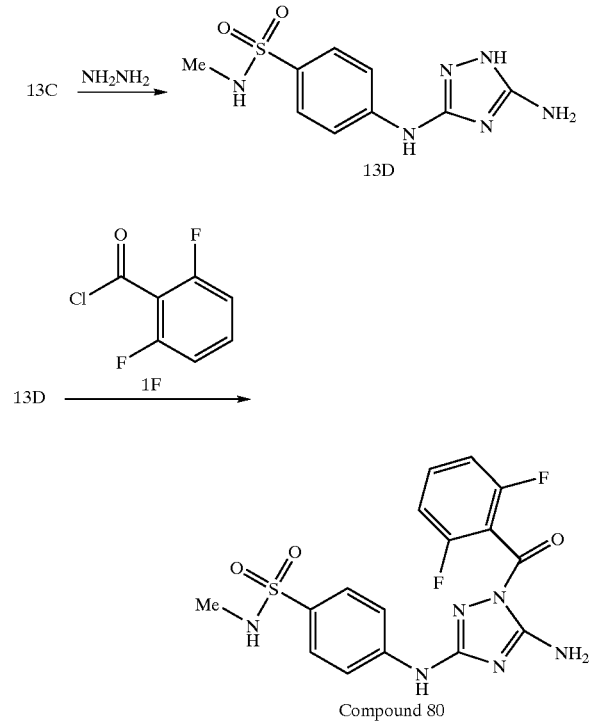

Using the procedure for Example 13, the following compounds were prepared by acylation of the intermediate Compound 13D using the indicated starting material in place of Compound 1F and reagent(s):

| Cpd | Name/Data | Starting Mat'l |
|---|---|---|
| 81 | 4-[[5-amino-1-(2,6-difluoro-3-methylbenzoyl)-1H-1,2,4-triazol-3-yl]amino]-N-methyl-benzenesulfonamide<br>$^1$H NMR (300 MHz, CD$_3$OD) δ 7.55 (d, 2H), 7.48–7.44 (m, 1H), 7.46 (d, 2H), 2.42 (s, 3H), 2.25 (s, 3H); MS (ESI) m/z: 423 (M + H$^+$) | 2,6-difluoro-3-methylbenzoyl chloride in anhydrous pyridine |
| 82 | 4-[[5-amino-1-[(3-methyl-2-thienyl)carbonyl]-1H-1,2,4-triazol-3-yl]amino]-N-methyl-benzenesulfonamide<br>$^1$H NMR (300 MHz, (CD$_3$)$_2$SO) δ 9.92 (s, 1H), 8.03 (d, 1H), 7.81 (d, 2H), 7.69 (d, 2H), 7.14 (m, 2H), 2.62 (s, 3H), 2.55 (s, 3H); MS (ESI) m/z: 393 (M + H$^+$) | 3-methylthiophene-2-carboxylic acid mediated by DIC/HOBt in DMF |
| 83 | 4-[[5-amino-1-[(3,5-dimethyl-2-thienyl)carbonyl]-1H-1,2,4-triazol-3-yl]amino]-N-methyl-benzenesulfonamide<br>$^1$H NMR (300 MHz, (CD$_3$)$_2$SO) δ 9.89 (s, 1H), 8.09 (d, 1H), 7.74 (d, 2H), 7.63 (d, 2H), 7.02 (d, 1H), 2.94 (q, 2H), 2.32 (s, 3H), 1.33 (t, 3H); MS (ESI) m/z: 407 (M + H$^+$) | 3,5-dimethylthiophene-2-carboxylic acid mediated by DIC/HOBt in DMF |
| 84 | 4-[[5-amino-1-[(5-ethyl-2-thienyl)carbonyl]-1H-1,2,4-triazol-3-yl]amino]-N-methyl-benzenesulfonamide<br>$^1$H NMR (300 MHz, (CD$_3$)$_2$SO) δ 9.65 (s, 1H), 7.64 (d, 1H), 7.50 (d, 2H), 7.69 (d, 2H), 6.66 (s, 1H), 2.36 (s, 3H), 2.34 (s, 3H), 2.12 (s, 3H); MS (ESI) m/z: 407 (M + H$^+$) | 5-ethylthiophene-2-carboxylic acid mediated by DIC/HOBt in DMF |

EXAMPLE 14

1-[(3,5-dimethyl-2-thienyl)carbonyl]-N$^3$-[4-(1H-imidazol-1-yl)phenyl]-1H-1,2,4-triazole-3,5-diamine (Cpd 85)

4-Isothiocyanato-N,N-dimethylbenzenesulfonamide Compound 14B (prepared using the procedure of Example 1) (1.8 g, 7.4 mmol) was reacted with 2,5-dimethylpyrazole-1-carboximidine nitrate Compound 1C (1.5 g, 7.4 mmol) and t-BuOK (7.4 mL, 1.0 M solu in t-BuOH, 7.4 mmol) to produce 4-[3-(3,5-dimethylpyrazol-1-yliminomethyl)thioureido]-N,N-dimethylbenzenesulfonamide Compound 14C as a yellow solid (2.5 g, 89% yield). $^1$H NMR (300 MHz, (CD$_3$)$_2$SO) δ 10.05 (s, 1H), 8.91 (s, 1H), 7.67 (m, 4H), 6.15 (s, 1H), 2.57 (s, 6H), 2.18 (s, 6H); MS (ESI) m/z: 381 (M+H$^+$). Compound 14C (2.5 g, 6.6 mmol) was reacted with hydrazine (4.2 g, 132.0 mmol) to produce 1.7 g (90%) of Compound 14D as a white solid. $^1$H NMR (300 MHz, (CD$_3$)$_2$SO) δ 9.47 (s, 1H), 7.81 (d, 2H), 7.75 (d, 2H), 6.10 (s 1H), 2.67 (s, 6H); MS (ESI) m/z: 283 (M+H$^+$). Compound 14D was acylated with 3,5-dimethylthiophene-2-carboxylic acid Compound 1F mediated by DIC/HOBt in DMF to produce Compound 85 (52% yield). $^1$H NMR (300 MHz, (CD$_3$)$_2$SO) δ 9.93 (s, 1H), 7.88 (d, 2H), 7.85 (s, 1H), 7.65 (d, 2H), 6.90 (s, 1H), 2.60 (s, 6H), 2.56 (s, 3H), 2.54 (s, 3H); MS (ESI) m/z: 421 (M+H$^+$).

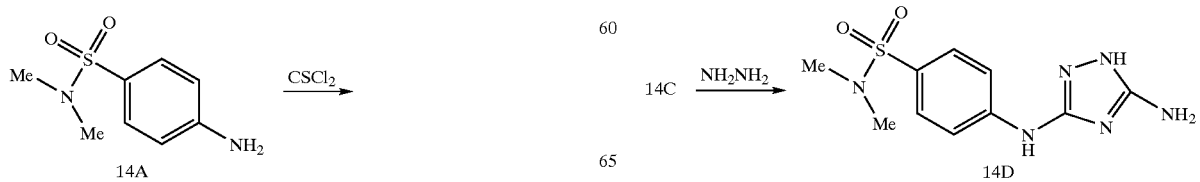

-continued

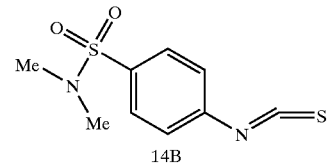

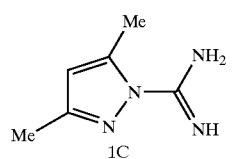

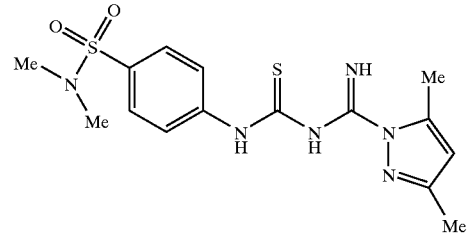

EXAMPLE 15

1-[(5-ethyl-2-thienyl)carbonyl]-$N^3$-[4-(1H-imidazol-1-yl)phenyl]-1H-1,2,4-triazole-3,5-diamine (Cpd 90)

Using the published procedure (Webb et al., *J. Heterocyclic Chem.*, 1987, 24, 275–278), 4-imidazol-1-yl-aniline (0.50 g, 3.14 mmol), diphenyl cyanocarbonimidate (0.75 g, 3.14 mmol) and THF (30 mL) were combined in a nitrogen purged flask. The mixture was refluxed for 2 hrs, then cooled down to ice temperature and hydrazine (31.4 mL, 1.0 M solution in THF, 31.4 mmol) was added dropwise. The mixture was then refluxed for 2 hrs. The precipitate was filtered and collected, washed with ethyl acetate and air dried to produce the intermediate Compound 15A (0.60 g, 79%). $^1$H NMR (300 MHz, (CD$_3$)$_2$SO) δ 11.15 (s, 1H), 8.85 (s, 1H), 8.05 (s, 1H), 7.57 (s, 1H), 7.48 (d, 2H), 7.35 (d, 2H), 7.04 (s, 1H), 5.85 (s, 2H); MS (ESI) m/z: 242 (M+H$^+$). Using the procedure of Example 1, Compound 15A was acylated with 5-ethylthiophene-2-carboxylic acid Compound 15B mediated by DIC/HOBt in DMF to provide Compound 90 (59% yield). $^1$H NMR (300 MHz, (CD$_3$)$_2$SO) δ 9.63 (s, 1H), 8.14 (d, 1H), 7.85–7.70 (m, 7H), 7.56–7.53 (m, 2H), 7.07 (d, 2H), 2.95 (q, 2H), 1.33 (t, 3H); MS (ESI) m/z: 380 (M+H$^+$).

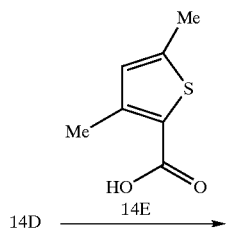

14D

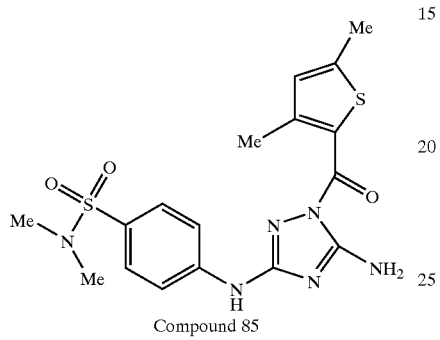

Compound 85

Using the procedure for Example 14, the following compounds were prepared by acylation of the intermediate Compound 14D using the indicated starting material in place of Compound 14E and reagent(s):

| Cpd | Name/Data | Starting Mat'l |
|---|---|---|
| 86 | 4-[[5-amino-1-[(5-ethyl-2-thienyl)carbonyl]-1H-1,2,4-triazol-3-yl]amino]-N,N-dimethyl-benzenesulfonamide $^1$H NMR (300 MHz, (CD$_3$)$_2$SO) δ 10.03 (s, 1H), 8.13 (d, 1H), 7.91 (s, 1H), 7.86 (d, 2H), 7.66 (d, 2H), 7.10 (d, 2H), 2.95 (q, 2H), 2.56 (s, 6H), 1.32 (t, 3H); MS (ESI) m/z: 421 (M + H$^+$) | 5-ethylthiophene-2-carboxylic acid mediated by DIC/HOBt in DMF |
| 87 | 4-[[5-amino-1-[(3-methyl-2-thienyl)carbonyl]-1H-1,2,4-triazol-3-yl]amino]-N,N-dimethyl-benzenesulfonamide $^1$H NMR (300 MHz, (CD$_3$)$_2$SO) δ 10.01 (s, 1H), 8.05 (d, 1H), 7.86 (d, 3H), 7.69 (d, 2H), 7.13 (d, 1H), 2.63 (s, 3H), 2.55 (s, 6H); MS (ESI) m/z: 407 (M + H$^+$) | 3-methylthiophene-2-carboxylic acid mediated by DIC/HOBt in DMF |
| 88 | 4-[[5-amino-1-(2,6-difluoro-3-methylbenzoyl)-1H-1,2,4-triazol-3-yl]amino]-N,N-dimethyl-benzenesulfonamide $^1$H NMR (300 MHz, CDCl$_3$) δ 7.79 (s, 1H), 7.55 (d, 2H), 7.40 (d, 2H), 7.35 (m, 1H), 6.95 (s, 2H), 6.92 (m, 1H), 2.65 (s, 6H), 2.27 (s, 3H); MS (ESI) m/z: 437 (M + H$^+$) | 2,6-difluoro-3-methylbenzoyl chloride in anhydrous pyridine |
| 89 | 4-[[5-amino-1-(2,6-difluorobenzoyl)-1H-1,2,4-triazol-3-yl]amino]-N,N-dimethyl-benzenesulfonamide $^1$H NMR (300 MHz, (CD$_3$)$_2$SO) δ 9.74 (s, 1H), 7.77 (s, 2H), 7.50–7.40 (m, 1H), 7.30–7.20 (m, 4H), 7.10 (m, 2H), 2.25 (s, 6H); MS (ESI) m/z: 423 (M + H$^+$) | 2,6-difluorobenzoyl chloride in anhydrous pyridine |

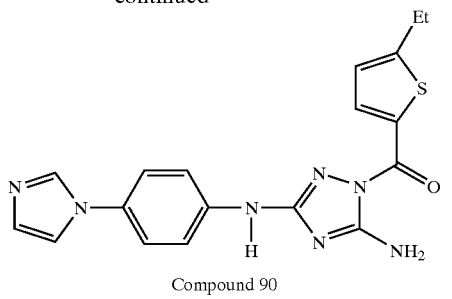

Compound 90

Using the procedure for Example 15, the following compounds were prepared by acylation of the intermediate Compound 15A using the indicated starting material in place of Compound 15B and reagent(s):

MHz, $(CD_3)_2SO$) δ 9.62 (s, 1H), 9.11 (s, 1H), 8.12 (s, 1H), 7.91 (s, 1H), 7.56 (d, 2H), 7.60–7.50 (q, 1H), 7.45 (d, 2H), 7.16 (t, 1H), 2.25 (s, 3H); MS (ESI) m/z: 397 (M+H$^+$).

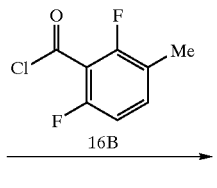

16A + 16B →

| Cpd | Name/Data | Starting Mat'l |
|---|---|---|
| 91 | N$^3$-[4-(1H-imidazol-1-yl)phenyl]-1-[(3-methyl-2-thienyl)carbonyl]-1H-1,2,4-triazole-3,5-diamine<br>$^1$H NMR (300 MHz, (CD$_3$)$_2$SO) δ 9.62 (s, 1H), 7.97 (d, 1H), 7.92 (s, 1H), 7.82–7.72 (m, 5H), 7.56–7.53 (m, 2H), 7.11 (d, 1H), 2.61 (s, 3H); MS (ESI) m/z: 366 (M + H$^+$) | 3-methylthiophene-2-carboxylic acid mediated by DIC/HOBt in DMF |
| 92 | 1-[(3,5-dimethyl-2-thienyl)carbonyl]-N$^3$-[4-(1H-imidazol-1-yl)phenyl]-1H-1,2,4-triazole-3,5-diamine<br>$^1$H NMR (300 MHz, (CD$_3$)$_2$SO) δ 9.51 (s, 1H), 8.15 (s, 1H), 7.75 (m, 4H), 7.61 (s, 1H), 7.53 (d, 2H), 7.05 (s, 1H), 6.85 (s, 1H), 2.53 (s, 3H), 2.52 (s, 3H); MS (ESI) m/z: 380 (M + H$^+$) | 3,5-dimethylthiophene-2-carboxylic acid mediated by DIC/HOBt in DMF |
| 93 | 1-(2,6-difluorobenzoyl)-N$^3$-[4-(1H-imidazol-1-yl)phenyl]-1H-1,2,4-triazole-3,5-diamine<br>$^1$H NMR (300 MHz, (CD$_3$)$_2$SO) δ 9.52 (s, 1H), 8.06 (s, 1H), 7.93 (s, 1H), 7.70 (p, 1H), 7.57 (s, 1H), 7.45 (d, 2H), 7.36 (d, 2H), 7.30 (t, 2H), 7.01 (s, 1H); MS (ESI) m/z: 382 (M + H$^+$) | 2,6-difluorobenzoyl chloride in anhydrous pyridine |
| 94 | 1-(2,6-difluoro-3-methylbenzoyl)-N$^3$-[4-(1H-imidazol-1-yl)phenyl]-1H-1,2,4-triazole-3,5-diamine<br>$^1$H NMR (300 MHz, (CD$_3$)$_2$SO) δ 9.52 (s, 1H), 8.08 (s, 1H), 7.93 (s, 1H), 7.57 (s, 1H), 7.53 (m, 1H), 7.42 (d, 2H), 7.35 (d, 2H), 7.18 (t, 1H), 7.02 (s, 1H), 2.25 (s, 3H); MS (ESI) m/z: 396 (M + H$^+$) | 2,6-difluoro-3-methylbenzoyl chloride in anhydrous pyridine |

EXAMPLE 16

1-(2,6-difluoro-3-methylbenzoyl)-N$^3$-[4-(1H-1,2,4-triazol-1-yl)phenyl]-1H-1,2,4-triazole-3,5-diamine (Cpd 95)

Using the procedure of Example 15, 4-(1,2,4-triazol-1-yl)-aniline (0.35 g, 2.18 mmol), diphenyl cyanocarbonimidate (0.52 g, 2.18 mmol) and hydrazine (21.8 mL, 1.0 M solution in THF, 21.8 mmol) were reacted to produce Compound 16D (0.40 g, 78% yield) as a white solid. $^1$H NMR (300 MHz, (CD$_3$)$_2$SO) δ 11.21 (s, 1H), 9.06 (s, 1H), 8.92 (s, 1H), 8.13 (s, 1H), 7.61 (m 4H), 5.87 (s, 2H); MS (ESI) m/z: 243 (M+H$^+$). Using the procedure of Example 1, Compound 16D was acylated with 2,6-difluoro-3-methylbenzoyl chloride Compound 16B in anhydrous pyridine to produce Compound 95 (51% yield). $^1$H NMR (300

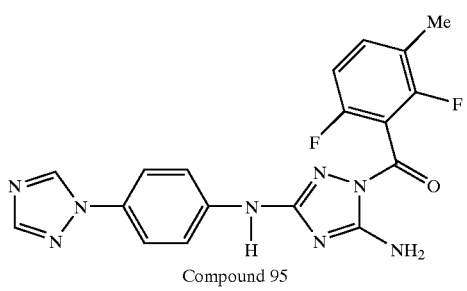

Compound 95

Using the procedure for Example 16, the following compounds were prepared by acylation of the intermediate Compound 16A using the indicated starting material in place of Compound 16B and reagent(s):

| Cpd | Name/Data | Starting Mat'l |
|---|---|---|
| 96 | 1-(2,6-difluorobenzoyl)-$N^3$-[4-(1H-1,2,4-triazol-1-yl)phenyl]-1H-1,2,4-triazole-3,5-diamine<br>$^1$H NMR (300 MHz, $(CD_3)_2SO$) δ 9.61 (s, 1H), 9.05 (s, 1H), 8.07 (s, 1H), 7.85 (s, 2H), 7.63 (p, 1H), 7.53 (d, 2H), 7.41 (d, 2H), 7.30 (t, 2H), 7.29 (t, 2H); MS (ESI) m/z: 383 (M + H$^+$) | 2,6-difluorobenzoyl chloride in anhydrous pyridine |
| 97 | 1-[(5-ethyl-2-thienyl)carbonyl]-$N^3$-[4-(1H-1,2,4-triazol-1-yl)phenyl]-1H-1,2,4-triazole-3,5-diamine<br>$^1$H NMR (300 MHz, $(CD_3)_2SO$) δ 9.72 (s, 1H), 9.15 (s, 1H), 8.17 (s, 1H), 8.16 (d, 1H), 7.78 (s, 2H), 7.77 (d, 2H), 7.72 (d, 2H), 7.04 (d, 1H), 2.96 (q, 2H), 1.33 (t, 3H); MS (ESI) m/z: 381 (M + H$^+$) | 5-ethylthiophene-2-carboxylic acid mediated by DIC/HOBt in DMF |
| 98 | 1-[(3,5-dimethyl-2-thienyl)carbonyl]-$N^3$-[4-(1H-1,2,4-triazol-1-yl)phenyl]-1H-1,2,4-triazole-3,5-diamine<br>$^1$H NMR (300 MHz, $(CD_3)_2SO$) δ 9.67 (s, 1H), 9.15 (s, 1H), 8.18 (s, 1H), 7.75 (m, 6H), 6.89 (s, 1H), 2.52 (s, 3H), 2.51 (s, 3H); MS (ESI) m/z: 381 (M + H$^+$) | 3,5-dimethylthiophene-2-carboxylic acid mediated by DIC/HOBt in DMF |
| 99 | 1-[(3-methyl-2-thienyl)carbonyl]-$N^3$-[4-(1H-1,2,4-triazol-1-yl)phenyl]-1H-1,2,4-triazole-3,5-diamine<br>$^1$H NMR (300 MHz, $(CD_3)_2SO$) δ 9.68 (s, 1H), 9.13 (s, 1H), 8.16 (s, 1H), 7.99 (d, 1H), 7.77 (m, 6H), 7.12 (d, 1H); MS (ESI) m/z: 367 (M + H$^+$) | 3-methylthiophene-2-carboxylic acid mediated by DIC/HOBt in DMF |

EXAMPLE 17

1-(2,6-difluorobenzoyl)-$N^3$-[4-(4H-1,2,4-triazol-4-yl)phenyl]-1H-1,2,4-triazole-3,5-diamine (Cpd 100)

Using the procedure of Example 15, 4-(1,3,4-triazol-1-yl)-aniline (1.35 g, 8.43 mmol), diphenyl cyanocarbonimidate (2.00 g, 8.43 mmol) and hydrazine (84.3 mL, 1.0 M solution in THF, 84.3 mmol) were reacted to provide Compound 17A (1.10 g, 77% yield) as a white solid. $^1$H NMR (300 MHz, $(CD_3)_2SO$) δ 8.90 (s, 2H), 7.62 (d, 2H), 7.36 (d, 2H), 5.82 (s, 2H); MS (ESI) m/z: 243 (M+H$^+$). Using the procedure of Example 1, Compound 17A was acylated with 2,6-difluorobenzoyl chloride Compound 1F in anhydrous pyridine to provide Compound 100 (36% yield). $^1$H NMR (300 MHz, $(CD_3)_2SO$) δ 9.61 (s, 1H), 8.98 (s, 2H), 7.96 (s, 2H), 7.67 (p, 1H), 7.47 (d, 2H), 7.42 (d, 2H), 7.32 (t, 2H); MS (ESI) m/z: 383 (M+H$^+$).

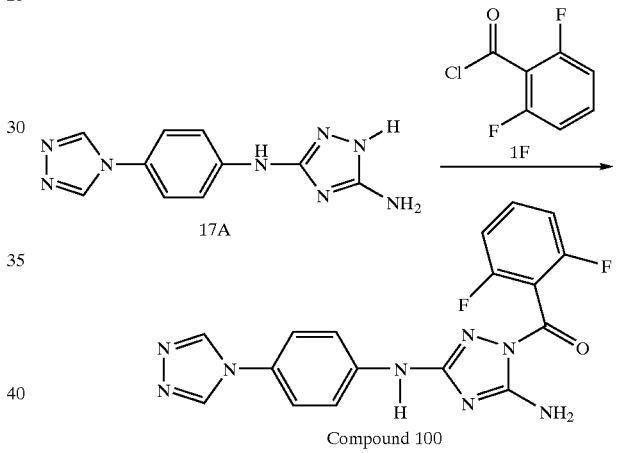

Compound 100

Using the procedure for Example 17, the following compounds were prepared by acylation of the intermediate Compound 17D using the indicated starting material in place of Compound 1F and reagent(s):

| Cpd | Name/Data | Starting Mat'l |
|---|---|---|
| 101 | 1-(2,6-difluoro-3-methylbenzoyl)-$N^3$-[4-(4H-1,2,4-triazol-4-yl)phenyl]-1H-1,2,4-triazole-3,5-diamine<br>$^1$H NMR (300 MHz, $(CD_3)_2SO$) δ 9.61 (s, 1H), 8.94 (s, 2H), 7.91 (s, 2H), 7.55 (q, 1H), 7.43 (q, 4H), 7.18 (t, 1H); MS (ESI) m/z: 397 (M + H$^+$) | 2,6-difluoro-3-methylbenzoyl chloride in anhydrous pyridine |
| 102 | 1-[(3-methyl-2-thienyl)carbonyl]-$N^3$-[4-(4H-1,2,4-triazol-4-yl)phenyl]-1H-1,2,4-triazole-3,5-diamine<br>$^1$H NMR (300 MHz, $(CD_3)_2SO$) δ 10.22 (s, 1H), 9.04 (s, 2H), 7.95 (m, 3H), 7.67 (d, 2H), 7.07 (d, 1H), 6.13 (s, 2H); MS (ESI) m/z: 367 (M + H$^+$) | 3-methylthiophene-2-carboxylic acid mediated by DIC/HOBt in DMF |

EXAMPLE 18

4-[[5-amino-1-[(5-ethyl-2-thienyl)carbonyl]-1H-1,2,4-triazol-3-yl]amino]-N-[2-(dimethylamino)ethyl]-benzenesulfonamide (Cpd 103)

Using the procedure of Example 15, 4-amino-N-(2-dimethylaminoethyl)-benzenesulfonamide (2.00 g, 8.22 mmol), diphenyl cyanocarbonimidate (2.00 g, 8.22 mmol) and hydrazine (82.3 mL, 1.0 M solution in THF, 82.3 mmol) were reacted to produce Compound 18A (1.35 g, 50% yield) as a white solid. $^1$H NMR (300 MHz, (CD$_3$)$_2$SO) δ 9.22 (s, 1H), 8.43 (s, 1H), 7.55 (m, 4H), 7.02 (s, 1H), 5.91 (s, 2H), 2.71 (t, 2H), 2.15 (t, 2H), 2.05 (s, 6H); MS (ESI) m/z: 326 (M+H$^+$). Using the procedure of Example 1, Compound 18A was acylated with 5-ethylthiophene-2-carboxylic acid Compound 15B mediated by DIC/HOBt in DMF to produce

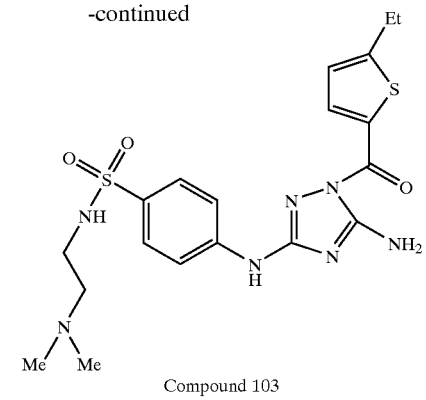

Compound 103

Using the procedure for Example 18, the following compounds were prepared by acylation of the intermediate Compound 18A using the indicated starting material in place of Compound 15B and reagent(s):

| Cpd | Name/Data | Starting Mat'l |
|---|---|---|
| 104 | 4-[[5-amino-1-[(3-methyl-2-thienyl)carbonyl]-1H-1,2,4-triazol-3-yl]amino]-N-[2-(dimethylamino)ethyl]-benzenesulfonamide $^1$H NMR (300 MHz, (CD$_3$)$_2$SO) δ 9.89 (s, 1H), 8.04 (d, 1H), 7.83 (s, 1H), 7.79 (d, 2H), 7.71 (d, 2H), 7.15 (s, 2H), 7.08 (d, 1H), 2.76 (t, 2H), 2.61 (s, 3H), 2.21 (t, 2H), 2.07 (s, 6H); MS (ESI) m/z: 450 (M + H$^+$) | 3-methylthiophene-2-carboxylic acid mediated by DIC/HOBt in DMF |
| 105 | 4-[[5-amino-1-(2,6-difluoro-3-methylbenzoyl)-1H-1,2,4-triazol-3-yl]amino]-N-[2-(dimethylamino)ethyl]-benzenesulfonamide $^1$H NMR (300 MHz, CD$_3$OD) δ 7.57 (d, 2H), 7.45 (m, 3H), 7.00 (t, 1H), 2.86 (t, 2H), 2.32 (t, 2H), 2.25 (s, 3H), 2.11 (s, 6H); MS (ESI) m/z: 480 (M + H$^+$) | 2,6-difluoro-3-methylbenzoyl chloride in anhydrous pyridine |
| 106 | 4-[[5-amino-1-(2,6-difluorobenzoyl)-1H-1,2,4-triazol-3-yl]amino]-N-[2-(dimethylamino)ethyl]-benzenesulfonamide $^1$H NMR (300 MHz, CD$_3$OD) δ 7.60 (m, 1H), 7.55 (d, 2H), 7.45 (d, 2H), 7.11 (t, 1H), 2.87 (t, 2H), 2.32 (t, 2H), 2.12 (s, 6H); MS (ESI) m/z: 466 (M + H$^+$) | 2,6-difluorobenzoyl chloride in anhydrous pyridine |
| 107 | 4-[[5-amino-1-[(3,5-dimethyl-2-thienyl)carbonyl]-1H-1,2,4-triazol-3-yl]amino]-N-[2-(dimethylamino)ethyl]-benzenesulfonamide $^1$H NMR (300 MHz, (CD$_3$)$_2$SO) δ 9.89 (s, 1H), 7.81 (m, 4H), 7.71 (d, 2H), 7.22 (s, 1H), 6.86 (s, 1H), 2.79 (t, 2H), 2.63 (s, 3H), 2.61 (s, 3H), 2.21 (t, 6H), 2.06 (s, 6H); MS (ESI) m/z: 464 (M + H$^+$) | 3,5-dimethylthiophene-2-carboxylic acid mediated by DIC/HOBt in DMF |

Compound 103 (40% yield). $^1$H NMR (300 MHz, (CD$_3$)$_2$SO) δ 10.02 (s, 1H), 8.13 (d, 1H), 7.88 (s, 1H), 1H), 7.75 (d, 2H), 7.71 (d, 2H), 7.07 (d, 1H), 7.01 (s, 2H), 2.95 (q, 2H), 2.75 (t, 2H), 2.20 (t, 2H), 2.04 (s, 6H), 1.35 (t, 3H); MS (ESI) m/z: 464 (M+H$^+$).

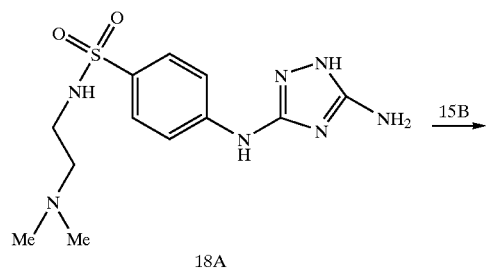

18A

EXAMPLE 19

N-[4-[[5-amino-1-[(3,5-dimethyl-2-thienyl)carbonyl]-1H-1,2,4-triazol-3–5 yl]amino]phenyl]-methanesulfonamide (Cpd 108)

Using the procedure of Example 15, N-(4-aminophenyl)methanesulfonamide (2.00 g, 10.70 mmol), diphenyl cyanocarbonimidate (2.60 g, 10.70 mmol), and hydrazine (107.0 mL, 1.0 M solution in THF, 107.0 mmol) were reacted to produce Compound 19A (1.30 g, 45% yield) as a white solid. $^1$H NMR (300 MHz, (CD$_3$)$_2$SO) δ 8.80 (s, 1H), 8.55 (s, 1H), 7.43 (d, 2H), 6.96 (d, 2H), 5.75 (s, 2H), 2.82 (s, 3H); MS (ESI) m/z: 269 (M+H$^+$). Using the procedure of Example 1, Compound 19A was acylated with 3,5-dimethylthiophene-2-carboxylic acid Compound 19B mediated by DIC/HOBt in DMF to provide Compound 108 (11% yield). $^1$H NMR (300 MHz, (CD$_3$)$_2$SO) δ 9.30 (s, 1H), 9.25 (s, 1H), 7.70 (s, 1H), 7.61 (d, 2H), 7.12 (d, 2H), 6.83 (s, 1H), 2.87 (s, 3H), 2.50 (s, 3H); MS (ESI) m/z: 407 (M+H$^+$).

EXAMPLE 20

1-[4-[[5-amino-1-[(3-methyl-2-thienyl)carbonyl]-1H-1,2,4-triazol-3-yl]amino]phenyl]-2-imidazolidinone (Cpd 113)

Using the procedure of Example 15, 1-(4-aminophenyl)imidazolidin-2-one (0.24 g, 1.35 mmol), diphenyl cyanocarbonimidate (0.32 g, 1.35 mmol) and hydrazine (13.5 mL, 1.0 M solution in THF, 13.5 mmol) were reacted to produce Compound 20A (0.28 g, 80%) as a white solid. $^1$H NMR (300 MHz, (CD$_3$)$_2$SO) δ 11.05 (s, 1H), 8.42 (s, 1H), 7.35 (d, 2H), 7.24 (d, 2H), 6.65 (s, 1H), 5.78 (s, 2H), 3.74 (t, 2H), 3.32 (t, 2H); MS (ESI) m/z: 260 (M+H$^+$). Using the procedure of Example 1, Compound 20A was acylated with 3-methylthiophene-2-carboxylic acid Compound 20B mediated by DIC/HOBt in DMF to provide Compound 113 (41% yield). $^1$H NMR (300 MHz, (CD$_3$)$_2$SO) δ 9.21 (s, 1H), 8.01 (d, 1H), 7.68 (s, 1H), 7.55 (d, 2H), 7.43 (d, 2H), 7.11 (d, 1H), 6.71 (s, 1H), 3.83 (q, 2H), 3.37 (q, 2H), 2.63 (s, 3H); MS (ESI) m/z: 384 (M+H$^+$).

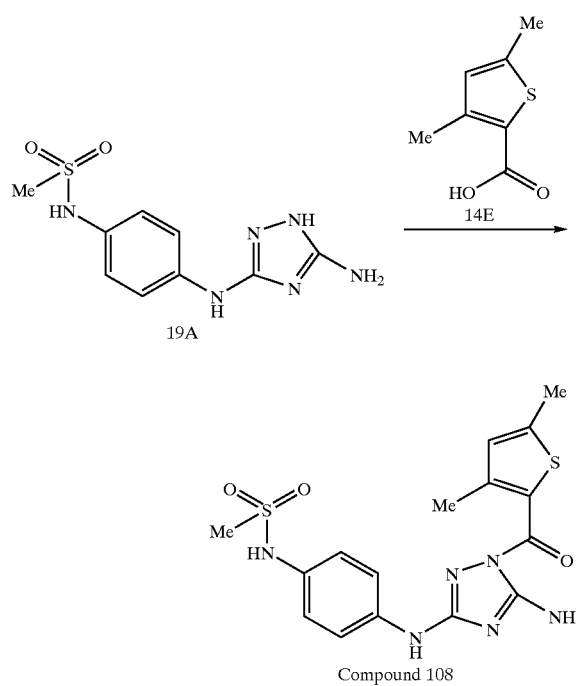

Compound 108

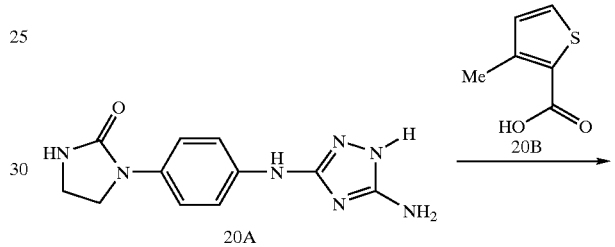

Using the procedure for Example 19, the following compounds were prepared by acylation of the intermediate Compound 19A using the indicated starting material in place of Compound 14E and reagent(s):

| Cpd | Name/Data | Starting Mat'l |
|---|---|---|
| 109 | N-[4-[[5-amino-1-[(3-methyl-2-thienyl)carbonyl]-1H-1,2,4-triazol-3-yl]amino]phenyl]-methanesulfonamide<br>$^1$H NMR (300 MHz, (CD$_3$)$_2$SO) δ 9.35 (s, 1H), 9.30 (s, 1H), 8.01 (d, 1H), 7.75 (s, 1H), 7.62 (d, 2H), 7.12 (m, 3H), 6.83 (s, 1H), 2.89 (s, 3H), 2.59 (s, 3H); MS (ESI) m/z: 393 (M + H$^+$) | 3-methylthiophene-2-carboxylic acid mediated by DIC/HOBt in DMF |
| 110 | N-[4-[[5-amino-1-[(5-ethyl-2-thienyl)carbonyl]-1H-1,2,4-triazol-3-yl]amino]phenyl]-methanesulfonamide<br>$^1$H NMR (300 MHz, (CD$_3$)$_2$SO) δ 9.37 (s, 1H), 9.30 (s, 1H), 8.12 (d, 1H), 7.74 (s, 1H), 7.62(d, 2H), 7.12 (d, 2H), 7.03 (d, 1H), 2.95 (q, 2H), 2.89 (s, 3H), 1.35 (t, 3H); MS (ESI) m/z: 407 (M + H$^+$) | 5-ethylthiophene-2-carboxylic acid mediated by DIC/HOBt in DMF |
| 111 | N-[4-[[5-amino-1-(2,6-difluorobenzoyl)-1H-1,2,4-triazol-3-yl]amino]phenyl]-methanesulfonamide<br>$^1$H NMR (300 MHz, (CD$_3$)$_2$SO) δ 9.32 (s, 1H), 9.21 (s, 1H), 7.88 (s, 2H), 7.64 (p, 1H), 7.25 (m, 4H), 6.92 (d, 2H), 2.82 (s, 3H); MS (ESI) m/z: 409 (M + H$^+$) | 2,6-difluorobenzoyl chloride in anhydrous pyridine |
| 112 | N-[4-[[5-amino-1-(2,6-difluoro-3-methylbenzoyl)-1H-1,2,4-triazol-3-yl]amino]phenyl]-methanesulfonamide<br>$^1$H NMR (300 MHz, (CD$_3$)$_2$SO) δ 9.33 (s, 1H), 7.88 (s, 2H), 7.54 (q, 1H), 7.25 (d, 2H), 7.16 (t, 1H), 6.92 (d, 2H), 2.82 (s, 3H), 2.25 (s, 3H); MS (ESI) m/z: 423 (M + H$^+$) | 2,6-difluoro-3-methylbenzoyl chloride in anhydrous pyridine |

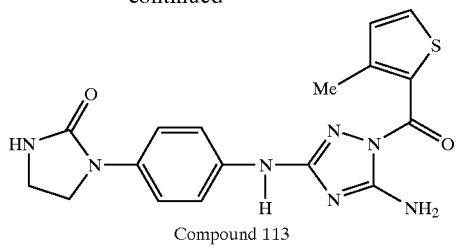

Compound 113

Using the procedure for Example 20, the following compounds were prepared by acylation of the intermediate Compound 20A using the indicated starting material in place of Compound 20B and reagent(s):

| Cpd | Name/Data | Starting Mat'l |
|---|---|---|
| 114 | 1-[4-[[5-amino-1-(2,6-difluoro-3-methylbenzoyl)-1H-1,2,4-triazol-3-yl]amino]phenyl]-2-imidazolidinone <br> $^1$H NMR (300 MHz, $(CD_3)_2SO$) δ 9.12 (s, 1H), 7.82 (s, 2H), 7.50 (m, 1H), 7.21 (m, 4H), 7.20 (m, 1H), 6.70 (s, 1H), 3.72 (t, 2H), 3.28 (t, 3H), 2.21 (s, 3H); MS (ESI) m/z: 414 (M + H$^+$) | 2,6-difluoro-3-methylbenzoyl chloride in anhydrous pyridine |
| 115 | 1-[4-[[5-amino-1-(2,6-difluorobenzoyl)-1H-1,2,4-triazol-3-yl]amino]phenyl]-2-imidazolidinone <br> $^1$H NMR (300 MHz, $(CD_3)_2SO$) δ 9.16 (s, 1H), 7.87 (s, 2H), 7.63 (m, 1H), 7.19 (m, 6H), 6.74 (s, 1H), 3.72 (t, 2H), 3.28 (t, 3H); MS (ESI) m/z: 400 (M + H$^+$) | 2,6-difluorobenzoyl chloride in anhydrous pyridine |

EXAMPLE 21

$N^3$-[4-(1,1-dioxido-2-isothiazolidinyl)phenyl]-1-[(3-methyl-2-thienyl)carbonyl]-1H-1,2,4-triazole-3,5-diamine (Cpd 116)

Using the procedure of Example 15, 4-(1,1-dioxoisothiazolidin-2-yl)phenylamine (0.92 g, 4.36 mmol), diphenyl cyanocarbonimidate (1.10 g, 4.36 mmol) and hydrazine (43.6 mL, 1.0 M solution in THF, 43.6 mmol) were reacted to produce Compound 21A (1.2 g, 95%) as a white solid. $^1$H NMR (300 MHz, $(CD_3)_2SO$) δ 11.05 (s, 1H), 8.58 (s, 1H), 7.47 (d, 2H), 7.05 (d, 2H), 5.78 (s, 1H), 3.55 (t, 2H), 3.32 (t, 2H), 2.30 (p, 2H); MS (ESI) m/z: 295 (M+H$^+$). Using the procedure of Example 1, Compound 21A was acylated with 3-methylthiophene-2-carboxylic acid Compound 20B mediated by DIC/HOBt in DMF to produce Compound 116 (48% yield). $^1$H NMR (300 MHz, $(CD_3)_2$SO) δ 9.38 (s, 1H), 8.01 (d, 1H), 7.73 (s, 2H), 7.62 (d, 2H), 7.15 (d, 2H), 7.08 (d, 1H), 3.67 (t, 2H), 3.42 (t, 2H), 2.58 (s, 3H), 2.35 (p, 2H); MS (ESI) m/z: 419 (M+H$^+$).

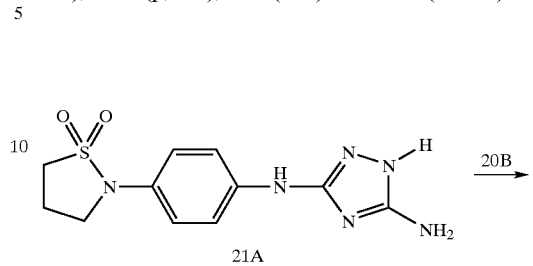

21A

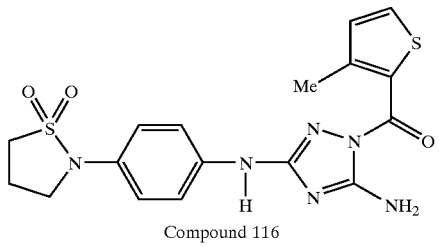

Compound 116

Using the procedure for Example 21, the following compounds were prepared by acylation of the intermediate Compound 21A using the indicated starting material in place of Compound 20B and reagent(s):

| Cpd | Name/Data | Starting Mat'l |
|---|---|---|
| 117 | 1-(2,6-difluorobenzoyl)-$N^3$-[4-(1,1-dioxido-2-isothiazolidinyl)phenyl]-1H-1,2,4-triazole-3,5-diamine <br> $^1$H NMR (300 MHz, $(CD_3)_2SO$) δ 9.31 (s, 1H), 7.80 (s, 2H), 7.62 (t, 2H), 7.28 (m, 3H), 7.01 (d, 2H), 3.63 (t, 2H), 3.35 (t, 2H), 2.32 (p, 2H); MS (ESI) m/z: 435 (M + H$^+$) | 2,6-difluorobenzoyl chloride in anhydrous pyridine |

EXAMPLE 22

4-[[5-amino-1-(2,6-difluorobenzoyl)-1H-1,2,4-triazol-3-yl]amino]-N-(2-pyridinyl)-benzenesulfonamide (Cpd 118)

Using the procedure of Example 15, 4-amino-N-pyridin-2-yl-benzenesulfonamide (1.48 g, 5.96 mmol), diphenyl cyanocarbonimidate (1.42 g, 5.96 mmol), and hydrazine (59.6 mL, 1.0 M solution in THF, 59.6 mmol) were reacted to provide Compound 22A (0.98 g, 50%) as a white solid. $^1$H NMR (300 MHz, (CD$_3$)$_2$SO) δ 9.22 (s, 1H), 8.05 (s, 1H), 7.73 (m, 3H), 7.53 (d, 2H), 7.04 (d, 1H), 6.85 (m, 2H), 5.85 (s, 2H); MS (ESI) m/z: 332 (M+H$^+$). Using the procedure of Example 1, Compound 22A was acylated with 2,6-difluorobenzoyl chloride Compound 1F in anhydrous pyridine to provide Compound 118 (61% yield). $^1$H NMR (300 MHz, (CD$_3$)$_2$SO) δ 9.85 (s, 1H), 8.00–7.90 (m, 2H), 7.65 (m, 1H), 7.59 (d, 2H), 7.35 (d, 2H), 7.25 (t, 2H), 7.04 (d, 1H), 6.81 (t, 1H), 3.31 (s, 2H); MS (ESI) m/z: 472 (M+H$^+$).

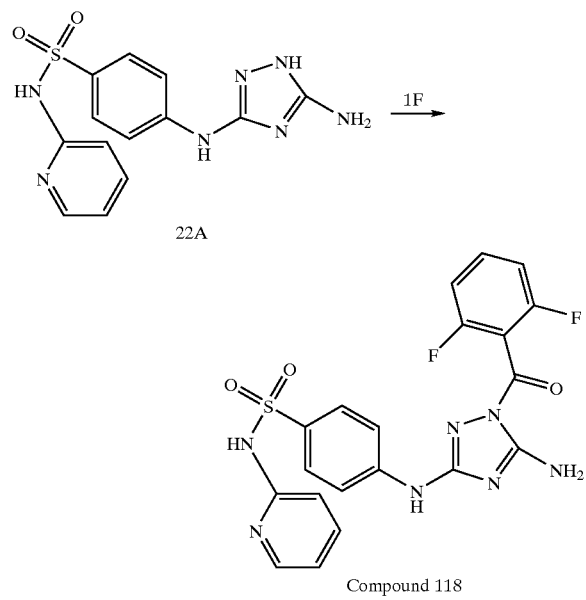

Using the procedure for Example 22, the following compounds were prepared by acylation of the intermediate Compound 22A using the indicated starting material in place of Compound 1F and reagent(s):

| Cpd | Name/Data | Starting Mat'l |
|---|---|---|
| 119 | 4-[[5-amino-1-[(5-ethyl-2-thienyl)carbonyl]-1H-1,2,4-triazol-3-yl]amino]-N-(2-pyridinyl)-benzenesulfonamide<br>$^1$H NMR (300 MHz, (CD$_3$)$_2$SO) δ 9.87 (s, 1H), 8.11 (d, 1H), 8.01 (s, 1H), 7.90 (s, 1H), 7.75 (m, 4H), 7.68 (d, 2H), 7.63 (t, 1H), 7.07 (m, 2H), 6.85 (m, 1H), 2.95 (q, 2H), 1.32 (t, 3H); MS (ESI) m/z: 470 (M+H$^+$) | 5-ethylthiophene-2-carboxylic acid mediated by DIC/HOBt in DMF |
| 120 | 4-[[5-amino-1-[(3,5-dimethyl-2-thienyl)carbonyl]-1H-1,2,4-triazol-3-yl]amino]-N-(2-pyridinyl)-benzenesulfonamide<br>$^1$H NMR (300 MHz, (CD$_3$)$_2$SO) δ 9.84 (s, 1H), 7.98 (s, 1H), 7.91 (s, 1H), 7.74 (m, 4H), 7.71 (d, 2H), 7.63 (t, 1H), 7.07 (m 1H), 6.85 (m, 2H), 2.53 (s, 3H), 2.52 (s, 3H); MS (ESI) m/z: 470 (M+H$^+$) | 3,5-dithylthiophene-2-carboxylic acid mediated by DIC/HOBt in DMF |
| 121 | 4-[[5-amino-1-[(3-methyl-2-thienyl)carbonyl]-1H-1,2,4-triazol-3-yl]amino]-N-(2-pyridinyl)-benzenesulfonamide<br>$^1$H NMR (300 MHz, (CD$_3$)$_2$SO) δ 9.85 (s, 1H), 8.02 (m, 2H), 7.79 (m, 4H), 7.73 (d, 2H), 7.63 (t, 1H), 7.13 (d, 1H), 7.07 (m 1H), 6.81 (m, 1H), 2.61 (s, 3H); MS (ESI) m/z: 456 (M+H$^+$) | 3-methylthiophene-2-carboxylic acid mediated by DIC/HOBt in DMF |

BIOLOGICAL EXAMPLES

The utility of the compounds to treat or ameliorate a cyclin dependent kinase and tyrosine kinase mediated disorders was determined using the following procedures.

Eample 1
CDK1 Screening Assay

A kinase reaction mixture was prepared containing 50 mM Tris-HCl pH=8, 10 mM MgCl$_2$, 0.1 mM Na$_2$PO$_4$, 1 mM DTT, 10 μM ATP, 0.025 μM biotinylated histone-H1 peptide substrate and 0.2 μCuries per well $^{33P}$-γ-ATP [2000–3000 Ci/mmol]. 70 μL of the kinase reaction mixture was dispensed into the well of a streptavidin coated FlashPlate™ (Cat. # SMP103, NEN, Boston, Mass.). Then 1 μL of test compound stock in 100% DMSO was added to the wells resulting in a final concentration of 1% DMSO in the reaction with a 100 μl final reaction volume. Next, CDK1:Cyclin-B protein was diluted in 50 mM Tris-HCl pH=8.0, 0.1% BSA at a concentration of 1 ng per μL and 30 μl (30 ng enzyme per test well) was added to each well to initiate the reaction. The reaction was incubated for one hour at 30° C. At the end of the 1-hour incubation, the reaction was terminated by aspirating the reaction mixture from the plate and washing the wells twice with PBS containing 100 mM EDTA. The histone-H1 biotinylated peptide substrate became immobilized on the Flashplate™ and the incorporation of $^{33}$P-γ-ATP was measured by reading the plate on a scintillation counter. Inhibition of the enzymatic activity of CDK1 was measured by observing a reduced amount of $^{33}$P-γ-ATP incorporated into the immobilized peptide.

VEGF-R Screening Assay

A kinase reaction mixture was prepared containing 50 mM Tris-HCl pH=8, 10 mM MgCl$_2$, 0.1 mM Na$_3$PO$_4$, 1 mM DTT, 10 μM ATP, 0.025 μM biotinylated peptide substrate and 0.8 μCuries per well $^{33P}$-γ-ATP [2000–3000 Ci/mmol]. 70 μL of the kinase reaction mixture was dispensed into the well of a streptavidin coated FlashPlate™ (Cat. # SMP103, NEN, Boston, Mass.). Then 1 μL of test compound stock in 100% DMSO was added to the wells resulting in a final concentration of 1% DMSO in the reaction with a 100 μL final reaction volume. Next, soluble rat tyrosine kinase containing an N-terminal 6xHIS tag was diluted in 50 mM Tris-HCl pH=8.0, 0.1% BSA at a concentration of 5 ng per μL and 30 μL (150 ng enzyme per test well) was added to each well to initiate the reaction. The reaction was incubated for one hour at 30° C. At the end of the 1-hour incubation, the reaction was terminated by aspirating the reaction mixture from the plate and washing the wells twice with PBS containing 100 mM EDTA. The PLC1 biotinylated peptide substrate became immobilized on the Flashplate™ and the incorporation of $^{33}$P-γ-ATP was measured by reading the plate on a scintillation counter. Inhibition of the enzymatic activity of the VEGF-R was measured by observing a reduced amount of $^{33}$P-γ-ATP incorporated into the immobilized peptide.

IC$_{50}$ data for VEGF-R and CDK are shown in Table 1. IC$_{50}$ values listed as >10 or >100 indicate no observed 50% inhibition at the highest dose tested, nor was an inhibition maxima observed. ND means not tested.

TABLE 1

| Cpd | CDK1 | VEGF-R | HER2 | CDK2 |
|---|---|---|---|---|
| | | IC$_{50}$ (uM) | | |
| 1 | 0.0064 | 0.1062 | ND | ND |
| 2 | 0.0032 | 0.3659 | ND | ND |
| 3 | 0.0080 | 0.3324 | ND | ND |
| 4 | 0.02232 | 0.3866 | ND | ND |
| 5 | 0.1436 | 0.5209 | ND | ND |
| 6 | 0.0394 | 8.144 | ND | ND |
| 7 | 0.057 | >10 | ND | ND |
| 8 | 0.136 | >100 | ND | ND |
| 9 | 0.039 | 1.597 | ND | ND |
| 10 | 0.252 | 0.4907 | ND | ND |
| 11 | 0.3046 | >100 | ND | ND |
| 12 | 0.0454 | 0.08406 | ND | ND |
| 13 | 0.5353 | 0.5318 | ND | ND |
| 14 | 0.0045 | 0.0267 | ND | ND |
| 15 | 0.0048 | 0.0511 | ND | ND |
| 16 | 0.0021 | 0.0137 | ND | ND |
| 17 | 0.0025 | 0.027 | ND | ND |
| 18 | 0.067 | 0.058 | ND | ND |
| 19 | 0.0339 | 0.2907 | ND | ND |
| 20 | 0.0044 | 0.031 | ND | ND |
| 21 | 0.0088 | 0.023 | ND | ND |
| 22 | 0.0318 | 0.2334 | ND | ND |
| 23 | 0.0889 | 0.0353 | ND | ND |
| 24 | 0.2823 | 0.0674 | ND | ND |
| 25 | 0.01953 | 0.064 | ND | ND |
| 26 | 18.4 | ~100 | ND | ND |
| 27 | ~100 | >100 | ND | ND |
| 28 | 0.9816 | 13.25 | ND | ND |
| 29 | 70.39 | ~100 | ND | ND |
| 30 | 0.017 | 0.0406 | ND | ND |
| 31 | 0.030 | 0.044 | ND | ND |
| 32 | 0.0031 | 0.0219 | ND | ND |
| 33 | 0.0032 | 0.0234 | ND | ND |
| 34 | 0.0016 | 0.0681 | ND | ND |
| 35 | 0.0011 | 0.0463 | ND | ND |
| 36 | 1.561 | 18.61 | ND | ND |
| 37 | 10.5 | 54.98 | ND | ND |
| 38 | 0.0299 | 0.8795 | ND | ND |
| 39 | 0.0122 | 0.3336 | ND | ND |
| 40 | 0.1949 | 11.06 | ND | ND |
| 42 | 0.1342 | 0.4433 | ND | ND |
| 43 | 0.0873 | 0.6279 | ND | ND |
| 44 | 0.5223 | 2.677 | ND | ND |
| 45 | 0.0137 | 0.3553 | ND | ND |
| 46 | 0.0358 | 0.4527 | ND | ND |
| 47 | 0.0586 | 2.523 | ND | ND |
| 48 | 2.603 | ~100 | ND | ND |
| 49 | >1 | >1 | >1 | ND |
| 50 | 0.12 | 0.19 | 0.20 | ND |
| 51 | 0.007 | 0.019 | 0.031 | ND |
| 52 | 0.035 | 0.11 | 1.47 | ND |
| 53 | >1 | >1 | >1 | ND |
| 54 | 0.55 | 14.0 | 6.1 | ND |
| 55 | 0.022 | 0.58 | 2.19 | ND |
| 56 | 0.49 | 20.0 | 4.17 | ND |
| 57 | 0.067 | 0.19 | 1.32 | ND |
| 58 | 0.014 | 0.42 | 0.65 | ND |
| 59 | 1.54 | 0.92 | 7.83 | ND |
| 60 | 1.37 | 0.89 | 7.46 | ND |
| 66 | 0.0006 | 0.032 | 0.060 | 0.0005 |
| 67 | 0.0037 | 0.038 | 0.052 | 0.0014 |
| 68 | 0.66 | 5.14 | ND | ND |
| 69 | 0.023 | 0.69 | 0.14 | ND |
| 70 | 0.035 | 0.91 | 1.23 | ND |
| 71 | 3.71 | 0.43 | 1.30 | ND |
| 72 | 1.43 | 0.38 | 1.49 | ND |
| 73 | 2.20 | 0.029 | 0.176 | ND |
| 74 | 0.46 | 0.021 | 0.062 | ND |
| 75 | 0.52 | 0.033 | 0.060 | ND |
| 76 | 0.012 | 0.53 | ~1 | 0.0044 |
| 78 | 0.0066 | 0.42 | 0.78 | 0.0017 |
| 79 | >100 | >100 | >100 | >100 |
| 80 | 0.0452 | 0.9346 | 1.1200 | ND |
| 81 | 0.0178 | 0.4822 | 1.6990 | 0.001 |
| 82 | 0.0090 | 0.0217 | 0.1183 | ND |
| 83 | 0.0084 | 0.0404 | 0.0130 | ND |
| 84 | 0.0038 | 0.0432 | 0.0516 | ND |
| 85 | 0.4126 | 0.1943 | >1 | ND |
| 86 | 0.1087 | 0.0869 | 0.4128 | ND |
| 87 | 0.2171 | 0.0168 | 0.4357 | ND |
| 88 | 0.3134 | 0.9647 | ~1 | ND |
| 89 | 0.7096 | 0.5979 | ~10 | ND |
| 90 | ~1 | ~0.1 | ~0.1 | ND |
| 91 | 0.3349 | 0.0736 | 0.2233 | ND |
| 92 | 0.3493 | 0.1336 | 0.0558 | ND |
| 93 | 0.4525 | 0.7267 | ~1 | ND |
| 94 | 0.2716 | 0.4089 | 0.1469 | ND |
| 95 | 0.1387 | 0.2598 | 0.9138 | ND |
| 96 | 0.3726 | 0.8171 | 1.4080 | ND |
| 97 | ~0.1 | ~0.1 | ~0.01 | ND |
| 98 | >0.1 | ~0.1 | ~0.1 | ND |
| 99 | 0.3656 | 0.098 | 0.0945 | ND |
| 100 | 0.3404 | 1.1000 | 1.2870 | ND |
| 101 | 0.1426 | 0.6498 | 0.8195 | ND |
| 102 | 2.3530 | 1.1010 | 2.2600 | ND |
| 103 | 0.0074 | 0.0449 | 0.2284 | 0.001 |
| 104 | 0.0156 | 0.0156 | 0.2033 | 0.001 |
| 105 | 0.0461 | 0.2756 | 0.8448 | 0.002 |
| 106 | 0.1250 | 0.5591 | 37.230 | 0.001 |
| 107 | 0.0138 | 0.0324 | 0.0297 | 0.002 |
| 108 | 0.0657 | 0.0307 | 0.0417 | 0.0120 |
| 109 | 0.1465 | 0.0252 | 0.1705 | 0.0210 |
| 110 | 0.0219 | 0.0136 | 0.0055 | 0.0050 |
| 111 | 0.1499 | 0.7019 | 16.830 | ND |
| 112 | 0.0870 | 0.7039 | 16.350 | ND |
| 113 | 0.2545 | 0.0302 | 0.0680 | ND |
| 114 | 0.2275 | 0.3125 | 1.3870 | ND |
| 115 | 0.3134 | 0.4666 | 1.4420 | ND |
| 116 | 0.0208 | 0.0261 | 0.1313 | 0.0010 |
| 117 | 0.0352 | 0.9080 | 5.4350 | 0.0070 |
| 118 | 0.33 | 0.397 | >10 | 0.021 |
| 119 | 0.0672 | 0.0571 | ~1 | 0.0030 |
| 120 | 0.277 | 0.082 | 1.0 | 0.0090 |
| 121 | 0.0997 | 0.0272 | 0.7169 | 0.0030 |
| 122 | 2.21 | >10 | ND | ND |
| 123 | 2.05 | 5.53 | ~100 | 0.031 |
| 128 | 0.0032 | 0.118 | 0.111 | 0.0033 |

Example 2
Kinase Selectivity Assays

Assays to test compound inhibition of other kinases were preformed using methods that measure the amount of phosphorylation of a biotinylated peptide substrate. Biotinylated peptide substrates were selected from the literature as appropriate for the enzyme being evaluated. The general procedure used to assay for kinase activity is as follows: A kinase reaction mix was prepared in 50 mM Tris-HCl pH=8, 10 mM MgCl$_2$, 0.1 mM Na$_3$VO$_4$, 1 mM DTT, 10 $\mu$M ATP, 0.25–1 $\mu$M biotinylated peptide substrate, 0.2–0.82 $\mu$Curies per well $^{33}$P-$\gamma$-ATP [2000–3000 Ci/mmol]. Assay conditions vary slightly for each protein kinase, for example, insulin receptor kinase requires 10 mM MnCl$_2$ for activity and Calmodulin-dependent protein kinase requires calmodulin and 10 mM CaCl$_2$. These assay conditions are known in the art. The reaction mixture was dispensed into the wells of a streptavidin coated Flashplate and 1 $\mu$l drug stock in 100% DMSO was added to a 100 $\mu$l reaction volume resulting in a final concentration of 1% DMSO on the reaction. Enzyme was diluted in 50 mM Tris-HCl pH=8.0, 0.1% BSA and add to each well. The reaction was incubated for one hour at 30°

C. in the presence of compound. After one hour the reaction mix was aspirated from the plate and the plate was washed with PBS containing 100 mM EDTA. The plate was read on a scintillation counter to determine $^{33}$P-γ-ATP incorporated into the immobilized peptide. Test compounds were assayed in duplicate at 8 concentrations [100 uM, 10 uM, 1 uM, 100 nM, 10 nM, 1 nM, 100 pM, 10 pM]. A maximum and minimum signal for the assay was determined on each plate. The IC$_{50}$ was calculated from the dose response curve of the percent inhibition of the maximum signal in the assay according to the formula [max signal—background/test compound signal—background (100)=% inhibition] by graphing the percent inhibition against the log concentration of test compound. Known inhibitor compounds appropriate for the kinase being assayed were also included on each plate.

Definition and Source of Kinase Enzymes

VEGF-R (vascular endothelial growth factor receptor-2) is a fusion protein containing a polyhistidine tag at the N-terminus followed by amino acids 786–1343 of the rat VEGF-R2 kinase domain (GenBank Accession #U93306). CDK1 (cyclin dependent kinase 1) was isolated from insect cells expressing both the human CDK1 catalytic subunit and its positive regulatory subunit cyclin B (New England Biolabs, Beverly, Mass., Cat. # 6020). CDK2 in complex with cyclin A is commercially available (Upstate Biotech, Lake Placid, N.Y.). The CDK4 complex was composed of a mouse CDK4 protein and a mouse Cyclin D1 protein (The mouse CDK4 protein was genetically fused to an N-terminal Flag-epitope tag and the mouse Cyclin D1 protein was fused with an N-terminal AU-1 epitope tag. The genes encoding these proteins were transferred to commercially available baculoviral vectors. The recombinant CDK4/D1 complex was then made by co-infecting commercially available insect cells with viruses carrying these two constructs). Insulin Receptor Kinase consists of residues 941–1313 of the cytoplasmic domain of the beta-subunit of the human insulin receptor (BIOMOL, Plymouth Meeting, Pa., Cat. #SE-195). Protein Kinase A is the catalytic subunit of cAMP dependent protein kinase-A purified from bovine heart (Upstate Biotech, Lake Placid, N.Y., Cat#14–114). PKC (protein kinase-C) is the gamma or beta isoform of the human protein produced in insect cells (BIOMOL, Plymouth Meeting, Pa., Cat. #SE-143). Casein Kinase 1 is a truncation at amino acid 318 of the C-terminal portion of the rat CK1 delta isoform produced in E. coli (New England Biolabs, Beverly, Mass., Cat. #6030). Casein Kinase 2 includes the alpha and beta subunits of the human CK2 protein produced in E.coli (New England Biolabs, Beverly, Mass., Cat. #6010). Calmodulin Kinase (calmodulin-dependent protein kinase 2) is a truncated version of the alpha subunit of the rat protein produced in insect cells (New England Biolabs, Beverly, Mass., Cat. #6060). Glycogen Synthase Kinase-3 is the beta isoform of the rabbit enzyme produced in E. coli (New England Biolabs, Beverly, Mass., Cat. #6040). MAP Kinase is the rat ERK-2 isoform containing a polyhistidine tag at the N-terminus produced in E.coli. and activated by phosphorylation with MEK1 prior to purification (BIOMOL, Plymouth Meeting, Pa., Cat. #SE-137). ERK-1 protein (Discontinued from Calbiochem). EGFR (epidermal growth factor receptor) is purified from human A431 cell membranes (Sigma, St. Louis, Mo., Cat.# E3641). PDGF-R (platelet derived growth factor receptor) is a fusion protein containing a polyhistidine tag at the N-terminus followed by nucleotides 1874–3507 of the human PDGF-R beta subunit kinase domain (Accession #M21616). The HER2 (human epidermal growth factor receptor-2) construct contains a polyhistidine tag at the N-terminus followed by 24 additional amino acids and begins at amino acid 676 followed by the remainder of the HER2 cytoplasmic domain.

| Peptide Substrates | |
|---|---|
| VEGF-R | (Biotin)KHKKLAEGSAYEEV-Amide |
| CDK1 | (Biotin)KTPKKAKKPKTPKKAKKL-Amide |
| CDK2 | (Biotin)KTPKKAKKPKTPKKAKKL-Amide |
| CDK4 | (GST)AminoAcids 769–921 of retinoblastoma |
| EGF-R | (Biotin)Poly(GT)4:1 |
| Protein Kinase A | (Biotin)GRTGRRNSI-Amide |
| PKC | (Biotin)RFARKGSLRQKNV-NH2 |
| Casein Kinase 1 | (Biotin)KRRRALS(phospho)VASLPGL-Amide |
| Casein Kinase 2 | (Biotin)RREEETEEE-Amide |
| Calmodulin Kinase | Biotin)KKALRRQETVDAL-Amide |
| GSK-3 | Biotin)KRREILSRRP(phospho)SYR-Amide |
| MAP Kinase ERK-1 | (Biotin)APRTPGGRR-Amide |
| MAP Kinase ERK-2 | (Biotin)APRTPGGRR-Amide |
| Insulin Kinase | (Biotin)TRDIYETDYYRK-Amide |
| FGF-R2 | (Biotin)Poly(GT)4:1 |
| PDGF-R | (Biotin)KHKKLAEGSAYEEV-Amide |
| HER2 | (Biotin)KHKKLAEGSAYEEV-Amide |

The IC$_{50}$ data for various kinases are shown in Table 2a through Table 2k. IC$_{50}$ values listed as >10 or >100 indicate no observed 50% inhibition at the highest dose tested for the indicated assay, nor was an inhibition maxima observed. Values shown as ~10 indicate an approximate value based on an observed 50% inhibition. ND means not tested.

TABLE 2a

Kinase Selectivity

| Kinase Assay (IC$_{50}$ uM) | Cpd 1 | Cpd 2 | Cpd 14 | Cpd 15 | Cpd 16 |
|---|---|---|---|---|---|
| CDK1 | 0.006 | 0.003 | 0.0045 | 0.0048 | 0.021 |
| PKA | >100 | >100 | 5.43 | 4.26 | ND |
| Caseine Kinase 1 | 11.16 | >100 | 0.348 | 0.547 | 0.214 |
| Caseine Kinase 2 | >100 | >100 | 8.05 | >100 | >100 |
| PKC | ND | >100 | ND | ND | ND |
| ERK 1 | ND | ND | >100 | ND | ND |
| ERK 2 | 19.35 | 9.48 | 2.14 | 5.95 | 0.39 |
| Calmodulin Kinase 2 | >100 | >100 | 60.44 | 10.53 | >100 |
| EGF-R | >100 | 45.8 | 1.92 | 8.44 | >100 |
| VEGF-R | 0.131 | 0.366 | 0.026 | 0.051 | 0.0137 |
| Insulin R Kinase | >100 | 9.8 | 1.2 | 2.42 | >100 |
| GSK-3 | 0.041 | 0.031 | 0.003 | 0.0018 | 0.004 |
| PDGF-R kinase | 11.76 | 10.7 | 0.189 | 0.079 | 0.1 |
| FGF-R2 Kinase | ND | 0.269 | 0.027 | ND | ND |

TABLE 2b

Kinase Selectivity

| Kinase Assay (IC$_{50}$ uM) | Cpd 17 | Cpd 23 | Cpd 30 | Cpd 32 | Cpd 33 |
|---|---|---|---|---|---|
| CDK1 | 0.0025 | 0.089 | 0.017 | 0.003 | 0.003 |
| PKA | ND | >100 | ND | >100 | >100 |
| Caseine Kinase 1 | 0.643 | 0.113 | 1.54 | 0.181 | 0.104 |
| Caseine Kinase 2 | 2.65 | >100 | 7.6 | 0.527 | >10 |

TABLE 2b-continued

Kinase Selectivity

| Kinase Assay (IC$_{50}$ uM) | Cpd 17 | Cpd 23 | Cpd 30 | Cpd 32 | Cpd 33 |
|---|---|---|---|---|---|
| ERK 2 | 1.87 | 1.62 | 5.93 | 0.563 | >10 |
| Calmodulin Kinase 2 | 2.8 | 10.5 | 88.3 | >100 | >10 |
| EGF-R | 4.13 | >100 | 9.6 | >100 | >100 |
| VEGF-R | 0.027 | 0.035 | 0.0406 | 0.022 | 0.023 |
| Insulin R Kinase | 2.02 | >100 | 4.96 | 0.123 | 0.316 |
| GSK-3 | 0.009 | 0.016 | 0.014 | 0.003 | 0.004 |
| PDGF-R kinase | 0.081 | 0.629 | 0.392 | 0.074 | 0.039 |
| HER2 Kinase | ND | ND | ND | 0.009 | 0.005 |

TABLE 2c

Kinase Selectivity

| Kinase Assay (IC$_{50}$ uM) | Cpd 34 | Cpd 38 | Cpd 39 | Cpd 51 | Cpd 55 |
|---|---|---|---|---|---|
| CDK1 | 0.002 | 0.029 | 0.012 | 0.007 | 0.020 |
| PKA | >100 | >100 | >100 | 0.911 | >100 |
| Caseine Kinase 1 | 0.182 | 6.1 | 4.1 | 0.223 | 9.6 |
| Caseine Kinase 2 | >100 | >100 | >100 | 1.78 | >100 |
| ERK 2 | >10 | 24.2 | 13.2 | 0.928 | 12.9 |
| Calmodulin Kinase 2 | >100 | >100 | >100 | 0.813 | >100 |
| EGF-R | >100 | >100 | >100 | 1.1 | 16.12 |
| VEGF-R | 0.068 | 0.880 | 0.334 | 0.019 | 0.577 |
| Insulin R Kinase | >10 | >100 | 19.4 | 0.077 | >100 |
| GSK-3 | 0.015 | 0.122 | 0.127 | 0.020 | 0.040 |
| PDGF-R kinase | 0.292 | 6.37 | 3.98 | 0.199 | 16.18 |
| FGF-R2 Kinase | ND | ND | ND | ND | 0.478 |
| HER2 Kinase | ND | ND | ND | 0.031 | 2.19 |

TABLE 2d

Kinase Selectivity

| Kinase Assay (IC$_{50}$ uM) | Cpd 57 | Cpd 58 | Cpd 61 | Cpd 62 | Cpd 63 |
|---|---|---|---|---|---|
| CDK1 | 0.067 | 0.014 | 0.18 | 0.53 | 0.079 |
| CDK2 | ND | ND | 0.049 | 0.29 | 0.056 |
| PKA | >100 | >100 | ND | ND | ND |
| Caseine Kinase 1 | 14.0 | 11.24 | ND | ND | ND |
| Caseine Kinase 2 | >100 | >100 | ND | ND | ND |
| ERK 2 | >100 | 10.7 | ND | ND | ND |
| Calmodulin Kinase 2 | >100 | >100 | ND | ND | ND |
| EGF-R | >100 | >10 | ND | ND | ND |
| VEGF-R | 0.191 | 0.419 | 0.072 | 0.064 | 0.32 |
| Insulin R Kinase | >100 | >100 | ND | ND | ND |
| GSK-3 | 0.098 | 0.015 | 0.055 | 0.073 | 0.073 |
| PDGF-R kinase | 4.19 | 8.53 | ND | ND | ND |
| FGF-R2 Kinase | ND | 0.096 | ND | ND | ND |
| HER2 Kinase | 1.32 | 0.654 | 0.82 | 0.41 | 0.15 |

TABLE 2e

Kinase Selectivity

| Kinase Assay (IC$_{50}$ uM) | Cpd 64 | Cpd 65 | Cpd 66 | Cpd 69 | Cpd 70 |
|---|---|---|---|---|---|
| CDK1 | 0.21 | 0.67 | 0.0006 | 0.023 | 0.035 |
| CDK2 | 0.20 | 0.41 | ND | ND | ND |
| CDK4 | ND | ND | ND | 0.187 | 0.167 |
| PKA | ND | ND | 5.19 | 46.6 | 34.2 |
| Caseine Kinase 1 | ND | ND | 2.75 | 16.6 | 35.7 |
| Caseine Kinase 2 | ND | ND | >100 | >100 | >100 |
| ERK 2 | ND | ND | 1.0 | 12.5 | 19.4 |
| Calmodulin Kinase 2 | ND | ND | 8.99 | >100 | >100 |
| EGF-R | ND | ND | >10 | >100 | >100 |
| VEGF-R | 0.051 | 0.18 | 0.032 | 0.685 | 0.911 |
| Insulin R Kinase | ND | ND | >10 | 45.1 | >100 |
| GSK-3 | 0.021 | 0.10 | 0.137 | 0.147 | 0.22 |
| PDGF-R kinase | ND | ND | 1.58 | 0.1 | 16.2 |
| FGF-R2 Kinase | ND | ND | ND | 0.365 | 0.273 |
| HER2 Kinase | 0.076 | 0.79 | 0.060 | 0.139 | 1.23 |

TABLE 2f

Kinase Selectivity

| Kinase Assay (IC$_{50}$ uM) | Cpd 71 | Cpd 81 | Cpd 82 | Cpd 83 | Cpd 84 |
|---|---|---|---|---|---|
| CDK1 | 3.71 | 0.018 | 0.009 | 0.008 | 0.004 |
| CDK4 | 0.129 | ND | ND | ND | ND |
| PKA | >100 | >100 | >100 | >100 | 2.2 |
| Caseine Kinase 1 | >100 | 6.96 | 0.354 | 0.275 | 0.188 |
| Caseine Kinase 2 | >100 | >100 | >100 | >100 | 1.67 |
| ERK 2 | >100 | 11.68 | 1.95 | >100 | 1.22 |
| Calmodulin Kinase 2 | 60.9 | >100 | >100 | >100 | >100 |
| EGF-R | >10 | >100 | >100 | >100 | >10 |
| VEGF-R | 0.43 | 0.482 | 0.022 | 0.040 | 0.043 |
| Insulin R Kinase | 35.3 | 29.6 | 1.1 | >10 | 0.172 |
| GSK-3 | 1.72 | 0.049 | 0.025 | 0.007 | 0.019 |
| PDGF-R kinase | 27 | 7.76 | 0.042 | 0.113 | 0.280 |
| FGF-R2 Kinase | 0.441 | 0.268 | 0.089 | 0.022 | 0.300 |
| HER2 Kinase | 1.30 | 1.7 | 0.118 | 0.013 | 0.052 |

TABLE 2g

Kinase Selectivity

| Kinase Assay (IC$_{50}$ uM) | Cpd 92 | Cpd 99 | Cpd 103 | Cpd 104 |
|---|---|---|---|---|
| CDK1 | 0.349 | 0.366 | 0.007 | 0.0016 |
| PKA | >100 | ND | >100 | >100 |
| Caseine Kinase 1 | >10 | >1 | 0.322 | 0.624 |
| Caseine Kinase 2 | >100 | >100 | 5.3 | >100 |
| PKC | ND | >100 | ND | ND |
| ERK 2 | >100 | >100 | 0.845 | >100 |
| Calmodulin Kinase 2 | 19.7 | >100 | >100 | >10 |
| EGF-R | >100 | >100 | >10 | >10 |
| VEGF-R | 0.134 | 0.098 | 0.045 | 0.016 |
| Insulin R Kinase | 3.08 | >100 | 0.123 | 2.09 |

TABLE 2g-continued

Kinase Selectivity

| Kinase Assay (IC$_{50}$ uM) | Cpd 92 | Cpd 99 | Cpd 103 | Cpd 104 |
|---|---|---|---|---|
| GSK-3 | 0.021 | 0.030 | 0.013 | 0.020 |
| PDGF-R kinase | 0.282 | 0.385 | 0.702 | 0.192 |
| FGF-R2 Kinase | 0.242 | ND | 0.170 | 0.200 |
| HER2 Kinase | 0.056 | 0.095 | 0.228 | 0.202 |

TABLE 2h

Kinase Selectivity

| Kinase Assay (IC$_{50}$ uM) | Cpd 105 | Cpd 107 | Cpd 108 | Cpd 109 | Cpd 110 |
|---|---|---|---|---|---|
| CDK1 | 0.046 | 0.014 | 0.066 | 0.147 | 0.022 |
| PKA | >100 | >100 | >100 | >100 | >100 |
| Caseine Kinase 1 | 4.49 | 0.412 | 0.816 | 1.18 | 0.192 |
| Caseine Kinase 2 | >100 | >10 | >10 | >10 | >5 |
| ERK 2 | 18.19 | >10 | 2.39 | >10 | 8.75 |
| Calmodulin Kinase 2 | >100 | 3.43 | >10 | >100 | >100 |
| EGF-R | 9.60 | 0.936 | >100 | >100 | >10 |
| VEGF-R | 0.276 | 0.032 | 0.030 | 0.025 | 0.014 |
| Insulin R Kinase | 9.85 | 0.311 | 0.811 | 2.76 | 0.053 |
| GSK-3 | 0.082 | 0.015 | 0.023 | 0.039 | 0.008 |
| PDGF-R kinase | 2.20 | 0.143 | 0.217 | 0.413 | 0.285 |
| FGF-R2 Kinase | 0.142 | 0.235 | 0.307 | 0.244 | 0.153 |
| HER2 Kinase | 0.845 | 0.030 | 0.042 | 0.170 | 0.006 |

TABLE 2i

Kinase Selectivity

| Kinase Assay (IC$_{50}$ uM) | Cpd 113 | Cpd 114 | Cpd 115 | Cpd 116 | Cpd 117 |
|---|---|---|---|---|---|
| CDK1 | 0.254 | 0.228 | 0.313 | 0.021 | 0.035 |
| PKA | >100 | >100 | >100 | >100 | >100 |
| Caseine Kinase 1 | 0.318 | 2.0 | 9.98 | >1 | 13.46 |
| Caseine Kinase 2 | >100 | >100 | >100 | >100 | >100 |
| PKC | >100 | ND | ND | ND | ND |
| ERK 2 | >100 | 15.8 | >10 | >100 | >100 |
| Calmodulin Kinase 2 | >10 | >100 | >100 | >100 | >100 |
| EGF-R | >10 | >100 | >10 | >100 | >100 |
| VEGF-R | 0.030 | 0.313 | 0.467 | 0.026 | 0.908 |
| Insulin R Kinase | >10 | >100 | >10 | >100 | >100 |
| GSK-3 | 0.071 | 0.431 | 0.391 | 0.062 | 1.04 |
| PDGF-R kinase | 0.370 | 13.8 | >10 | 0.302 | >100 |
| HER2 Kinase | 0.068 | 1.39 | 1.44 | 0.131 | 5.44 |

TABLE 2j

Kinase Selectivity

| Kinase Assay (IC$_{50}$ uM) | Cpd 118 | Cpd 119 | Cpd 120 | Cpd 121 | Cpd 123 |
|---|---|---|---|---|---|
| CDK1 | 0.330 | 0.067 | 0.277 | 0.099 | 2.05 |
| PKA | >100 | >100 | >100 | >100 | >100 |
| Caseine Kinase 1 | >100 | 0.757 | >10 | >10 | >100 |
| Caseine Kinase 2 | >100 | >100 | >100 | >100 | >100 |
| PKC | ND | >100 | ND | ND | ND |
| ERK 2 | >100 | >100 | >100 | >100 | >100 |
| Calmodulin Kinase 2 | >100 | >100 | >100 | >100 | >100 |
| EGF-R | >100 | 0.159 | >10 | >10 | >100 |
| VEGF-R | 0.397 | 0.057 | 0.082 | 0.027 | 5.52 |
| Insulin R Kinase | >100 | 0.159 | >100 | >100 | >100 |
| GSK-3 | 0.159 | 0.006 | 0.018 | 0.029 | 3.01 |
| PDGF-R kinase | >100 | >10 | 0.822 | 0.394 | >100 |
| HER2 Kinase | >10 | 1.0 | 1.0 | 0.717 | >100 |

TABLE 2k

Kinase Selectivity

| Kinase Assay (IC$_{50}$ uM) | Cpd 124 | Cpd 125 | Cpd 126 | Cpd 127 | Cpd 128 |
|---|---|---|---|---|---|
| CDK1 | 2.2 | >100 | >100 | >100 | 0.003 |
| CDK2 | 1.7 | 7.3 | >100 | >100 | ND |
| PKA | ND | ND | ND | ND | >100 |
| Caseine Kinase 1 | ND | ND | ND | ND | 8.97 |
| Caseine Kinase 2 | ND | ND | ND | ND | >100 |
| ERK 2 | ND | ND | ND | ND | 2.07 |
| Calmodulin Kinase 2 | ND | ND | ND | ND | 13.2 |
| EGF-R | ND | ND | ND | ND | >100 |
| VEGF-R | 4.8 | >100 | >100 | >100 | 0.118 |
| Insulin R Kinase | ND | ND | ND | ND | 2.65 |
| GSK-3 | 3.0 | >100 | >100 | >100 | 0.094 |
| PDGF-R kinase | ND | ND | ND | ND | 1.91 |
| HER2 Kinase | 0.82 | >100 | ~100 | >100 | 0.11 |

Example 3
Assay to Measure Inhibition of Cell Proliferation

The ability of a test compound to inhibit the proliferation of cell growth was determined by measuring incorporation of $^{14}$C-labelled thymidine into newly synthesized DNA within the cells. This method was used on cell lines derived from carcinomas originating from several tissues such as HeLa cervical adenocarcinoma (American Type Culture Collection (ATCC), Virginia, Cat. #CCL-2), A375 malignant melanoma (ATCC CRL-1619), SK-OV-3 ovarian adenocarcinoma (ATCC HTB-77) HCT-116 colon carcinoma (CCL-247), PC-3 prostate adenocarcinoma (ATCC CRL-1435), and MDA-MB-231 (Xenogen Corp.) In this way the effect of a compound on cell growth of cells with many different phenotypes can be determined. Cells were trypsinized and counted and 3000–8000 cells were added to each well of a 96-well CytoStar tissue culture treated scintillating microplate (Amersham #RPNQ0160) in complete medium in a volume of 100 μl. Cells were incubated for 24 hours in complete medium at 37° C. in an atmosphere containing 5% $CO_2$. Next, 1 μl of test compound in 100% DMSO was added to the wells of the plate. DMSO only was added to control wells. Cells were incubated for 24 more hours in complete medium at 37° C. in an atmosphere containing 5% $CO_2$. Methyl $^{14}$C-thymidine 56 mCi/mmol (NEN #NEC568 or Amersham #CFA532) was diluted in complete medium and 0.2 uCi/well was added to each well of the CytoStar plate in a volume of 20 µl. The plate was incubated for 24 hours at 37° C. plus 5% $CO_2$ in drug plus $^{14}$C-thymidine. The contents of the plate were discarded into a $^{14}$C radioactive waste container by inverting the plate and the plate was washed twice with 200 µl PBS. 200 µl of PBS is added to each well. The top of the plate was sealed with a transparent plate sealer and a white plate backing sealer (Packard #6005199) was applied to the bottom of the plate. The degree of methyl $^{14}$C-thymidine incorporation was quantified on a Packard Top Count.

TABLE 3

Inhibition of Cell Proliferation ($IC_{50}$, nM)

| Cpd | HeLa | HCT-116 | SK-OV-3 | MDA-MB-231 | PC-3 | A375 |
|---|---|---|---|---|---|---|
| 1 | 284 | 254 | 750 | 587 | 119 | 447 |
| 14 | 550 | 1940 | 727 | 756 | 157 | 26460 |
| 15 | 91 | 127 | 242 | 550 | 107 | 247 |
| 16 | 263 | 213 | 2110 | ND | 368 | 942 |
| 17 | 215 | 309 | 3900 | ND | 294 | 4970 |
| 23 | 1180 | 376 | 1420 | 868 | 859 | 424 |
| 30 | 215 | 1930 | 5750 | ND | 951 | 8240 |
| 32 | 71 | 26 | ND | 131 | 30 | ND |
| 33 | 72 | 27 | ND | 171 | 37 | ND |
| 34 | 707 | 996 | ND | 898 | 626 | ND |
| 35 | 663 | 172 | ND | 1140 | 231 | ND |
| 38 | 4560 | 2270 | ND | 6760 | 2750 | ND |
| 39 | 270 | 1410 | ND | 2910 | 625 | ND |
| 51 | 220 | ND | ND | ND | 57 | 333 |
| 57 | 339 | 95 | ND | ND | ND | 113 |
| 58 | 186 | 1,270 | ND | ND | 362 | 981 |
| 66 | 35 | 20 | ND | ND | ND | 92 |
| 69 | 218 | 1,720 | ND | ND | 8 | 441 |
| 70 | 196 | 1,580 | ND | ND | 11 | 1,100 |
| 71 | 1,920 | ND | ND | ND | 25 | ND |
| 80 | 880 | ND | 16,300 | ND | 272 | ND |
| 81 | 189 | 778 | 348 | ND | 25 | 1,770 |
| 82 | 245 | ND | 921 | ND | 15 | ND |
| 83 | 122 | 192 | ND | ND | 12 | 556 |
| 84 | 142 | ND | 461 | ND | 23 | ND |
| 92 | 269 | ND | ND | ND | 1,120 | ND |
| 99 | 3,350 | ND | ND | ND | 1,690 | ND |
| 103 | 62 | 75 | ND | ND | ND | 115 |
| 104 | 186 | 41 | ND | ND | ND | 108 |
| 105 | 626 | 320 | ND | ND | ND | 652 |
| 107 | 177 | 95 | ND | ND | ND | 113 |
| 108 | 221 | 76 | ND | ND | ND | 259 |
| 109 | 479 | 51 | ND | ND | 307 | ND |
| 110 | 237 | 187 | ND | ND | ND | 239 |
| 113 | 242 | 281 | 281 | ND | ND | ND |
| 114 | 2,530 | 1,380 | ND | ND | ND | 1,690 |
| 115 | 676 | 486 | ND | ND | ND | 529 |
| 116 | 380 | 349 | ND | ND | ND | 639 |
| 117 | 2,060 | 1,120 | ND | ND | ND | 2,190 |
| 118 | 1,940 | 1,170 | ND | ND | ND | 1,620 |
| 119 | 146 | 117 | ND | ND | ND | 199 |
| 120 | 978 | 334 | ND | ND | ND | 259 |
| 121 | 310 | 608 | ND | ND | ND | 215 |
| 123 | 28,500 | 4,140 | ND | ND | ND | >10,000 |
| 128 | 128 | 910 | ND | ND | ND | 968 |

Example 4
In Vivo Models—Inhibition of Tumor Growth

The in vivo effect of a compound on the growth of human tumor cells can be evaluated by implanting human tumor cells into the hindflank of athymic mice and administering test compound to the mice. Human tumor cells originating from a variety of different tumor types, such as A375 human melanoma cells, are implanted subcutaneously into the hindflank of male athymic mice (Charles River) and allowed to establish a sizeable tumor for 6–10 days as determined by caliper measurements. Test compound is then administered by injecting the compound formulated in an appropriate vehicle intraperitoneally into the mice once a day for 30 days. The test compound can also be administered by other routes such as orally, sub cutaneously or by intravenous infusion. The size of the tumor in this study is measured every four days and the degree of inhibition is determined by comparing drug-treated animals to animals that are injected with vehicle only.

The synergistic action or enhancement of conventional chemotherapeutic agent by a test compound can also be determined with this model by comparing animals treated with the standard therapy alone to animals treated with test compound plus the same standard therapy. An additive effect on the delay of tumor growth will be observed if synergistic action due to test compound is occurring.

While the foregoing specification teaches the principles of the present invention, with examples provided for the purpose of illustration, it will be understood that the practice of the invention encompasses all of the usual variations, adaptations and modifications as come within the scope of the following claims and their equivalents.

Throughout this application, various publications are cited. The disclosure of these publications is hereby incorporated by reference into this application to describe more fully the state of the art to which this invention pertains.

What is claimed is:

1. A compound of the following formula:

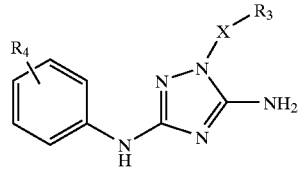

wherein $R_4$ is selected from the group consisting of:

$C_{1-8}$alkyl, which is optionally substituted on a terminal carbon with a substituent selected from the group consisting of —C(O)H, —C(O)($C_{1-8}$)alkyl, —$CO_2$H, —$CO_2$($C_{1-8}$)alkyl, amino, amino substituted with two substituents independently selected from the group consisting of hydrogen and $C_{1-8}$alkyl, cyano, (halo)$_{1-3}$, hydroxy, nitro, cycloalkyl, aryl, thienyl, imidazolinyl, and triazolyl;

$C_{1-8}$alkoxy or $C_{1-8}$alkoxy substituted on a terminal carbon with a substituent selected from the group consisting of (halo)$_{1-3}$ and hydroxy;

—C(O)H, —C(O)($C_{1-8}$)alkyl, —$CO_2$H, —$CO_2$($C_{1-8}$)alkyl;

amino, or amino substituted with two substituents independently selected from the group consisting of $C_{1-8}$alkyl and —$SO_2$—($C_{1-8}$)alkyl;

—C(O)amino, wherein amino is substituted with two substituents independently selected from the group consisting of hydrogen and $C_{1-8}$alkyl;

—$SO_2$—, substituted with one substituent selected from the group consisting of thienyl, imidazolinyl, triazolyl and amino, wherein amino is substituted with two substituents independently selected from the group consisting of hydrogen, $C_{1-8}$alkyl, —$C_{1-8}$alkylamino, wherein amino is substituted with two substituents independently selected from the group consisting of hydrogen and $C_{1-8}$alkyl, thienyl, imidazolinyl, and triazolyl;

cycloalkyl, aryl, thienyl, imidazolinyl, and triazolyl; wherein cycloalkyl, aryl, thienyl, imidazolinyl, and triazolyl are optionally substituted with 1 to 3 substituents independently selected from the group consisting of $C_{1-8}$alkyl, wherein alkyl is optionally substituted on a terminal carbon with a substituent selected from the group consisting of amino, or amino substituted with two substituents independently selected from the group consisting of hydrogen and $C_{1-8}$alkyl, cyano, (halo)$_{1-3}$, hydroxy and nitro, $C_{1-8}$alkoxy, amino, substituted with two substituents independently selected from the group consisting of hydrogen and $C_{1-8}$alkyl), cyano, halo, hydroxy and nitro; and, wherein thienyl, imidazolinyl, or triazolyl are optionally substituted with 1 to 2 oxo substituents;

X is selected from the group consisting of —C(O)—, —C(S)— and —SO$_2$—; and, $R_3$ is selected from the group consisting of:

$C_{1-8}$alkyl, $C_{2-8}$alkenyl, $C_{2-8}$alkynyl, wherein alkyl, alkenyl and alkynyl are optionally substituted on a terminal carbon with a substituent selected from the group consisting of —C(O)H, —C(O)(C$_{1-8}$)alkyl, —CO$_2$H, —CO$_2$(C$_{1-8}$)alkyl, or amino substituted with two substituents independently selected from the group consisting of hydrogen, cyano, (halo)$_{1-3}$, hydroxy, nitro, aryl and thienyl, imidazolinyl, or triazolyl; wherein aryl, thienyl, imidazolinyl, or triazolyl are optionally substituted with 1 to 3 substituents independently selected from the group consisting of $C_{1-8}$alkyl, cyano, halo, (halo)$_{1-3}$(C$_{1-8}$)alkyl, (halo)$_{1-3}$(C$_{1-8}$)alkoxy, hydroxy, hydroxy(C$_{1-8}$)alkyl, hydroxy(C$_{1-8}$)alkoxy and nitro;

cycloalkyl, thienyl, imidazolinyl, triazolyl, and aryl, wherein cycloalkyl, thienyl, imidazolinyl, triazolyl, and aryl are optionally substituted with 1 to 3 substituents independently selected from the group consisting of cyano, halo, hydroxy and nitro; and, wherein cycloalkyl, aryl, thienyl, imidazolinyl, or triazolyl are optionally substituted with 1 to 2 substituents independently selected from the group consisting of:

$C_{1-8}$alkyl, $C_{2-8}$alkenyl, wherein alkyl and alkenyl are optionally substituted on a terminal carbon with a substituent selected from the group consisting of —C(O)H, —C(O)(C$_{1-8}$)alkyl, —CO$_2$H, —CO$_2$(C$_{1-8}$) alkyl, amino, amino substituted with two substituents independently selected from the group consisting of hydrogen and $C_{1-8}$alkyl, cyano, (halo)$_{1-3}$, hydroxy, nitro, cycloalkyl, thienyl, imidazolinyl, triazolyl, and aryl, —CH(OH)—C$_{1-8}$ alkyl, $C_{1-8}$alkoxy, optionally substituted on a terminal carbon with a substituent selected from the group consisting of (halo)$_{1-3}$ and hydroxy;

—C(O)H, —C(O)(C$_{1-8}$)alkyl, —CO$_2$H, —CO$_2$(C$_{1-8}$) alkyl, amino, or amino substituted with two substituents independently selected from the group consisting of hydrogen, $C_{1-8}$alkyl and —C(O)(C$_{1-8}$)alkyl, —C(O)amino, wherein amino is substituted with two substituents independently selected from the group consisting of hydrogen and $C_{1-8}$alkyl, —SO$_2$—, substituted with one substituent selected from the group consisting of thienyl, imidazolinyl, triazolyl and amino, wherein amino is substituted with two substituents independently selected from the group consisting of hydrogen, $C_{1-8}$alkyl and —C$_{1-8}$alkylamino, wherein amino is substituted with two substituents independently selected from the group consisting of hydrogen and $C_{1-8}$alkyl;

—NH—SO$_2$—(C$_{1-8}$)alkyl, cycloalkyl, thienyl, imidazolinyl, triazolyl, optionally substituted with 1 to 2 oxo substituents, aryl, thienyl, imidazolinyl, and triazolyl, with a proviso when $R_3$ is amino substituted with two substitutents, the two substitutents independently are not selected from hydrogen and aryl, wherein aryl is phenyl;

and pharmaceutically acceptable salts thereof.

2. A compound of the following formula:

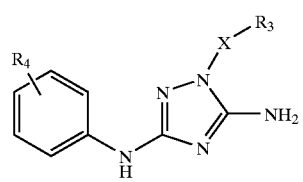

wherein $R_4$ is selected from the group consisting of:

amino, and amino substituted with two substituents independently selected from the group consisting of hydrogen, $C_{1-4}$alkyl and —SO$_2$—(C$_{1-4}$)alkyl);

—SO$_2$—, substituted with one substituent selected from the group consisting of amino, or amino substituted with two substituents independently selected from the group consisting of hydrogen, $C_{1-4}$alkyl, —C$_{1-4}$alkylamino, wherein —C$_{1-4}$alkylamino is substituted with two substituents independently selected from the group consisting of hydrogen and $C_{1-4}$alkyl;

X is selected from the group consisting of —CO(O)—, —C(S)— and —SO$_2$—;

and $R_3$ is selected from the group consisting of:

$C_{1-8}$alkyl, $C_{2-8}$alkenyl, $C_{2-8}$alkynyl, wherein alkyl, alkenyl and alkynyl are optionally substituted on a terminal carbon with a substituent selected from the group consisting of —C(O)H, —C(O)(C$_{1-8}$)alkyl, —CO$_2$H, —CO$_2$(C$_{1-8}$)alkyl, amino or amino substituted with two substituents independently selected from the group consisting of hydrogen and $C_{1-8}$alkyl, cyano, (halo)$_{1-3}$, hydroxy, nitro, aryl and thienyl, imidazolinyl, or triazolyl; wherein aryl, thienyl, imidazolinyl, or triazolyl are optionally substituted with 1 to 3 substituents independently selected from the group consisting of $C_{1-8}$alkyl, cyano, halo, (halo)$_{1-3}$(C$_{1-8}$)alkyl, (halo)$_{1-3}$(C$_{1-8}$)alkoxy, hydroxy, hydroxy(C$_{1-8}$)alkyl, hydroxy (C$_{1-8}$)alkoxy and nitro;

cycloalkyl, thienyl, imidazolinyl, triazolyl, and aryl, wherein cycloalkyl, thienyl, imidazolinyl, triazolyl, and aryl are optionally substituted with 1 to 3 substituents independently selected from the group consisting of cyano, halo, hydroxy and nitro; and, wherein cycloalkyl, aryl, thienyl, imidazolinyl, or triazolyl are optionally substituted with 1 to 2 substituents independently selected from the group consisting of:

$C_{1-8}$alkyl, $C_{2-8}$alkenyl, wherein alkyl and alkenyl are optionally substituted on a terminal carbon with a substituent selected from the group consisting of —C(O)H, —C(O)(C$_{1-8}$)alkyl, —CO$_2$H, —CO$_2$(C$_{1-8}$) alkyl, amino, amino substituted with two substituents independently selected from the group consisting of hydrogen and C$_{1-8}$alkyl, cyano, (halo)$_{1-3}$, hydroxy, nitro, cycloalkyl, thienyl, imidazolinyl, triazolyl, and aryl, —CH(OH)—(C$_{1-8}$)alkyl, C$_{1-8}$alkoxy, optionally substituted on a terminal carbon with a substituent selected from the group consisting of (halo)$_{1-3}$ and hydroxy;

—C(O)H, —C(O)(C$_{1-8}$)alkyl, —CO$_2$H, —CO$_2$(C$_{1-8}$) alkyl, amino, or amino substituted with two substituents independently selected from the group consisting of hydrogen, C$_{1-8}$alkyl and —C(O)(C$_{1-8}$)alkyl, —C(O)amino, wherein amino is substituted with two substituents independently selected from the group consisting of hydrogen and C$_{1-8}$alkyl, —SO$_2$—, substituted with one substituent selected from the group consisting of thienyl, imidazolinyl, triazolyl and amino, wherein amino is substituted with two substituents independently selected from the group consisting of hydrogen, C$_{1-8}$alkyl and —C$_{1-8}$alkylamino, wherein amino is substituted with two substituents independently selected from the group consisting of hydrogen and C$_{1-8}$alkyl;

—NH—SO$_2$—(C$_{1-8}$)alkyl, cycloalkyl, thienyl, imidazolinyl, triazolyl, optionally substituted with 1 to 2 oxo substituents, aryl, thienyl, imidazolinyl, and triazolyl;

and pharmaceutically acceptable salts thereof.

3. A compound of the following formula:

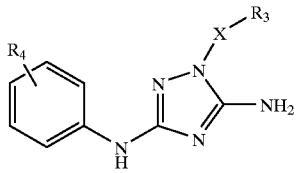

wherein

R$_4$ is selected from the group consisting of:

—SO$_2$—, substituted with one substituent selected from the group consisting of thienyl, imidazolinyl, triazolyl and amino, wherein amino is substituted with two substituents independently selected from the group consisting of hydrogen, C$_{1-8}$alkyl, —C$_{1-8}$alkylamino, wherein —C$_{1-8}$alkylamino is substituted with two substituents independently selected from the group consisting of hydrogen and C$_{1-8}$alkyl, thienyl, imidazolinyl, and triazolyl; and X is selected from the group consisting of —C(O)—, —C(S)— and —SO$_2$—;

R$_3$ is selected from the group consisting of:

C$_{1-8}$alkyl, C$_{2-8}$alkenyl, C$_{2-8}$alkynyl, cycloalkyl, thienyl, imidazolinyl, triazolyl, and phenyl;

wherein the C$_{1-8}$alkyl, C$_{2-8}$alkenyl, C$_{2-8}$alkynyl, cycloalkyl, thienyl, imidazolinyl, triazolyl, and phenyl substituents are optionally substituted with 1 to 3 substituents independently selected from the group consisting of C$_{1-8}$alkyl, C$_{1-8}$ alkyl(mono-, di- or tri-halo), C$_{1-8}$ alkoxy, cyano, halo, hydroxy and nitro —C(O)(C$_{1-8}$)alkyl and —CH(OH)(C$_{1-8}$)alkyl;

and pharmaceutically acceptable salts thereof.

4. The compound of claim 3 wherein X, R$_3$ and R$_4$ are dependently selected from the group consisting of:

| X | R$_3$ | R$_4$ |
|---|---|---|
| C(O) | (2,6-F$_2$)Ph | 4-SO$_2$—NH$_2$; |
| C(O) | (2,6-F$_2$-3-CH$_3$)Ph | 4-SO$_2$—NH$_2$; |
| C(O) | (2,4,6-F$_3$)Ph | 4-SO$_2$—NH$_2$; |
| C(O) | (2-F)Ph | 4-SO$_2$—NH$_2$; |
| C(O) | (2,4-F$_2$)Ph | 4-SO$_2$—NH$_2$; |
| C(O) | (2-F-6-CF$_3$)Ph | 4-SO$_2$—NH$_2$; |
| C(O) | (2,6-Cl$_2$)Ph | 4-SO$_2$—NH$_2$; |
| C(O) | (2,4,6-Cl$_3$)Ph | 4-SO$_2$—NH$_2$; |
| C(O) | (2-NO$_2$)Ph | 4-SO$_2$—NH$_2$; |
| C(O) | [2,6-(OCH$_3$)$_2$]Ph | 4-SO$_2$—NH$_2$; |
| C(O) | [2,4,6-(CH$_3$)$_3$]Ph | 4-SO$_2$—NH$_2$; |
| C(O) | Ph | 4-SO$_2$—NH$_2$; |
| C(O) | 2-thienyl | 4-SO$_2$—NH$_2$; |
| C(O) | (3-CH$_3$)2-thienyl | 4-SO$_2$—NH$_2$; |
| C(O) | (3-F)2-thienyl | 4-SO$_2$—NH$_2$; |
| C(O) | (3-Cl)2-thienyl | 4-SO$_2$—NH$_2$; |
| C(O) | (3-OCH$_2$CH$_3$)2-thienyl | 4-SO$_2$—NH$_2$; |
| C(O) | (3-NHCOCH$_3$)2-thienyl | 4-SO$_2$—NH$_2$; |
| C(O) | (5-CH$_3$)2-thienyl | 4-SO$_2$—NH$_2$; |
| C(O) | (5-Br)2-thienyl | 4-SO$_2$—NH$_2$; |
| C(O) | (5-COCH$_3$)2-thienyl | 4-SO$_2$—NH$_2$; |
| C(O) | 3-thienyl | 4-SO$_2$—NH$_2$; |
| C(O) | 3a, 7a-dihydrobenzo[b]thien-2-yl | 4-SO$_2$—NH$_2$; |
| C(O) | (5-CH$_2$CH$_3$)2-thienyl | 4-SO$_2$—NH$_2$; |
| C(O) | [3,5-(CH$_3$)$_2$]2-thienyl | 4-SO$_2$—NH$_2$; |
| C(O) | (3-Br)2-thienyl | 4-SO$_2$—NH$_2$; |
| C(O) | Cyclopentyl | 4-SO$_2$—NH$_2$; |
| C(O) | Cyclohexyl | 4-SO$_2$—NH$_2$; |
| C(O) | 2-thienyl-CH$_2$ | 4-SO$_2$—NH$_2$; |
| C(O) | 2-thienyl-(CH)$_2$ | 4-SO$_2$—NH$_2$; |
| C(O) | (2,6-F$_2$)—Ph—CH$_2$ | 4-SO$_2$—NH$_2$; |
| C(O) | (2,6-F$_2$)Ph(CH)$_2$ | 4-SO$_2$—NH$_2$; |
| C(O) | Cycloheptyl | 4-SO$_2$—NH$_2$; |
| C(O) | 4-CH$_3$-cyclohexyl | 4-SO$_2$—NH$_2$; |
| C(O) | 4-CH$_3$-cyclohexyl | 4-SO$_2$—NH$_2$; |
| C(O) | 4-(CH$_2$)$_3$CH$_3$-cyclohexyl | 4-SO$_2$—NH$_2$; |
| C(O) | 5-(2-pyridinyl)2-thienyl | 4-SO$_2$—NH$_2$; |
| C(O) | 3-(1H-pyrrol-1-yl)2-thienyl | 4-SO$_2$—NH$_2$; |
| C(O) | 5-[C(CH$_3$)$_3$]2-thienyl | 4-SO$_2$—NH$_2$; |
| C(O) | 5-[(CH)$_2$C(O)OC(CH$_3$)$_3$]2-thienyl | 4-SO$_2$—NH$_2$; |
| C(O) | (2,6-F$_2$-3-NO$_2$)Ph | 4-SO$_2$—NH$_2$; |
| C(O) | (2,6-F$_2$-3-NH$_2$)Ph | 4-SO$_2$—NH$_2$; |
| C(O) | [2,6-(CH$_3$)$_2$]Ph | 4-SO$_2$—NH$_2$; |
| C(O) | (2-CH$_3$)Ph | 4-SO$_2$—NH$_2$; |
| C(O) | [2,6-F$_2$-3-CH(OH)CH$_3$]Ph | 4-SO$_2$—NH$_2$; |
| C(O) | (2,6-F$_2$)Ph | 4-SO$_2$—NH$_2$; |
| C(O) | (2,6-F$_2$3-CH$_3$)Ph | 4-SO$_2$—NH$_2$; |
| C(S) | —NH[(2,6-F$_2$)Ph] | 4-SO$_2$—NH$_2$; |
| C(O) | —NH[(2,6-F$_2$)Ph] | 4-SO$_2$—NH$_2$; |
| SO$_2$ | (2,6-F$_2$)Ph | 4-SO$_2$—NH$_2$; |
| C(O) | (2-Cl-3-CH$_3$-6-F)Ph | 4-SO$_2$—NH$_2$; |
| C(O) | (2-Cl-6-F)Ph | 4-SO$_2$—NH$_2$; and |
| C(O) | (2,6-F$_2$-5-Cl)Ph | 4-SO$_2$—NH$_2$. |

5. The compound of claim 3 wherein X, R$_3$ and R$_4$ are dependently selected from the group consisting of:

| X | R$_3$ | R$_4$ |
|---|---|---|
| C(O) | (2,6-F$_2$)Ph | 4-SO$_2$—NH$_2$; |
| C(O) | (2,6-F$_2$-3-CH$_3$)Ph | 4-SO$_2$—NH$_2$; and |
| C(S) | —NH[(2,6-F$_2$)Ph] | 4-SO$_2$—NH$_2$. |

6. The compound of claim 3 which is selected from the group consisting of:

5-amino-3-[[4-(aminosulfonyl)phenyl]amino]-N-(2,6-difluorophenyl)-1H-1,2,4-triazole-1-carbothioamide;

5-amino-3-[[4-(aminosulfonyl)phenyl]amino]-N-(2,6-difluorophenyl)-1H-1,2,4-triazole-1-carboxamide;

4-[[5-amino-1-(2-chloro-6-fluoro-3-methylbenzoyl)-1H-1,2,4-triazol-3-yl]amino]-benzenesulfonamide;
4-[[5-amino-1-(2-chloro-6-fluorobenzoyl)-1H-1,2,4-triazol-3-yl]amino]-benzenesulfonamide;
4-[[5-amino-1-(2,6-difluoro-3-methylbenzoyl)-1H-1,2,4-triazol-3-yl]amino]-N-methyl-benzenesulfonamide;
4-[[5-amino-1-[(3-methyl-2-thienyl)carbonyl]-1H-1,2,4-triazol-3-yl]amino]-N-methyl-benzenesulfonamide;
4-[[5-amino-1-[(3-methyl-2-thienyl)carbonyl]-1H-1,2,4-triazol-3-yl]amino]-N-[2-(dimethylamino)ethyl]-benzenesulfonamide;
1-[4-[[5-amino-1-[(3-methyl-2-thienyl)carbonyl]-1H-1,2,4-triazol-3-yl]amino]phenyl]-2-imidazolidinone.

7. The compound of claim 3 wherein X, $R_3$ and $R_4$ are dependently selected from the group consisting of:

| X | $R_3$ | $R_4$ |
|---|---|---|
| C(O) | (2,6-$F_2$)Ph | 4-$SO_2$—NH($CH_2CH_3$); |
| C(O) | (2,6-$F_2$)Ph | 4-$SO_2$—NH($CH_3$); |
| C(O) | (2,6-$F_2$-3-$CH_3$)Ph | 4-$SO_2$—NH($CH_3$); |
| C(O) | (3-$CH_3$)2-thienyl | 4-$SO_2$—NH($CH_3$); |
| C(O) | [3,5-($CH_3$)$_2$]2-thienyl | 4-$SO_2$—NH($CH_3$); |
| C(O) | (5-$CH_2CH_3$)2-thienyl | 4-$SO_2$—NH($CH_3$); |
| C(O) | [3,5-($CH_3$)$_2$]2-thienyl | 4-$SO_2$—N($CH_3$)$_2$; |
| C(O) | (5-$CH_2CH_3$)2-thienyl | 4-$SO_2$—N($CH_3$)$_2$; |
| C(O) | (3-$CH_3$)2-thienyl | 4-$SO_2$—N($CH_3$)$_2$; |
| C(O) | (2,6-$F_2$-3-$CH_3$)Ph | 4-$SO_2$—N($CH_3$)$_2$; and |
| C(O) | (2,6-$F_2$)Ph | 4-$SO_2$—N($CH_3$)$_2$. |

8. The compound of claim 3 wherein X, $R_3$ and $R_4$ are dependently selected from the group consisting of:

| X | $R_3$ | $R_4$ |
|---|---|---|
| C(O) | (2,6-$F_2$-3-$CH_3$)Ph | 4-(1-H-1,2,4-triazol-1-yl); |
| C(O) | (2,6-$F_2$)Ph | 4-(1-H-1,2,4-triazol-1-yl); |
| C(O) | (5-$CH_2CH_3$)2-thienyl | 4-(1-H-1,2,4-triazol-1-yl); |
| C(O) | [3,5-($CH_3$)$_2$]2-thienyl | 4-(1-H-1,2,4-triazol-1-yl); |
| C(O) | (3-$CH_3$)2-thienyl | 4-(1-H-1,2,4-triazol-1-yl); |
| C(O) | (2,6-$F_2$)Ph | 4-(1-H-1,3,4-triazol-1-yl); |
| C(O) | (2,6-$F_2$-3-$CH_3$)Ph | 4-(1-H-1,3,4-triazol-1-yl); and |
| C(O) | (3-$CH_3$)2-thienyl | 4-(1-H-1,3,4-triazol-1-yl). |

9. The compound of claim 3 wherein X, $R_3$ and $R_4$ are dependently selected from the group consisting of:

| X | $R_3$ | $R_4$ |
|---|---|---|
| C(O) | (2,6-$F_2$-3-$CH_3$)Ph | 4-(1-H-1,2,4-triazol-1-yl); |
| C(O) | (2,6-$F_2$)Ph | 4-(1-H-1,2,4-triazol-1-yl); |
| C(O) | (5-$CH_2CH_3$)2-thienyl | 4-(1-H-1,2,4-triazol-1-yl); |
| C(O) | [3,5-($CH_3$)$_2$]2-thienyl | 4-(1-H-1,2,4-triazol-1-yl); |
| C(O) | (3-$CH_3$)2-thienyl | 4-(1-H-1,2,4-triazol-1-yl); |
| C(O) | (2,6-$F_2$-3-$CH_3$)Ph | 4-(1-H-1,3,4-triazol-1-yl); |
| C(O) | (3-$CH_3$)2-thienyl | 4-(1-H-1,3,4-triazol-1-yl). |

10. The compound of claim 3 wherein X, $R_3$ and $R_4$ are dependently selected from the group consisting of:

| X | $R_3$ | $R_4$ |
|---|---|---|
| C(O) | (5-$CH_2CH_3$)2-thienyl | 4-$SO_2$—NH[($CH_2$)$_2$N($CH_3$)$_2$]; |
| C(O) | (3-$CH_3$)2-thienyl | 4-$SO_2$—NH[($CH_2$)$_2$N($CH_3$)$_2$]; |
| C(O) | (2,6-$F_2$-3-$CH_3$)Ph | 4-$SO_2$—NH[($CH_2$)$_2$N($CH_3$)$_2$]; |
| C(O) | (2,6-$F_2$)Ph | 4-$SO_2$—NH[($CH_2$)$_2$N($CH_3$)$_2$]; |
| C(O) | [3,5-($CH_3$)$_2$]2-thienyl | 4-$SO_2$—NH[($CH_2$)$_2$N($CH_3$)$_2$]; |
| C(O) | [3,5-($CH_3$)$_2$]2-thienyl | 4-NH—$SO_2$—$CH_3$; |
| C(O) | (3-$CH_3$)2-thienyl | 4-NH—$SO_2$—$CH_3$; |
| C(O) | (5-$CH_2CH_3$)2-thienyl | 4-NH—$SO_2$—$CH_3$; |
| C(O) | (2,6-$F_2$)Ph | 4-NH—$SO_2$—$CH_3$; and |
| C(O) | (2,6-$F_2$-3-$CH_3$)Ph | 4-NH—$SO_2$—$CH_3$. |

11. A pharmaceutical composition comprising a compound of claim 1 and a pharmaceutically acceptable carrier.

12. A pharmaceutical composition made by mixing a compound of claim 1 and a pharmaceutically acceptable carrier.

* * * * *